(12) United States Patent
Baker et al.

(10) Patent No.: US 9,840,539 B2
(45) Date of Patent: Dec. 12, 2017

(54) HIGH AFFINITY DIGOXIGENIN BINDING PROTEINS

(71) Applicant: UNIVERSITY OF WASHINGTON THROUGH ITS CENTER FOR COMMERCIALIZATION, Seattle, WA (US)

(72) Inventors: David Baker, Seattle, WA (US); Christine E. Tinberg, Seattle, WA (US); Sagar D. Khare, New Brunswick, NJ (US); Jiayi Dou, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 77 days.

(21) Appl. No.: 14/766,259

(22) PCT Filed: Mar. 13, 2014

(86) PCT No.: PCT/US2014/025500
§ 371 (c)(1),
(2) Date: Aug. 6, 2015

(87) PCT Pub. No.: WO2014/159947
PCT Pub. Date: Oct. 2, 2014

(65) Prior Publication Data
US 2015/0376246 A1 Dec. 31, 2015

Related U.S. Application Data

(60) Provisional application No. 61/784,618, filed on Mar. 14, 2013.

(51) Int. Cl.
| | | |
|---|---|---|
| *A61K 38/16* | (2006.01) |
| *C07K 1/00* | (2006.01) |
| *C07K 14/435* | (2006.01) |
| *G01N 33/74* | (2006.01) |
| *C12N 15/10* | (2006.01) |
| *A61K 38/00* | (2006.01) |

(52) U.S. Cl.
CPC ......... *C07K 14/435* (2013.01); *G01N 33/743* (2013.01); *A61K 38/005* (2013.01); *C12N 15/1034* (2013.01)

(58) Field of Classification Search
None
See application file for complete search history.

(56) References Cited

U.S. PATENT DOCUMENTS

| 7,001,882 B1 | 2/2006 | Schlehuber |
| 2007/0020624 A1 | 2/2007 | Rubenfield et al. |

FOREIGN PATENT DOCUMENTS

| DE | 3508307 A1 | 4/1986 | |
| WO | WO 2005/097994 | * 10/2005 | ............. C12N 15/12 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
PCT/US2014/025500, ISR/WO, 2014.
Potterton, et al., "A graphical user interface to the CCP4 program suite," Acta Crystallogr. Sect. D, vol. 59, pp. 1131-1137, 2003.
Raman, et al., "Structure prediction for CASP8 with all-atom refinement using Rosetta," Proteins, vol. 77, Suppl S9, pp. 89-99, 2009.
Richter, et al., "De novo enzyme design using Rosetta3," PLoS One, vol. 6, No. 5, e19230, 2011.
Rossi, et al., "Analysis of protein-ligand interactions by fluorescence polarization," Nature Protocols, vol. 6, No. 3, pp. 365-387, 2011.
Röthlisberger, et al., "Kemp elimination catalysts by computational enzyme design," Nature, vol. 453, No. 7192, pp. 190-195, 2008.
Schlehuber, et al., "A novel type of receptor protein, based on the lipocalin scaffold, with specificity for digoxigenin," J. Mol. Biol., vol. 297, pp. 1105-1120, 2000.
Schreier, et al., "Computational design of ligand binding is not a solved problem," Proceedings of the National Academy of Sciences USA, vol. 106, No. 44, pp. 18491-18496, 2009.
Shen, et al., "Vaccines against drug abuse," Clinical Pharmacology and Therapeutics, vol. 91, No. 1, pp. 60-70., 2012.
Siegel, et al., "Computational design of an enzyme catalyst for a stereoselective bimolecular Diels-Alder reaction," Science, vol. 329, No. 5989, pp. 309-313, 2010.
Telmer, et al., "Structural studies of an engineered zinc biosensor reveal an unanticipated mode of zinc binding," Journal of Molecular Biology, vol. 354, No. 4, pp. 829-840, 2005.
The Digitalis Investigation Group, "The effect of digoxin on mortality and morbidity in patients with heart failure," New England Journal of Medicine, vol. 336, No. 8, pp. 525-533., 1997.
Tinberg et al., "Computational design of ligand-binding proteins with high affinity and selectivity," Nature, vol. 501, No. 7466, pp. 212-216, 2013.
Tyka, et al., "Alternate states of proteins revealed by detailed energy landscape mapping," J. Mol. Biol., vol. 405, pp. 607-618, 2011.
Vaguine, et al., "SFCHECK: a unified set of procedures for evaluating the quality of macromolecular structure-factor data and their agreement with the atomic model," Acta Crystallogr. Sect. D, vol. 55, pp. 191-205, 1999.
Wang, et al., "Structural analyses of covalent enzyme-substrate analog complexes reveal strengths and limitations of de novo enzyme design," Journal of Molecular Biology, vol. 415, No. 3, pp. 615-625, 2012.
Whitehead, et al., "Optimization of affinity, specificity and function of designed influenza inhibitors using deep sequencing," Nature Biotechnology, vol. 30, No. 6, pp. 543-548, 2012.
Winn, et al., "Overview of the CCP4 suite and current developments," Acta Crystallogr. Sect. D, vol. 67, pp. 235-242, 2011.
Zanghellini, et al., "New algorithms and an in silico benchmark for computational enzyme design," Protein Science, vol. 15, No. 12, pp. 2785-2794, 2006.
Baker, "An exciting but challenging road ahead for computational enzyme design," Protein Science, vol. 19, No. 10, pp. 1817-1819, 2010.

(Continued)

*Primary Examiner* — Shulamith H Shafer
(74) *Attorney, Agent, or Firm* — McDonnell Boehnen Hulbert & Berghoff LLP

(57) ABSTRACT

Isolated polypeptides with steroid binding activity and methods for their use as therapeutics and detection agents are disclosed herein.

11 Claims, 41 Drawing Sheets

(56) References Cited

OTHER PUBLICATIONS

Benatuil, et al., "An improved yeast transformation method for the generation of very large human antibody libraries," Protein Engineering, Design and Selection, vol. 23, No. 4, pp. 155-159, 2010.
Boehr, et al., "The role of dynamic conformational ensembles in biomolecular recognition," Nature Chemical Biology, vol. 5, No. 11, pp. 789-796, 2009.
Bradbury, et al., "Beyond natural antibodies: the power of in vitro display technologies," Nature Biotechnology, vol. 29, No. 3, pp. 245-254, 2011.
Brustad, et al., "Optimizing non-natural protein function with directed evolution," Current Opinion in Chemical Biology, vol. 15, No. 2, pp. 201-210, 2011.
Chao, et al., "Isolating and engineering human antibodies using yeast surface display," Nature Protocols, vol. 1, No. 2, pp. 755-768, 2006.
Chen, et al., "Isolation of high-affinity ligand-binding proteins by periplasmic expression with cytometric screening (PECS)," Nature Biotechnology, vol. 19, No. 6, pp. 537-542, 2001.
Chen, et al., "MolProbity: all-atom structure validation for macromolecular crystallography," Acta Crystallogr. Sect. D, vol. 66, pp. 12-21, 2010.
Chugani, et al., "Strain-dependent diversity in the Pseudomonas aeruginosa quorum-sensing regulon," Proceedings of the National Academy of Sciences, vol. 109, No. 41, pp. E2823-E2831, 2012.
Collaborative Computational Project, "The CCP4 suite: programs for protein crystallography," Acta Crystallographica, Section D, Biological Crystallography, vol. 50(Pt 5), No. 4, pp. 760-763, 1994.
Cooper, et al., "Predicting protein structures with a multiplayer online game," Nature, vol. 466, No. 7307, pp. 756-760, 2010.
Davis, et al., "RosettaLigand docking with full ligand and receptor flexibility," Journal of Molecular Biology, vol. 385, No. 2, pp. 381-392, 2009.
Database UniProt (Apr. 3, 2007), Database Accession No. A3LDC9.
Database UniProt (Jan. 25, 2012) Database Accession No. G5FN39.
Database UniProt (Nov. 28, 2012) Database Accession No. K1DMJ3.
de Wolf, et al., "Ligand-binding proteins: their potential for application in systems for controlled delivery and uptake of ligands," Pharmacological Reviews, vol. 52, No. 2, pp. 207-236, 2000.
Eisel, et al., DIG Application Manual for Nonradioactive In Situ Hybridization, 4th Edition, Roche Diagnostics GmbH, 224 pages, 2008.
Emsley, et al., "Coot: model-building tools for molecular graphics," Acta Crystallogr. Sect. D, vol. 60, pp. 2126-2132, 2004.
Fersht, et al., "Hydrogen bonding and biological specificity analysed by protein engineering," Nature, vol. 314, No. 6008, pp. 235-238, 1985.
Flanagan, et al., "Fab antibody fragments: some applications in clinical toxicology," Drug Safety, No. 27, vol. 14, pp. 1115-1133, 2004.
Fleishman, et al., "Computational design of proteins targeting the conserved stem region of influenza hemagglutinin," Science, vol. 332, pp. 816-821, 2011.
Fleishman, et al., "Restricted sidechain plasticity in the structures of native proteins and complexes," Protein Science, vol. 20, No. 4, pp. 753-757, 2011.
Fleishman, et al., "Role of the biomolecular energy gap in protein design, structure, and evolution," Cell, vol. 149, No. 2, pp. 262-273, 2012.
Fleishman, et al., "RosettaScripts: a scripting language interface to the Rosetta macromolecular modeling suite," PLoS One, vol. 6, No. 6, e20161, 2011.
Fowler, et al., "Enrich: software for analysis of protein function by enrichment and depletion of variants," Bioinformatics, vol. 27, No. 24, pp. 3430-3431, 2011.
Fowler, et al., "High-resolution mapping of protein sequence-function relationships," Nature Methods, vol. 7, No. 9, pp. 741-746, 2010.
Frederick, et al., "Conformational entropy in molecular recognition by proteins," Nature, vol. 448, No. 7151, pp. 325-329, 2007.
Gietz, et al., "High-efficiency yeast transformation using the LiAc/SS carrier DNA/PEG method," Nat. Protoc., vol. 2, pp. 31-34, 2007.
Holm, et al., "Dali server: conservation mapping in 3D," Nucleic Acids Research, vol. 38(Web Server Issue), pp. W545-W549, 2010.
Hoover, et al., "DNAWorks: an automated method for designing oligonucleotides for PCR-based gene synthesis," Nucleic Acids Res., vol. 30, pp. e43-e43, 2002.
Hunter, et al., "High-affinity monoclonal antibodies to the cardiac glycoside, digoxin," Journal of Immunology, vol. 129, No. 3, pp. 1165-1172, 1982.
Jeffrey, et al., "26-10 Fab-digoxin complex: affinity and specificity due to surface complementarity," Proceedings of the National Academy of Sciences USA, vol. 90, No. 21, pp. 10310-10314, 1993.
Jiang, et al., "De novo computational design of retro-aldol enzymes," Science, vol. 319, No. 5868, pp. 1387-1391, 2008.
Kellogg, et al., "Role of conformational sampling in computing mutation-induced changes in protein structure and stability," Proteins, vol. 79, No. 3, pp. 830-838, 2011.
Khare, et al., "Emerging themes in the computational design of novel enzymes and protein-protein interfaces," FEBS Letters, vo. 587, No. 8, pp. 1147-1154, 2013.
Khersonsky, et al., "Bridging the gaps in design methodologies by evolutionary optimization of the stability and proficiency of designed Kemp eliminase KE59," Proceedings of the National Academy of Sciences USA, vol. 109, No. 26, pp. 10358-10363, 2012.
Kim, et al., "Crystal structure of the conserved hypothetical protein PA3332 from Pseudomonas aeruginosa,"; MMDB ID: 32993, PDB ID: 1Z1S, 2005.
Korndörfer, et al., "Structural mechanism of specific ligand recognition by a lipocalin tailored for the complexation of digoxigenin," Journal of Molecular Biology, vol. 330, No. 2, pp. 385-396, 2003.
Kuhlman, et al., "Design of a novel globular protein fold with atomic-level accuracy," Science, vol. 302, pp. 1364-1368, 2003.
Kuhlman, et al., "Native protein sequences are close to optimal for their structures," Proceedings of the National Academy of Sciences USA, vol. 97, No. 19, pp. 10383-10388, 2000.
Kunkel, "Rapid and efficient site-specific mutagenesis without phenotypic selection," Proceedings of the National Academy of Sciences USA, vol. 82, pp. 488-492, 1985.
Laskowski, et al., "PROCHECK: a program to check the stereochemical quality of protein structures," J. Appl. Crystallogr., vol. 26, pp. 283-291, 1993.
Lawrence, et al., "Shape complementarity at protein/protein interfaces," Journal of Molecular Biology, vol. 234, No. 4, pp. 946-950, 1993.
Mathee, et al., "Dynamics of Pseudomonas aeruginosa genome evolution," Proceedings of the National Academy of Sciences, vol. 105, No. 8, pp. 3100-3105, 2008.
Mazor, et al., "Isolation of engineered, full-length antibodies from libraries expressed in *Escherichia coli*," Nat. Biotechnol., vol. 25, pp. 563-565, 2007.
McCoy, et al., "Phaser crystallographic software," J. Appl. Crystallogr., vol. 40, pp. 658-674, 2007.
McLaughlin, Jr. et al., "The spatial architecture of protein function and adaptation," Nature, vol. 491, No. 7422, pp. 138-142, 2012.
Murshudov, et al., "Refinement of macromolecular structures by the maximum-likelihood method," Acta Crystallogr. Sect. D, vol. 53, pp. 240-255, 1997.
Nilsson, et al., "A synthetic IgG-binding domain based on staphylococcal protein A," Protein Eng., vol. 1, pp. 107-113, 1987.
Nivón, et al., "A pareto-optimal refinement method for protein design scaffolds," 2013.
Otwinowski, et al., "Processing of X-ray diffraction data collected in oscillation mode," in Methods in Enzymology, Academic Press, vol. 276, pp. 307-326, 1997.

* cited by examiner

```
              1         10        20        30        40        50        60
              |         |         |         |         |         |         |
      1zls    MNAKEIVHSLRLIENGDARGNDLPHPEGVEFPYAPPGKTRFEGRETIWAHRLFPE
      DIG10   MNAKEIVHSLRLIENGDARGNDLPHPEGVEPYAPPGKTRFEGRETIWAHRLFPE
      DIG10.1 MNAKEIVHSLRLIENGDARGNDLPHPEGVEPYAPPGKTRFEGRETIWAHRLFPE
      DIG10.2 MNAKEIVHSLRLIENGDARGNDLPHPEGVEPYPPGYKTRFEGRETIWAHRLFPE
      DIG10.3 MNAKEIVHSLRLIENGDARGNDLPHPEGVEPYPPGYKTRFEGRETIWAHRLFPE
                                                  *

61        70        80        90        100       110       120
              |         |         |         |         |         |         |
      1zls    HLTVRFTDVQFYETADPDLAIGEHGDVATYSGGKLADYIEVLRTRDGQILLTRDFPN
      DIG10   HTVRFTDVQFYETADPDLAIGEHGDVTYSGGKLADYIEVLRTRDGQILLTRPN
      DIG10.1 HTVRFTDVQFYETADPDLAIGEHGDVTYSGGKLADYIEVLRTRDGQILLTRPN
      DIG10.2 HTVRFTDVQFYSTADPDLAIGEHGDVTYSGGKLADYIEVLRTRDGQILLTRPN
      DIG10.3 HTVRFTDVQFYETADPDLAIGEHGDVTYSGGKLADYIEVLRTRDGQILLTRPN
                                                       *              *

121       130       140
              |         |         |
      1zls    PLRHLSALGGVERAAKIVQGA  (SEQ ID NO: 24)
      DIG10   PLRLEALGGVERAAKIVQGA   (SEQ ID NO: 12)
      DIG10.1 PLRLEALGGVERAAKIVQGA   (SEQ ID NO: 13)
      DIG10.2 PLRLEALGGVERAAKIVQGA   (SEQ ID NO: 14)
      DIG10.3 PLRLEALGGVERAAKIVQGA   (SEQ ID NO: 15)
```

FIGURE 22

SEQUENCE LISTING

```
<160> NUMBER OF SEQ ID NOS: 24

<210> SEQ ID NO 1
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is A, I, L, V, M, F, W, P, or G or is
      absent
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is A, I, L, V, M, F, W, P, or G
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is A, I, L, V, M, F, W, P, or G
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is A, I, L, V, M, F, W, P, or G
<220> FEATURE:
<221> NAME/KEY: MISC_FEATURE
<222> LOCATION: (12)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is A, I, L, V, M, F, W, P, or G
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
```

```
<222> LOCATION: (17)..(17)
<223> OTHER INFORMATION: Xaa is G, A, or S
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, I, L, V, M, F, W, P, or G
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Y, W, F, H, N, Q, T, S, or C
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (25)..(26)
<223> OTHER INFORMATION: Xaa is A, I, L, V, M, F, W, P, or G
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is A, I, L, V, M, F, W, P, or G
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is G, A, or S
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is A, I, L, V, M, F, W, P, G, H, N, Q, Y,
      T, S or C
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is Y, W, or F
<220> FEATURE:
<221> NAME/KEY: MISC_FEATURE
<222> LOCATION: (35)..(35)
<223> OTHER INFORMATION: Xaa is A, I, L, V, M, F, W, P, or G
<220> FEATURE:
<221> NAME/KEY: MISC_FEATURE
<222> LOCATION: (36)..(36)
<223> OTHER INFORMATION: Xaa is Y, H, N, Q, T, S, or C
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(40)
<223> OTHER INFORMATION: Xaa is A, I, L, V, M, F, W, P, or G
<220> FEATURE:
<221> NAME/KEY: MISC_FEATURE
<222> LOCATION: (41)..(42)
<223> OTHER INFORMATION: Xaa is any amino acid
```

```
<220> FEATURE:
<221> NAME/KEY: MISC_FEATURE
<222> LOCATION: (43)..(43)
<223> OTHER INFORMATION: Xaa is Y, H, N, Q, T, S, or C
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is A, I, L, V, M, F, W, P, G, H, N, Q, Y,
     T, S or C
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is G, A, or S
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is A, I, L, V, M, F, W, P, or G
<220> FEATURE:
<221> NAME/KEY: MISC_FEATURE
<222> LOCATION: (52)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is A, I, L, V, M, F, W, P, G, H, N, Q, Y,
     T, S, K, R or C
<220> FEATURE:
<221> NAME/KEY: MISC_FEATURE
<222> LOCATION: (55)..(55)
<223> OTHER INFORMATION: Xaa is A, I, L, V, M, F, W, P, or G
<220> FEATURE:
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is A, I, L, V, M, F, W, P, G, H, N, Q, Y,
     T, S, K, R or C
<220> FEATURE:
<221> NAME/KEY: MISC_FEATURE
<222> LOCATION: (59)..(59)
<223> OTHER INFORMATION: Xaa is A, I, L, V, M, F, W, P, or G
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is A, I, L, V, M, F, W, P, or G
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is A, I, L, V, M, F, W, P, or G
```

```
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (71)..(71)
<223> OTHER INFORMATION: Xaa is A, I, L, V, M, F, W, P, or G
<220> FEATURE:
<221> NAME/KEY: MISC_FEATURE
<222> LOCATION: (72)..(72)
<223> OTHER INFORMATION: Xaa is Y, W, or F
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is Y, H, N, Q, T, S, or C
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is A, I, L, V, M, F, W, P, or G
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, I, L, V, M, F, W, P, or G
<220> FEATURE:
<221> NAME/KEY: MISC_FEATURE
<222> LOCATION: (81)..(81)
<223> OTHER INFORMATION: Xaa is A, I, L, V, or M
<220> FEATURE:
<221> NAME/KEY: MISC_FEATURE
<222> LOCATION: (82)..(82)
<223> OTHER INFORMATION: Xaa is G, A, or S
<220> FEATURE:
<221> NAME/KEY: MISC_FEATURE
<222> LOCATION: (83)..(83)
<223> OTHER INFORMATION: Xaa is D or E
<220> FEATURE:
<221> NAME/KEY: MISC_FEATURE
<222> LOCATION: (84)..(84)
<223> OTHER INFORMATION: Xaa is A, I, L, V, M, F, W, P, G, R, D, E, H or
      K
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is A, I, L, V, M, F, W, P, G, H, N, Q, Y,
      T, S or C
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(88)
<223> OTHER INFORMATION: Xaa is A, I, L, V, M, F, W, P, G, H, N, Q, Y,
      T, S or C
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is A, I, L, V, M, F, W, P, G, H, N, Q, Y,
```

```
          T, S or C
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is A, I, L, V, M, F, W, P, G, R or K
<220> FEATURE:
<221> NAME/KEY: MISC_FEATURE
<222> LOCATION: (102)..(102)
<223> OTHER INFORMATION: Xaa is A, I, L, V, or M
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (104)..(104)
<223> OTHER INFORMATION: Xaa is A, I, L, V, or M
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (107)..(107)
<223> OTHER INFORMATION: Xaa is A, I, L, V, M, F, W, P, G, H, N, Q, Y,
      T, S or C
<220> FEATURE:
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is G, A, or S
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (112)..(112)
<223> OTHER INFORMATION: Xaa is A, I, L, V, M, F, W, P, G, H, N, Q, Y,
      T, S, K, R or C
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is A, I, L, V, M, F, W, P, or G
<220> FEATURE:
<221> NAME/KEY: MISC_FEATURE
<222> LOCATION: (116)..(116)
<223> OTHER INFORMATION: Xaa is R or K
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (118)..(118)
<223> OTHER INFORMATION: Xaa is Y, W, or F
<220> FEATURE:
<221> NAME/KEY: MISC_FEATURE
<222> LOCATION: (119)..(119)
<223> OTHER INFORMATION: Xaa is H, N, Q, Y, T, S, C, W, F, K, or R
<220> FEATURE:
<221> NAME/KEY: MISC_FEATURE
<222> LOCATION: (120)..(120)
<223> OTHER INFORMATION: Xaa is Y, H, N, Q, T, S, or C
<220> FEATURE:
<221> NAME/KEY: MISC_FEATURE
<222> LOCATION: (121)..(121)
<223> OTHER INFORMATION: Xaa is A, I, L, V, M, F, W, P, or G
```

```
<220> FEATURE:
<221> NAME/KEY: MISC_FEATURE
<222> LOCATION: (122)..(122)
<223> OTHER INFORMATION: Xaa is A, I, L, V, or M
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is A, I, L, V, M, F, W, P, G, N, Q, Y, T,
      S, D, E, H or C
<220> FEATURE:
<221> NAME/KEY: MISC_FEATURE
<222> LOCATION: (125)..(125)
<223> OTHER INFORMATION: Xaa is A, I, L, V, or M
<220> FEATURE:
<221> NAME/KEY: MISC_FEATURE
<222> LOCATION: (126)..(129)
<223> OTHER INFORMATION: Xaa is any amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa

<210> SEQ ID NO 2
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is A, I, L, V, M, F, W, P, or G or absent
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is A, I, L, V, M, F, W, P, or G
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is A, I, L, V, M, F, W, P, or G
<220> FEATURE:
<221> NAME/KEY: MISC_FEATURE
```

```
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is A, I, L, V, M, F, W, P, or G
<220> FEATURE:
<221> NAME/KEY: MISC_FEATURE
<222> LOCATION: (12)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is A, I, L, V, M, F, W, P, or G
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is G, A, or S
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, I, L, V, M, F, W, P, or G
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is H, N, Q, Y, T, S, C, Y, W, or F
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (25)..(26)
<223> OTHER INFORMATION: Xaa is A, I, L, V, M, F, W, P, or G
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is A, I, L, V, M, F, W, P, or G
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is G, A, or S
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is F or Y
```

-continued

```
<220> FEATURE:
<221> NAME/KEY: MISC_FEATURE
<222> LOCATION: (35)..(35)
<223> OTHER INFORMATION: Xaa is A, I, L, V, M, F, W, P, or G
<220> FEATURE:
<221> NAME/KEY: MISC_FEATURE
<222> LOCATION: (36)..(36)
<223> OTHER INFORMATION: Xaa is H, N, Q, Y, T, S, or C
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(40)
<223> OTHER INFORMATION: Xaa is A, I, L, V, M, F, W, P, or G
<220> FEATURE:
<221> NAME/KEY: MISC_FEATURE
<222> LOCATION: (41)..(42)
<223> OTHER INFORMATION: Xaa is any amino acid
<220> FEATURE:
<221> NAME/KEY: MISC_FEATURE
<222> LOCATION: (43)..(43)
<223> OTHER INFORMATION: Xaa is H, N, Q, Y, T, S, or C
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is G, A, or S
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is A, I, L, V, M, F, W, P, or G
<220> FEATURE:
<221> NAME/KEY: MISC_FEATURE
<222> LOCATION: (52)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is A, I, L, V, M, F, W, P, G. H, N, Q, Y,
      T, S, K, R, or C
<220> FEATURE:
<221> NAME/KEY: MISC_FEATURE
<222> LOCATION: (55)..(55)
<223> OTHER INFORMATION: Xaa is A, I, L, V, M, F, W, P, or G
<220> FEATURE:
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is A, I, L, V, M, F, W, P, G. H, N, Q, Y,
      T, S, K, R, or C
<220> FEATURE:
<221> NAME/KEY: MISC_FEATURE
<222> LOCATION: (59)..(59)
<223> OTHER INFORMATION: Xaa is A, I, L, V, M, F, W, P, or G
<220> FEATURE:
<221> NAME/KEY: MISC_FEATURE
<222> LOCATION: (60)..(61)
<223> OTHER INFORMATION: Xaa is any amino acid
```

```
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is A, I, L, V, M, F, W, P, or G
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is A, I, L, V, M, F, W, P, or G
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (71)..(71)
<223> OTHER INFORMATION: Xaa is A, I, L, V, M, F, W, P, or G
<220> FEATURE:
<221> NAME/KEY: MISC_FEATURE
<222> LOCATION: (72)..(72)
<223> OTHER INFORMATION: Xaa is Y, W, or F
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is H, N, Q, Y, T, S, or C
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is A, I, L, V, M, F, W, P, or G
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, I, L, V, M, F, W, P, or G
<220> FEATURE:
<221> NAME/KEY: MISC_FEATURE
<222> LOCATION: (81)..(81)
<223> OTHER INFORMATION: Xaa is A, I, L, V or M
<220> FEATURE:
<221> NAME/KEY: MISC_FEATURE
<222> LOCATION: (82)..(82)
<223> OTHER INFORMATION: Xaa is G, A, or S
<220> FEATURE:
<221> NAME/KEY: MISC_FEATURE
<222> LOCATION: (83)..(83)
<223> OTHER INFORMATION: Xaa is D or E
<220> FEATURE:
<221> NAME/KEY: MISC_FEATURE
<222> LOCATION: (84)..(84)
<223> OTHER INFORMATION: Xaa is A, I, L, V, M, F, W, P, G, K, R, D, E,
      or H
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
```

```
<222> LOCATION: (85)..(85)
<223> OTHER INFORMATION: Xaa is A, I, L, V, M, F, W, P, G, K, R, D, E,
      or H.
<220> FEATURE:
<221> NAME/KEY: MISC_FEATURE
<222> LOCATION: (86)..(86)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(88)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (102)..(102)
<223> OTHER INFORMATION: Xaa is A, I, L, V or M
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (104)..(104)
<223> OTHER INFORMATION: Xaa is A, I, L, V or M
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (107)..(107)
<223> OTHER INFORMATION: Xaa is A, I, L, V, M, F, W, P, G. H, N, Q, Y,
      T, S, or C
<220> FEATURE:
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is G, A, or S
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (112)..(112)
<223> OTHER INFORMATION: Xaa is A, I, L, V, M, F, W, P, G. H, N, Q, Y,
      T, S, K, R, or C
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
```

```
<223> OTHER INFORMATION: Xaa is F or Y
<220> FEATURE:
<221> NAME/KEY: MISC_FEATURE
<222> LOCATION: (116)..(116)
<223> OTHER INFORMATION: Xaa is K or R
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (118)..(118)
<223> OTHER INFORMATION: Xaa is Y, W, or F
<220> FEATURE:
<221> NAME/KEY: MISC_FEATURE
<222> LOCATION: (119)..(119)
<223> OTHER INFORMATION: Xaa is Y, W, F, H, N, Q, Y, T, S, C, K or R
<220> FEATURE:
<221> NAME/KEY: MISC_FEATURE
<222> LOCATION: (120)..(120)
<223> OTHER INFORMATION: Xaa is H, N, Q, Y, T, S, or C
<220> FEATURE:
<221> NAME/KEY: MISC_FEATURE
<222> LOCATION: (121)..(121)
<223> OTHER INFORMATION: Xaa is A, I, L, V, M, F, W, P,  or G.
<220> FEATURE:
<221> NAME/KEY: MISC_FEATURE
<222> LOCATION: (122)..(122)
<223> OTHER INFORMATION: Xaa is A, I, L, V or M
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is A, I, L, V, M, F, W, P, G, H, N, Q, Y,
     T, S, C, D, or E
<220> FEATURE:
<221> NAME/KEY: MISC_FEATURE
<222> LOCATION: (125)..(125)
<223> OTHER INFORMATION: Xaa is A, I, L, V or M
<220> FEATURE:
<221> NAME/KEY: MISC_FEATURE
<222> LOCATION: (126)..(129)
<223> OTHER INFORMATION: Xaa is any amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
    115                 120                 125

Xaa

<210> SEQ ID NO 3
<211> LENGTH: 129
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is A, I, L, V, M, F, W, P, or G or absent
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is A, I, L, V, M, F, W, P, or G
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is A, I, L, V, M, F, W, P, or G
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is A, I, L, V, M, F, W, P, or G
<220> FEATURE:
<221> NAME/KEY: MISC_FEATURE
<222> LOCATION: (12)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is A, I, L, V, M, F, W, P, or G
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is G, A, or S
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, I, L, V, M, F, W, P, or G
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Y, W, F, H, N, Q, Y, T, S, or C
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (25)..(26)
<223> OTHER INFORMATION: Xaa is A, I, L, V, M, F, W, P, or G
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is A, I, L, V, M, F, W, P, or G
```

-continued

```
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is G, A, or S
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (35)..(35)
<223> OTHER INFORMATION: Xaa is A, I, L, V, M, F, W, P, or G
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(40)
<223> OTHER INFORMATION: Xaa is A, I, L, V, M, F, W, P, or G
<220> FEATURE:
<221> NAME/KEY: MISC_FEATURE
<222> LOCATION: (41)..(42)
<223> OTHER INFORMATION: Xaa is any amino acid
<220> FEATURE:
<221> NAME/KEY: MISC_FEATURE
<222> LOCATION: (43)..(43)
<223> OTHER INFORMATION: Xaa is H, N, Q, Y, T, S, or C
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is G, A, or S
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is A, I, L, V, M, F, W, P, or G
<220> FEATURE:
<221> NAME/KEY: MISC_FEATURE
<222> LOCATION: (52)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is A, I, L, V, M, F, W, P, G, H, N, Q, Y,
      T, S, C, K or R
```

```
<220> FEATURE:
<221> NAME/KEY: MISC_FEATURE
<222> LOCATION: (55)..(55)
<223> OTHER INFORMATION: Xaa is A, I, L, V, M, F, W, P, or G
<220> FEATURE:
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is A, I, L, V, M, F, W, P, G, H, N, Q, Y,
      T, S, C, K or R
<220> FEATURE:
<221> NAME/KEY: MISC_FEATURE
<222> LOCATION: (59)..(59)
<223> OTHER INFORMATION: Xaa is A, I, L, V, M, F, W, P, or G
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is A, I, L, V, M, F, W, P, or G
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is A, I, L, V, M, F, W, P, or G
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (71)..(71)
<223> OTHER INFORMATION: Xaa is A, I, L, V, M, F, W, P, or G
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is H, N, Q, Y, T, S, or C
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is A, I, L, V, M, F, W, P, or G
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, I, L, V, M, F, W, P, or G
<220> FEATURE:
<221> NAME/KEY: MISC_FEATURE
<222> LOCATION: (82)..(82)
<223> OTHER INFORMATION: Xaa is G, A, or S
<220> FEATURE:
<221> NAME/KEY: MISC_FEATURE
```

```
<222> LOCATION: (84)..(84)
<223> OTHER INFORMATION: Xaa is A, I, L, V, M, F, W, P, G, K, R, D, E,
      or H
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(88)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (107)..(107)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is G, A, or S
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (112)..(112)
<223> OTHER INFORMATION: Xaa is A, I, L, V, M, F, W, P, G, H, N, Q, Y,
      T, S, C, K or R
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
```

<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is Y, W, F, H, N, Q, Y, T, S, C, K or R
<220> FEATURE:
<221> NAME/KEY: MISC_FEATURE
<222> LOCATION: (121)..(121)
<223> OTHER INFORMATION: Xaa is A, I, L, V, M, F, W, P, or G
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is A, I, L, V, M, F, W, P, G, H, N, Q, Y, T, S, C, D or E
<220> FEATURE:
<221> NAME/KEY: MISC_FEATURE
<222> LOCATION: (125)..(125)
<223> OTHER INFORMATION: Xaa is A, I, L, V, or M
<220> FEATURE:
<221> NAME/KEY: MISC_FEATURE
<222> LOCATION: (126)..(129)
<223> OTHER INFORMATION: Xaa is any amino acid

<400> SEQUENCE: 3

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Tyr Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Tyr Xaa Xaa Xaa Xaa Xaa Xaa Xaa
65                  70                  75                  80

Ile Xaa Glu Xaa Xaa Xaa Xaa Xaa Xaa Xaa Xaa Xaa Xaa Xaa Xaa
                85                  90                  95

Xaa Xaa Xaa Xaa Xaa Ile Xaa Val Xaa Xaa Xaa Xaa Xaa Xaa Xaa
            100                 105                 110

Xaa Xaa Xaa Arg Xaa Phe Xaa Asn Xaa Leu Xaa Xaa Xaa Xaa Xaa
            115                 120                 125

Xaa

<210> SEQ ID NO 4
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H, N, Q, Y, T, S, M, or C
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is A, I, L, V, or M
<220> FEATURE:
<221> NAME/KEY: MISC_FEATURE
<222> LOCATION: (4)..(5)
<223> OTHER INFORMATION: Xaa is any amino acid
<220> FEATURE:

-continued

```
<221> NAME/KEY: MISC_FEATURE
<222> LOCATION: (6)..(7)
<223> OTHER INFORMATION: Xaa is A, I, L, V, or M
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is A, I, L, V, or M
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(14)
<223> OTHER INFORMATION: Xaa is A, I, L, V, or M
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is G, A, or S
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, I, L, V, or M
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Y, W, or F
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is A, I, L, V, or M
<220> FEATURE:
<221> NAME/KEY: MISC_FEATURE
<222> LOCATION: (26)..(26)
<223> OTHER INFORMATION: Xaa is Y, W, or F
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is A, I, L, V, M, F, W, P, or G
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is G, A, or S
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is A, I, L, V, or M
```

```
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (35)..(35)
<223> OTHER INFORMATION: Xaa is A, I, L, V, M, F, W, P, or G
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(40)
<223> OTHER INFORMATION: Xaa is A, I, L, V, P, G or M
<220> FEATURE:
<221> NAME/KEY: MISC_FEATURE
<222> LOCATION: (41)..(42)
<223> OTHER INFORMATION: Xaa is any amino acid
<220> FEATURE:
<221> NAME/KEY: MISC_FEATURE
<222> LOCATION: (43)..(43)
<223> OTHER INFORMATION: Xaa is H, N, Q, Y, T, S, or C
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is G, A, or S
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is A, I, L, V, or M
<220> FEATURE:
<221> NAME/KEY: MISC_FEATURE
<222> LOCATION: (52)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is A, I, L, V, M, F, W, P, G, H, N, Q, Y,
      T, S, C, K, or R
<220> FEATURE:
<221> NAME/KEY: MISC_FEATURE
<222> LOCATION: (55)..(55)
<223> OTHER INFORMATION: Xaa is A, I, L, V, M, F, W, P, or G
<220> FEATURE:
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is Y, W, or F
<220> FEATURE:
<221> NAME/KEY: MISC_FEATURE
<222> LOCATION: (59)..(59)
<223> OTHER INFORMATION: Xaa is A, I, L, V, M, F, W, P, or G
<220> FEATURE:
```

```
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is Y, W, or F
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is A, I, L, V, or M
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (71)..(71)
<223> OTHER INFORMATION: Xaa is Y, W, or F
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is H, N, Q, Y, T, S, or C
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is A, I, L, V, M, F, W, P, or G
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, I, L, V, or M
<220> FEATURE:
<221> NAME/KEY: MISC_FEATURE
<222> LOCATION: (82)..(82)
<223> OTHER INFORMATION: Xaa is G, A, or S
<220> FEATURE:
<221> NAME/KEY: MISC_FEATURE
<222> LOCATION: (84)..(84)
<223> OTHER INFORMATION: Xaa is Y, W, or F
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(88)
```

```
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is A, I, L, V, M, F, W, P, G, H, N, Q, Y,
      T, S, or C
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (107)..(107)
<223> OTHER INFORMATION: Xaa is H, N, Q, Y, T, S, or C
<220> FEATURE:
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is G, A, or S
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (112)..(112)
<223> OTHER INFORMATION: Xaa is A, I, L, V, or M
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is H, N, Q, Y, T, S, C, K, R, Y, W, or F
<220> FEATURE:
<221> NAME/KEY: MISC_FEATURE
<222> LOCATION: (121)..(121)
<223> OTHER INFORMATION: Xaa is A, I, L, V, M, F, W, P, or G
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is A, I, L, V, M, F, W, P, G, H, N, Q, Y,
      T, S, D, E or C
<220> FEATURE:
<221> NAME/KEY: MISC_FEATURE
<222> LOCATION: (125)..(125)
```

<223> OTHER INFORMATION: Xaa is A, I, L, V, or M
<220> FEATURE:
<221> NAME/KEY: MISC_FEATURE
<222> LOCATION: (126)..(129)
<223> OTHER INFORMATION: Xaa is any amino acid

<400> SEQUENCE: 4

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Tyr Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Tyr Xaa Xaa Xaa Xaa Xaa Xaa Xaa
65                  70                  75                  80

Ile Xaa Glu Xaa Xaa Xaa Xaa Xaa Xaa Xaa Xaa Xaa Xaa Xaa Xaa
                85                  90                  95

Xaa Xaa Xaa Xaa Xaa Ile Xaa Val Xaa Xaa Xaa Xaa Xaa Xaa Xaa
            100                 105                 110

Xaa Xaa Xaa Arg Xaa Phe Xaa Asn Xaa Leu Xaa Xaa Xaa Xaa Xaa
        115                 120                 125

Xaa

<210> SEQ ID NO 5
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is V or L
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is I or L
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE -continued

```
<222> LOCATION: (20)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is W or Y
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (26)..(26)
<223> OTHER INFORMATION: Xaa is F, T or Y
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is L or S
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is P or V
<220> FEATURE:
<221> NAME/KEY: MISC_FEATURE
<222> LOCATION: (41)..(42)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (45)..(45)
<223> OTHER INFORMATION: Xaa is F, H, T or Y
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
<222> LOCATION: (52)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is H, C, I or T
<220> FEATURE:
<221> NAME/KEY: MISC_FEATURE
<222> LOCATION: (55)..(55)
<223> OTHER INFORMATION: Xaa is M, F, or I
<220> FEATURE:
```

```
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is F, H, A, I, P, V, or W
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (84)..(84)
<223> OTHER INFORMATION: Xaa is F, A, D, Y, or W
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is F, I, L, T, or G
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(88)
<223> OTHER INFORMATION: Xaa is G, A, F, I, L or N
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is I, F, L, M, S, T, W, or Y
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is any amino acid
```

```
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is F, G, M, R or W
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is V, E, F, I, N, P, R, S, or W
<220> FEATURE:
<221> NAME/KEY: MISC_FEATURE
<222> LOCATION: (126)..(129)
<223> OTHER INFORMATION: Xaa is any amino acid

<400> SEQUENCE: 5

Met Xaa Ala Xaa Xaa Ile Xaa Xaa Xaa Xaa Leu Xaa Leu Xaa Xaa Xaa
 1               5                  10                  15

Gly Xaa Ala Xaa Xaa Xaa Xaa Xaa Leu Xaa Xaa Pro Xaa Gly Xaa Xaa
                20                  25                  30

Xaa Xaa Pro Tyr Xaa Xaa Pro Gly Xaa Xaa Thr Xaa Xaa Xaa Gly Xaa
            35                  40                  45

Xaa Xaa Ile Xaa Xaa Xaa Xaa Xaa Xaa Xaa Pro Xaa Xaa Xaa Xaa Xaa
        50                  55                  60

Xaa Phe Xaa Xaa Val Xaa Phe Tyr Xaa Thr Xaa Xaa Pro Xaa Xaa Ala
65                  70                  75                  80

Ile Gly Glu Xaa Xaa Xaa Xaa Xaa Xaa Xaa Xaa Xaa Xaa Xaa Xaa Xaa
                85                  90                  95

Xaa Xaa Xaa Xaa Xaa Ile Xaa Val Xaa Xaa Thr Xaa Xaa Gly Xaa Ile
            100                 105                 110

Xaa Xaa Xaa Arg Xaa Phe Xaa Asn Pro Leu Xaa Xaa Leu Xaa Xaa Xaa
        115                 120                 125

Xaa

<210> SEQ ID NO 6
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: optionally absent
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is V or L
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (20)..(21)
<223> OTHER INFORMATION: Xaa is any amino acid
<220> FEATURE:
<221> NAME/KEY: MISC_FEATURE
<222> LOCATION: (23)..(24)
<223> OTHER INFORMATION: Xaa is any amino acid
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (41)..(42)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (48)..(50)
<223> OTHER INFORMATION: Xaa is any amino acid
<220> FEATURE:
<221> NAME/KEY: MISC_FEATURE
```

```
<222> LOCATION: (52)..(53)
<223> OTHER INFORMATION: Xaa is any amino acid
<220> FEATURE:
<221> NAME/KEY: MISC_FEATURE
<222> LOCATION: (56)..(57)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is F or H
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is A, I, L, V, M, F, W, P, or G
<220> FEATURE:
<221> NAME/KEY: MISC_FEATURE
<222> LOCATION: (63)..(65)
<223> OTHER INFORMATION: Xaa is any amino acid
<220> FEATURE:
<221> NAME/KEY: MISC_FEATURE
<222> LOCATION: (67)..(68)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (84)..(84)
<223> OTHER INFORMATION: Xaa is F or Y
<220> FEATURE:
<221> NAME/KEY: MISC_FEATURE
<222> LOCATION: (85)..(85)
<223> OTHER INFORMATION: Xaa is any amino acid
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (89)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is L or Y
<220> FEATURE:
<221> NAME/KEY: MISC_FEATURE
<222> LOCATION: (98)..(100)
<223> OTHER INFORMATION: Xaa is any amino acid
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (105)..(106)
<223> OTHER INFORMATION: Xaa is any amino acid
<220> FEATURE:
```

```
<221> NAME/KEY: MISC_FEATURE
<222> LOCATION: (108)..(109)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (113)..(114)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (119)..(119)
<223> OTHER INFORMATION: Xaa is F or W
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is V or I
<220> FEATURE:
<221> NAME/KEY: MISC_FEATURE
<222> LOCATION: (126)..(129)
<223> OTHER INFORMATION: Xaa is any amino acid

<400> SEQUENCE: 6

Met Xaa Ala Xaa Xaa Ile Xaa Xaa Xaa Xaa Leu Xaa Leu Leu Xaa Xaa
1               5                   10                  15

Gly Xaa Ala Xaa Xaa Trp Xaa Xaa Leu Phe Xaa Pro Xaa Gly Xaa Leu
                20                  25                  30

Xaa Xaa Pro Tyr Xaa Pro Pro Gly Xaa Xaa Thr Xaa Phe Xaa Gly Xaa
            35                  40                  45

Xaa Xaa Ile Xaa Xaa His Met Xaa Xaa Xaa Pro Xaa Xaa Xaa Xaa Xaa
        50                  55                  60

Xaa Phe Xaa Xaa Val Xaa Phe Tyr Xaa Thr Xaa Xaa Pro Xaa Xaa Ala
65                  70                  75                  80

Ile Gly Glu Xaa Xaa Gly Xaa Gly Xaa Xaa Xaa Xaa Xaa Xaa Xaa Xaa
                85                  90                  95

Xaa Xaa Xaa Xaa Xaa Ile Xaa Val Xaa Xaa Thr Xaa Xaa Gly Xaa Ile
            100                 105                 110

Xaa Xaa Xaa Arg Xaa Phe Xaa Asn Pro Leu Xaa Xaa Leu Xaa Xaa Xaa
        115                 120                 125

Xaa

<210> SEQ ID NO 7
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(2)
<223> OTHER INFORMATION: Xaa is N, D, S, T, or C
```

```
<220> FEATURE:
<221> NAME/KEY: MISC_FEATURE
<222> LOCATION: (4)..(5)
<223> OTHER INFORMATION: Xaa is K, R, D, E, or H
<220> FEATURE:
<221> NAME/KEY: MISC_FEATURE
<222> LOCATION: (7)..(7)
<223> OTHER INFORMATION: Xaa is V or L
<220> FEATURE:
<221> NAME/KEY: MISC_FEATURE
<222> LOCATION: (8)..(8)
<223> OTHER INFORMATION: Xaa is A, I, L, V, M, F, W, P, G, K, R, D, E,
     or H
<220> FEATURE:
<221> NAME/KEY: MISC_FEATURE
<222> LOCATION: (9)..(9)
<223> OTHER INFORMATION: Xaa is H, N, Q, Y, T, S, C, K, R, D, E, or H
<220> FEATURE:
<221> NAME/KEY: MISC_FEATURE
<222> LOCATION: (10)..(10)
<223> OTHER INFORMATION: Xaa is A, I, L, V, M, H, N, Q, Y, T, S, or C
<220> FEATURE:
<221> NAME/KEY: MISC_FEATURE
<222> LOCATION: (12)..(12)
<223> OTHER INFORMATION: Xaa is K, R, D, E, or H
<220> FEATURE:
<221> NAME/KEY: MISC_FEATURE
<222> LOCATION: (15)..(15)
<223> OTHER INFORMATION: Xaa is K, R, D, E, or H
<220> FEATURE:
<221> NAME/KEY: MISC_FEATURE
<222> LOCATION: (16)..(16)
<223> OTHER INFORMATION: Xaa is H, N, Q, Y, T, S, or C
<220> FEATURE:
<221> NAME/KEY: MISC_FEATURE
<222> LOCATION: (18)..(18)
<223> OTHER INFORMATION: Xaa is K, R, D, E, or H
<220> FEATURE:
<221> NAME/KEY: MISC_FEATURE
<222> LOCATION: (20)..(20)
<223> OTHER INFORMATION: Xaa is K, R, D, E, or H
<220> FEATURE:
<221> NAME/KEY: MISC_FEATURE
<222> LOCATION: (21)..(21)
<223> OTHER INFORMATION: Xaa is H, N, Q, Y, T, S, or C
<220> FEATURE:
<221> NAME/KEY: MISC_FEATURE
<222> LOCATION: (23)..(23)
<223> OTHER INFORMATION: Xaa is H, N, Q, Y, T, S, or C
<220> FEATURE:
<221> NAME/KEY: MISC_FEATURE
<222> LOCATION: (24)..(24)
<223> OTHER INFORMATION: Xaa is K, R, D, E, or H
<220> FEATURE:
<221> NAME/KEY: MISC_FEATURE
<222> LOCATION: (27)..(27)
<223> OTHER INFORMATION: Xaa is H, N, Q, Y, T, S, C, K, R, D, E, or H
<220> FEATURE:
<221> NAME/KEY: MISC_FEATURE
<222> LOCATION: (29)..(29)
<223> OTHER INFORMATION: Xaa is K, R, D, E, or H
<220> FEATURE:
<221> NAME/KEY: MISC_FEATURE
<222> LOCATION: (31)..(31)
<223> OTHER INFORMATION: Xaa is A, I, L, V, M, F, W, P, G, K, R, D, E or
     H
<220> FEATURE:
<221> NAME/KEY: MISC_FEATURE
<222> LOCATION: (33)..(33)
<223> OTHER INFORMATION: Xaa is K, R, D, E, or H
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (37)..(37)
<223> OTHER INFORMATION: Xaa is A, I, L, V, M, F, W, P, G, K, R, D, E,
     N, Q, Y, T, S, C, or H
```

-continued

```
<220> FEATURE:
<221> NAME/KEY: MISC_FEATURE
<222> LOCATION: (41)..(41)
<223> OTHER INFORMATION: Xaa is A, I, L, V, M, F, W, P, G, K, or R
<220> FEATURE:
<221> NAME/KEY: MISC_FEATURE
<222> LOCATION: (42)..(42)
<223> OTHER INFORMATION: Xaa is K, R, D, E, or H
<220> FEATURE:
<221> NAME/KEY: MISC_FEATURE
<222> LOCATION: (44)..(44)
<223> OTHER INFORMATION: Xaa is K, R, D, E, or H
<220> FEATURE:
<221> NAME/KEY: MISC_FEATURE
<222> LOCATION: (46)..(46)
<223> OTHER INFORMATION: Xaa is K, R, D, E, or H
<220> FEATURE:
<221> NAME/KEY: MISC_FEATURE
<222> LOCATION: (48)..(49)
<223> OTHER INFORMATION: Xaa is K, R, D, E, or H
<220> FEATURE:
<221> NAME/KEY: MISC_FEATURE
<222> LOCATION: (50)..(50)
<223> OTHER INFORMATION: Xaa is H, N, Q, Y, T, S, or C
<220> FEATURE:
<221> NAME/KEY: MISC_FEATURE
<222> LOCATION: (52)..(52)
<223> OTHER INFORMATION: Xaa is F, Y, W, K, D, E, H or R
<220> FEATURE:
<221> NAME/KEY: MISC_FEATURE
<222> LOCATION: (53)..(53)
<223> OTHER INFORMATION: Xaa is A, I, L, V, M, K, D, E, H or R
<220> FEATURE:
<221> NAME/KEY: MISC_FEATURE
<222> LOCATION: (56)..(56)
<223> OTHER INFORMATION: Xaa is K, R, D, E, or H
<220> FEATURE:
<221> NAME/KEY: MISC_FEATURE
<222> LOCATION: (57)..(57)
<223> OTHER INFORMATION: Xaa is A, I, L, V, M, K, D, E, H or R
<220> FEATURE:
<221> NAME/KEY: MISC_FEATURE
<222> LOCATION: (58)..(58)
<223> OTHER INFORMATION: Xaa is F or H
<220> FEATURE:
<221> NAME/KEY: MISC_FEATURE
<222> LOCATION: (60)..(60)
<223> OTHER INFORMATION: Xaa is K, R, D, E, or H
<220> FEATURE:
<221> NAME/KEY: MISC_FEATURE
<222> LOCATION: (61)..(61)
<223> OTHER INFORMATION: Xaa is Y, W or F
<220> FEATURE:
<221> NAME/KEY: MISC_FEATURE
<222> LOCATION: (62)..(62)
<223> OTHER INFORMATION: Xaa is A, I, L, V, M, F, W, P, W or G
<220> FEATURE:
<221> NAME/KEY: MISC_FEATURE
<222> LOCATION: (63)..(63)
<223> OTHER INFORMATION: Xaa is H, N, Q, Y, T, S, or C
<220> FEATURE:
<221> NAME/KEY: MISC_FEATURE
<222> LOCATION: (64)..(64)
<223> OTHER INFORMATION: Xaa is A, I, L, V, M, F, W, P, or G
<220> FEATURE:
<221> NAME/KEY: MISC_FEATURE
<222> LOCATION: (65)..(65)
<223> OTHER INFORMATION: Xaa is K, R, D, E, or H
<220> FEATURE:
<221> NAME/KEY: MISC_FEATURE
<222> LOCATION: (67)..(67)
<223> OTHER INFORMATION: Xaa is H, N, Q, Y, T, S, or C
<220> FEATURE:
<221> NAME/KEY: MISC_FEATURE
<222> LOCATION: (68)..(68)
<223> OTHER INFORMATION: Xaa is K, R, D, E, or H
<220> FEATURE:
<221> NAME/KEY: MISC_FEATURE
<222> LOCATION: (70)..(70)
```

```
<223> OTHER INFORMATION: Xaa is H, N, Q, Y, T, S, or C
<220> FEATURE:
<221> NAME/KEY: MISC_FEATURE
<222> LOCATION: (73)..(73)
<223> OTHER INFORMATION: Xaa is K, R, D, E, or H
<220> FEATURE:
<221> NAME/KEY: MISC_FEATURE
<222> LOCATION: (75)..(75)
<223> OTHER INFORMATION: Xaa is A, I, L, V, or M
<220> FEATURE:
<221> NAME/KEY: MISC_FEATURE
<222> LOCATION: (76)..(76)
<223> OTHER INFORMATION: Xaa is K, R, D, E, or H
<220> FEATURE:
<221> NAME/KEY: MISC_FEATURE
<222> LOCATION: (78)..(78)
<223> OTHER INFORMATION: Xaa is K, R, D, E, or H
<220> FEATURE:
<221> NAME/KEY: MISC_FEATURE
<222> LOCATION: (79)..(79)
<223> OTHER INFORMATION: Xaa is A, I, L, V, or M
<220> FEATURE:
<221> NAME/KEY: MISC_FEATURE
<222> LOCATION: (84)..(84)
<223> OTHER INFORMATION: Xaa is F or Y
<220> FEATURE:
<221> NAME/KEY: MISC_FEATURE
<222> LOCATION: (85)..(85)
<223> OTHER INFORMATION: Xaa is H, N, Q, Y, T, S, or C
<220> FEATURE:
<221> NAME/KEY: MISC_FEATURE
<222> LOCATION: (87)..(87)
<223> OTHER INFORMATION: Xaa is K, R, D, E, or H
<220> FEATURE:
<221> NAME/KEY: MISC_FEATURE
<222> LOCATION: (89)..(89)
<223> OTHER INFORMATION: Xaa is A, I, L, V, M, K, D, E, H or R
<220> FEATURE:
<221> NAME/KEY: MISC_FEATURE
<222> LOCATION: (90)..(90)
<223> OTHER INFORMATION: Xaa is H, l, A, C, F, I, Q, R, S, T, V, or Y
<220> FEATURE:
<221> NAME/KEY: MISC_FEATURE
<222> LOCATION: (91)..(91)
<223> OTHER INFORMATION: Xaa is K, R, D, E,  H, N, Q, Y, T, S, or C
<220> FEATURE:
<221> NAME/KEY: MISC_FEATURE
<222> LOCATION: (92)..(92)
<223> OTHER INFORMATION: Xaa is V, A, D, E, F, G, I, K, L, M, P, Q, R,
     S, T, or W
<220> FEATURE:
<221> NAME/KEY: MISC_FEATURE
<222> LOCATION: (93)..(93)
<223> OTHER INFORMATION: Xaa is K, R, H, N, Q, Y, T, S, or C
<220> FEATURE:
<221> NAME/KEY: MISC_FEATURE
<222> LOCATION: (94)..(94)
<223> OTHER INFORMATION: Xaa is G, A, or S
<220> FEATURE:
<221> NAME/KEY: MISC_FEATURE
<222> LOCATION: (95)..(95)
<223> OTHER INFORMATION: Xaa is D, E, Y, W, F, H, N, Q, Y, T, S, or C
<220> FEATURE:
<221> NAME/KEY: MISC_FEATURE
<222> LOCATION: (96)..(96)
<223> OTHER INFORMATION: Xaa is K, R, D, E, or H
<220> FEATURE:
<221> NAME/KEY: MISC_FEATURE
<222> LOCATION: (97)..(97)
<223> OTHER INFORMATION: Xaa is L or Y
<220> FEATURE:
<221> NAME/KEY: MISC_FEATURE
<222> LOCATION: (98)..(98)
<223> OTHER INFORMATION: Xaa is A, I, L, V, or M
<220> FEATURE:
<221> NAME/KEY: MISC_FEATURE
<222> LOCATION: (99)..(99)
<223> OTHER INFORMATION: Xaa is A, I, L, V, M, F, W, P, G, H, N, Q, Y,
     T, S or C
```

```
<220> FEATURE:
<221> NAME/KEY: MISC_FEATURE
<222> LOCATION: (100)..(100)
<223> OTHER INFORMATION: Xaa is K, R, D, E, or H
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is S, A, C, D, L, N, R, T, V or W
<220> FEATURE:
<221> NAME/KEY: MISC_FEATURE
<222> LOCATION: (105)..(105)
<223> OTHER INFORMATION: Xaa is L, W, A, F, I, K, M, S, T, or V
<220> FEATURE:
<221> NAME/KEY: MISC_FEATURE
<222> LOCATION: (106)..(106)
<223> OTHER INFORMATION: Xaa is K, R, D, E, or H
<220> FEATURE:
<221> NAME/KEY: MISC_FEATURE
<222> LOCATION: (108)..(109)
<223> OTHER INFORMATION: Xaa is K, R, D, E, or H
<220> FEATURE:
<221> NAME/KEY: MISC_FEATURE
<222> LOCATION: (111)..(111)
<223> OTHER INFORMATION: Xaa is H, N, Q, Y, T, S, or C
<220> FEATURE:
<221> NAME/KEY: MISC_FEATURE
<222> LOCATION: (113)..(114)
<223> OTHER INFORMATION: Xaa is A, I, L, V, M, K, D, E, H or R
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is V, L, A, D, G, M, N, S, or Y
<220> FEATURE:
<221> NAME/KEY: MISC_FEATURE
<222> LOCATION: (119)..(119)
<223> OTHER INFORMATION: Xaa is F or W
<220> FEATURE:
<221> NAME/KEY: MISC_FEATURE
<222> LOCATION: (123)..(123)
<223> OTHER INFORMATION: Xaa is K, R, D, E, or H
<220> FEATURE:
<221> NAME/KEY: MISC_FEATURE
<222> LOCATION: (124)..(124)
<223> OTHER INFORMATION: Xaa is V or I
<220> FEATURE:
<221> NAME/KEY: MISC_FEATURE
<222> LOCATION: (126)..(126)
<223> OTHER INFORMATION: Xaa is K, R, D, E, or H
<220> FEATURE:
<221> NAME/KEY: MISC_FEATURE
<222> LOCATION: (127)..(127)
<223> OTHER INFORMATION: Xaa is A, I, L, V, M, H, N, Q, Y, T, S, or C
<220> FEATURE:
<221> NAME/KEY: MISC_FEATURE
<222> LOCATION: (128)..(128)
<223> OTHER INFORMATION: Xaa is L, E, G, H, I, K, P, Q, R, T, V or A
<220> FEATURE:
<221> NAME/KEY: MISC_FEATURE
<222> LOCATION: (129)..(129)
<223> OTHER INFORMATION: Xaa is G, A, or S

<400> SEQUENCE: 7

Met Xaa Ala Xaa Xaa Ile Xaa Xaa Xaa Leu Xaa Leu Leu Xaa Xaa
1               5                   10                  15

Gly Xaa Ala Xaa Xaa Trp Xaa Xaa Leu Phe Xaa Pro Xaa Gly Xaa Leu
            20                  25                  30

Xaa Xaa Pro Tyr Xaa Pro Pro Gly Xaa Xaa Thr Xaa Phe Xaa Gly Xaa
        35                  40                  45
```

```
Xaa Xaa Ile Xaa Xaa His Met Xaa Xaa Xaa Pro Xaa Xaa Xaa Xaa
     50                  55                  60

Xaa Phe Xaa Xaa Val Xaa Phe Tyr Xaa Thr Xaa Xaa Pro Xaa Xaa Ala
 65                  70                  75                  80

Ile Gly Glu Xaa Xaa Gly Xaa Gly Xaa Xaa Xaa Xaa Xaa Xaa Xaa
                 85                  90                  95

Xaa Xaa Xaa Xaa Xaa Ile Xaa Val Xaa Xaa Thr Xaa Xaa Gly Xaa Ile
             100                 105                 110

Xaa Xaa Xaa Arg Xaa Phe Xaa Asn Pro Leu Xaa Xaa Leu Xaa Xaa Xaa
         115                 120                 125

Xaa

<210> SEQ ID NO 8
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (4)..(5)
<223> OTHER INFORMATION: Xaa is K or C
<220> FEATURE:
<221> NAME/KEY: MISC_FEATURE
<222> LOCATION: (7)..(7)
<223> OTHER INFORMATION: Xaa is V or L
<220> FEATURE:
<221> NAME/KEY: MISC_FEATURE
<222> LOCATION: (8)..(8)
<223> OTHER INFORMATION: Xaa is V or C
<220> FEATURE:
<221> NAME/KEY: MISC_FEATURE
<222> LOCATION: (9)..(9)
<223> OTHER INFORMATION: Xaa is H or C
<220> FEATURE:
<221> NAME/KEY: MISC_FEATURE
<222> LOCATION: (10)..(10)
<223> OTHER INFORMATION: Xaa is S or A
<220> FEATURE:
<221> NAME/KEY: MISC_FEATURE
<222> LOCATION: (12)..(12)
<223> OTHER INFORMATION: Xaa is R or C
<220> FEATURE:
<221> NAME/KEY: MISC_FEATURE
<222> LOCATION: (15)..(15)
<223> OTHER INFORMATION: Xaa is E or C
<220> FEATURE:
<221> NAME/KEY: MISC_FEATURE
<222> LOCATION: (16)..(16)
<223> OTHER INFORMATION: Xaa is N or C
<220> FEATURE:
<221> NAME/KEY: MISC_FEATURE
<222> LOCATION: (18)..(18)
<223> OTHER INFORMATION: Xaa is D or C
<220> FEATURE:
<221> NAME/KEY: MISC_FEATURE
<222> LOCATION: (20)..(20)
<223> OTHER INFORMATION: Xaa is R or C
<220> FEATURE:
<221> NAME/KEY: MISC_FEATURE
<222> LOCATION: (21)..(21)
<223> OTHER INFORMATION: Xaa is G or C
<220> FEATURE:
<221> NAME/KEY: MISC_FEATURE
<222> LOCATION: (23)..(23)
<223> OTHER INFORMATION: Xaa is C, S, T or A
<220> FEATURE:
<221> NAME/KEY: MISC_FEATURE
```

```
<222> LOCATION: (24)..(24)
<223> OTHER INFORMATION: Xaa is D or C
<220> FEATURE:
<221> NAME/KEY: MISC_FEATURE
<222> LOCATION: (27)..(27)
<223> OTHER INFORMATION: Xaa is H or C
<220> FEATURE:
<221> NAME/KEY: MISC_FEATURE
<222> LOCATION: (29)..(29)
<223> OTHER INFORMATION: Xaa is E or C
<220> FEATURE:
<221> NAME/KEY: MISC_FEATURE
<222> LOCATION: (31)..(31)
<223> OTHER INFORMATION: Xaa is V or C
<220> FEATURE:
<221> NAME/KEY: MISC_FEATURE
<222> LOCATION: (33)..(33)
<223> OTHER INFORMATION: Xaa is E or C
<220> FEATURE:
<221> NAME/KEY: MISC_FEATURE
<222> LOCATION: (34)..(34)
<223> OTHER INFORMATION: Xaa is F or Y
<220> FEATURE:
<221> NAME/KEY: MISC_FEATURE
<222> LOCATION: (37)..(37)
<223> OTHER INFORMATION: Xaa is A, P, E, K, P, Q, R or T
<220> FEATURE:
<221> NAME/KEY: MISC_FEATURE
<222> LOCATION: (41)..(41)
<223> OTHER INFORMATION: Xaa is H, Y, F, K, L, T, V or W
<220> FEATURE:
<221> NAME/KEY: MISC_FEATURE
<222> LOCATION: (42)..(42)
<223> OTHER INFORMATION: Xaa is K or C
<220> FEATURE:
<221> NAME/KEY: MISC_FEATURE
<222> LOCATION: (44)..(44)
<223> OTHER INFORMATION: Xaa is R or C
<220> FEATURE:
<221> NAME/KEY: MISC_FEATURE
<222> LOCATION: (46)..(46)
<223> OTHER INFORMATION: Xaa is E or C
<220> FEATURE:
<221> NAME/KEY: MISC_FEATURE
<222> LOCATION: (48)..(48)
<223> OTHER INFORMATION: Xaa is R or C
<220> FEATURE:
<221> NAME/KEY: MISC_FEATURE
<222> LOCATION: (49)..(49)
<223> OTHER INFORMATION: Xaa is E or C
<220> FEATURE:
<221> NAME/KEY: MISC_FEATURE
<222> LOCATION: (50)..(50)
<223> OTHER INFORMATION: Xaa is T or C
<220> FEATURE:
<221> NAME/KEY: MISC_FEATURE
<222> LOCATION: (52)..(52)
<223> OTHER INFORMATION: Xaa is W or C
<220> FEATURE:
<221> NAME/KEY: MISC_FEATURE
<222> LOCATION: (53)..(53)
<223> OTHER INFORMATION: Xaa is A or C
<220> FEATURE:
<221> NAME/KEY: MISC_FEATURE
<222> LOCATION: (56)..(56)
<223> OTHER INFORMATION: Xaa is R or C
<220> FEATURE:
<221> NAME/KEY: MISC_FEATURE
<222> LOCATION: (57)..(57)
<223> OTHER INFORMATION: Xaa is L or C
<220> FEATURE:
<221> NAME/KEY: MISC_FEATURE
<222> LOCATION: (58)..(58)
<223> OTHER INFORMATION: Xaa is F or H
<220> FEATURE:
<221> NAME/KEY: MISC_FEATURE
<222> LOCATION: (60)..(60)
<223> OTHER INFORMATION: Xaa is E or C
<220> FEATURE:
```

```
<221> NAME/KEY: MISC_FEATURE
<222> LOCATION: (61)..(61)
<223> OTHER INFORMATION: Xaa is Y, H, R or W
<220> FEATURE:
<221> NAME/KEY: MISC_FEATURE
<222> LOCATION: (62)..(62)
<223> OTHER INFORMATION: Xaa is V or M
<220> FEATURE:
<221> NAME/KEY: MISC_FEATURE
<222> LOCATION: (63)..(63)
<223> OTHER INFORMATION: Xaa is T or C
<220> FEATURE:
<221> NAME/KEY: MISC_FEATURE
<222> LOCATION: (64)..(64)
<223> OTHER INFORMATION: Xaa is V, I, G, K, P or W
<220> FEATURE:
<221> NAME/KEY: MISC_FEATURE
<222> LOCATION: (65)..(65)
<223> OTHER INFORMATION: Xaa is R or C
<220> FEATURE:
<221> NAME/KEY: MISC_FEATURE
<222> LOCATION: (67)..(67)
<223> OTHER INFORMATION: Xaa is T or C
<220> FEATURE:
<221> NAME/KEY: MISC_FEATURE
<222> LOCATION: (68)..(68)
<223> OTHER INFORMATION: Xaa is D or C
<220> FEATURE:
<221> NAME/KEY: MISC_FEATURE
<222> LOCATION: (70)..(70)
<223> OTHER INFORMATION: Xaa is Q or C
<220> FEATURE:
<221> NAME/KEY: MISC_FEATURE
<222> LOCATION: (73)..(73)
<223> OTHER INFORMATION: Xaa is E or C
<220> FEATURE:
<221> NAME/KEY: MISC_FEATURE
<222> LOCATION: (75)..(75)
<223> OTHER INFORMATION: Xaa is A or C
<220> FEATURE:
<221> NAME/KEY: MISC_FEATURE
<222> LOCATION: (76)..(76)
<223> OTHER INFORMATION: Xaa is D or C
<220> FEATURE:
<221> NAME/KEY: MISC_FEATURE
<222> LOCATION: (78)..(78)
<223> OTHER INFORMATION: Xaa is D or C
<220> FEATURE:
<221> NAME/KEY: MISC_FEATURE
<222> LOCATION: (79)..(79)
<223> OTHER INFORMATION: Xaa is L or C
<220> FEATURE:
<221> NAME/KEY: MISC_FEATURE
<222> LOCATION: (84)..(84)
<223> OTHER INFORMATION: Xaa is F or Y
<220> FEATURE:
<221> NAME/KEY: MISC_FEATURE
<222> LOCATION: (85)..(85)
<223> OTHER INFORMATION: Xaa is H or C
<220> FEATURE:
<221> NAME/KEY: MISC_FEATURE
<222> LOCATION: (87)..(87)
<223> OTHER INFORMATION: Xaa is D or C
<220> FEATURE:
<221> NAME/KEY: MISC_FEATURE
<222> LOCATION: (89)..(89)
<223> OTHER INFORMATION: Xaa is V or C
<220> FEATURE:
<221> NAME/KEY: MISC_FEATURE
<222> LOCATION: (90)..(90)
<223> OTHER INFORMATION: Xaa is H, L, A, C, F, I, Q, R, S, T, V or Y
<220> FEATURE:
<221> NAME/KEY: MISC_FEATURE
<222> LOCATION: (91)..(91)
<223> OTHER INFORMATION: Xaa is T or C
<220> FEATURE:
<221> NAME/KEY: MISC_FEATURE
<222> LOCATION: (92)..(92)
<223> OTHER INFORMATION: Xaa is V, A, D, E, F, G, I, K, L, M, P, Q, R,
```

-continued

```
                S, T or W
<220> FEATURE:
<221> NAME/KEY: MISC_FEATURE
<222> LOCATION: (93)..(93)
<223> OTHER INFORMATION: Xaa is S, H, or C
<220> FEATURE:
<221> NAME/KEY: MISC_FEATURE
<222> LOCATION: (94)..(94)
<223> OTHER INFORMATION: Xaa is G or C
<220> FEATURE:
<221> NAME/KEY: MISC_FEATURE
<222> LOCATION: (95)..(95)
<223> OTHER INFORMATION: Xaa is G, E, W, Y or C
<220> FEATURE:
<221> NAME/KEY: MISC_FEATURE
<222> LOCATION: (96)..(96)
<223> OTHER INFORMATION: Xaa is K or C
<220> FEATURE:
<221> NAME/KEY: MISC_FEATURE
<222> LOCATION: (97)..(97)
<223> OTHER INFORMATION: Xaa is L or Y
<220> FEATURE:
<221> NAME/KEY: MISC_FEATURE
<222> LOCATION: (98)..(98)
<223> OTHER INFORMATION: Xaa is A or C
<220> FEATURE:
<221> NAME/KEY: MISC_FEATURE
<222> LOCATION: (99)..(99)
<223> OTHER INFORMATION: Xaa is A, Y, C, F, G, I, L, N, T or V
<220> FEATURE:
<221> NAME/KEY: MISC_FEATURE
<222> LOCATION: (100)..(100)
<223> OTHER INFORMATION: Xaa is D or C
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is S, A, D, L, N, R, T, V, W or C
<220> FEATURE:
<221> NAME/KEY: MISC_FEATURE
<222> LOCATION: (105)..(105)
<223> OTHER INFORMATION: Xaa is L, W, A, F, I, K, M, S, T or V
<220> FEATURE:
<221> NAME/KEY: MISC_FEATURE
<222> LOCATION: (106)..(106)
<223> OTHER INFORMATION: Xaa is R or C
<220> FEATURE:
<221> NAME/KEY: MISC_FEATURE
<222> LOCATION: (108)..(108)
<223> OTHER INFORMATION: Xaa is R or C
<220> FEATURE:
<221> NAME/KEY: MISC_FEATURE
<222> LOCATION: (109)..(109)
<223> OTHER INFORMATION: Xaa is D or C
<220> FEATURE:
<221> NAME/KEY: MISC_FEATURE
<222> LOCATION: (111)..(111)
<223> OTHER INFORMATION: Xaa is Q or C
<220> FEATURE:
<221> NAME/KEY: MISC_FEATURE
<222> LOCATION: (113)..(113)
<223> OTHER INFORMATION: Xaa is L or C
<220> FEATURE:
<221> NAME/KEY: MISC_FEATURE
<222> LOCATION: (114)..(114)
<223> OTHER INFORMATION: Xaa is L or C
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is L, V, A, D, G, M, N, S or Y
<220> FEATURE:
<221> NAME/KEY: MISC_FEATURE
```

```
<222> LOCATION: (119)..(119)
<223> OTHER INFORMATION: Xaa is F or W
<220> FEATURE:
<221> NAME/KEY: MISC_FEATURE
<222> LOCATION: (123)..(123)
<223> OTHER INFORMATION: Xaa is R or C
<220> FEATURE:
<221> NAME/KEY: MISC_FEATURE
<222> LOCATION: (124)..(124)
<223> OTHER INFORMATION: Xaa is V or I
<220> FEATURE:
<221> NAME/KEY: MISC_FEATURE
<222> LOCATION: (126)..(126)
<223> OTHER INFORMATION: Xaa is E or C
<220> FEATURE:
<221> NAME/KEY: MISC_FEATURE
<222> LOCATION: (127)..(127)
<223> OTHER INFORMATION: Xaa is a, P, H, I, L, S or V
<220> FEATURE:
<221> NAME/KEY: MISC_FEATURE
<222> LOCATION: (128)..(128)
<223> OTHER INFORMATION: Xaa is L, E, G, H, I, K, P, Q, R, T, V, C or A
<220> FEATURE:
<221> NAME/KEY: MISC_FEATURE
<222> LOCATION: (129)..(129)
<223> OTHER INFORMATION: Xaa is G or C

<400> SEQUENCE: 8

Met Asn Ala Xaa Xaa Ile Xaa Xaa Xaa Xaa Leu Xaa Leu Leu Xaa Xaa
1               5                   10                  15

Gly Xaa Ala Xaa Xaa Trp Xaa Xaa Leu Phe Xaa Pro Xaa Gly Xaa Leu
                20                  25                  30

Xaa Xaa Pro Tyr Xaa Pro Pro Gly Xaa Xaa Thr Xaa Phe Xaa Gly Xaa
            35                  40                  45

Xaa Xaa Ile Xaa Xaa His Met Xaa Xaa Xaa Pro Xaa Xaa Xaa Xaa Xaa
        50                  55                  60

Xaa Phe Xaa Xaa Val Xaa Phe Tyr Xaa Thr Xaa Xaa Pro Xaa Xaa Ala
65                  70                  75                  80

Ile Gly Glu Xaa Xaa Gly Xaa Gly Xaa Xaa Xaa Xaa Xaa Xaa Xaa Xaa
                85                  90                  95

Xaa Xaa Xaa Xaa Xaa Ile Xaa Val Xaa Xaa Thr Xaa Xaa Gly Xaa Ile
            100                 105                 110

Xaa Xaa Xaa Arg Xaa Phe Xaa Asn Pro Leu Xaa Xaa Leu Xaa Xaa Xaa
        115                 120                 125

Xaa

<210> SEQ ID NO 9
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (7)..(7)
<223> OTHER INFORMATION: Xaa is V or L
<220> FEATURE:
<221> NAME/KEY: MISC_FEATURE
<222> LOCATION: (23)..(23)
<223> OTHER INFORMATION: Xaa is C or S
<220> FEATURE:
<221> NAME/KEY: MISC_FEATURE
<222> LOCATION: (34)..(34)
<223> OTHER INFORMATION: Xaa is F or Y
<220> FEATURE:
```

```
<221> NAME/KEY: MISC_FEATURE
<222> LOCATION: (37)..(37)
<223> OTHER INFORMATION: Xaa is A or P
<220> FEATURE:
<221> NAME/KEY: MISC_FEATURE
<222> LOCATION: (41)..(41)
<223> OTHER INFORMATION: Xaa is H, Y or W
<220> FEATURE:
<221> NAME/KEY: MISC_FEATURE
<222> LOCATION: (58)..(58)
<223> OTHER INFORMATION: Xaa is F or H
<220> FEATURE:
<221> NAME/KEY: MISC_FEATURE
<222> LOCATION: (61)..(61)
<223> OTHER INFORMATION: Xaa is H or Y
<220> FEATURE:
<221> NAME/KEY: MISC_FEATURE
<222> LOCATION: (62)..(62)
<223> OTHER INFORMATION: Xaa is V or M
<220> FEATURE:
<221> NAME/KEY: MISC_FEATURE
<222> LOCATION: (64)..(64)
<223> OTHER INFORMATION: Xaa is V, I or W
<220> FEATURE:
<221> NAME/KEY: MISC_FEATURE
<222> LOCATION: (84)..(84)
<223> OTHER INFORMATION: Xaa is F or Y
<220> FEATURE:
<221> NAME/KEY: MISC_FEATURE
<222> LOCATION: (90)..(90)
<223> OTHER INFORMATION: Xaa is H, L or V
<220> FEATURE:
<221> NAME/KEY: MISC_FEATURE
<222> LOCATION: (91)..(91)
<223> OTHER INFORMATION: Xaa is T or C
<220> FEATURE:
<221> NAME/KEY: MISC_FEATURE
<222> LOCATION: (92)..(92)
<223> OTHER INFORMATION: Xaa is V or A
<220> FEATURE:
<221> NAME/KEY: MISC_FEATURE
<222> LOCATION: (97)..(97)
<223> OTHER INFORMATION: Xaa is L or Y
<220> FEATURE:
<221> NAME/KEY: MISC_FEATURE
<222> LOCATION: (99)..(99)
<223> OTHER INFORMATION: Xaa is Y or A
<220> FEATURE:
<221> NAME/KEY: MISC_FEATURE
<222> LOCATION: (101)..(101)
<223> OTHER INFORMATION: Xaa is F or Y
<220> FEATURE:
<221> NAME/KEY: MISC_FEATURE
<222> LOCATION: (103)..(103)
<223> OTHER INFORMATION: Xaa is S, T or A
<220> FEATURE:
<221> NAME/KEY: MISC_FEATURE
<222> LOCATION: (105)..(105)
<223> OTHER INFORMATION: Xaa is L or W
<220> FEATURE:
<221> NAME/KEY: MISC_FEATURE
<222> LOCATION: (115)..(115)
<223> OTHER INFORMATION: Xaa is F or Y
<220> FEATURE:
<221> NAME/KEY: MISC_FEATURE
<222> LOCATION: (117)..(117)
<223> OTHER INFORMATION: Xaa is L or V
<220> FEATURE:
<221> NAME/KEY: MISC_FEATURE
<222> LOCATION: (119)..(119)
<223> OTHER INFORMATION: Xaa is F or W
<220> FEATURE:
<221> NAME/KEY: MISC_FEATURE
<222> LOCATION: (124)..(124)
<223> OTHER INFORMATION: Xaa is V or I
<220> FEATURE:
<221> NAME/KEY: MISC_FEATURE
<222> LOCATION: (127)..(127)
<223> OTHER INFORMATION: Xaa is A or P
```

```
<220> FEATURE:
<221> NAME/KEY: MISC_FEATURE
<222> LOCATION: (128)..(128)
<223> OTHER INFORMATION: Xaa is A or L

<400> SEQUENCE: 9
```

Met Asn Ala Lys Lys Ile Xaa Val His Ser Leu Arg Leu Leu Glu Asn
1               5                   10                  15

Gly Asp Ala Arg Gly Trp Xaa Asp Leu Phe His Pro Glu Gly Val Leu
            20                  25                  30

Glu Xaa Pro Tyr Xaa Pro Pro Gly Xaa Lys Thr Arg Phe Glu Gly Arg
        35                  40                  45

Glu Thr Ile Trp Ala His Met Arg Leu Xaa Pro Glu Xaa Xaa Thr Xaa
50                      55                  60

Arg Phe Thr Asp Val Gln Phe Tyr Glu Thr Ala Asp Pro Asp Leu Ala
65                  70                  75                  80

Ile Gly Glu Xaa His Gly Asp Gly Val Xaa Xaa Xaa Ser Gly Gly Lys
                85                  90                  95

Xaa Ala Xaa Asp Xaa Ile Xaa Val Xaa Arg Thr Arg Asp Gly Gln Ile
            100                 105                 110

Leu Leu Xaa Arg Xaa Phe Xaa Asn Pro Leu Arg Xaa Leu Glu Xaa Xaa
            115                 120                 125

Gly

```
<210> SEQ ID NO 10
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 10
```

Met Asn Ala Lys Glu Ile Leu Val His Ser Leu Arg Leu Leu Glu Asn
1               5                   10                  15

Gly Asp Ala Arg Gly Trp Cys Asp Leu Phe His Pro Glu Gly Val Leu
            20                  25                  30

Glu Phe Pro Tyr Ala Pro Pro Gly Trp Lys Thr Arg Phe Glu Gly Arg
        35                  40                  45

Glu Thr Ile Trp Ala His Met Arg Leu His Pro Glu His Val Thr Val
50                  55                      60

Arg Phe Thr Asp Val Gln Phe Tyr Glu Thr Ala Asp Pro Asp Leu Ala
65                  70                  75                  80

Ile Gly Glu Tyr His Gly Asp Gly Val Val Thr Val Ser Gly Gly Lys
                85                  90                  95

Tyr Ala Ala Asp Phe Ile Thr Val Leu Arg Thr Arg Asp Gly Gln Ile
            100                 105                 110

Leu Leu Tyr Arg Val Phe Trp Asn Pro Leu Arg Ala Leu Glu Ala Ala
            115                 120                 125

Gly Gly Val Glu Ala Ala Ala Lys Ile Val Gln Gly Ala
        130                 135                 140

```
<210> SEQ ID NO 11
<211> LENGTH: 141
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 11

Met Asn Ala Lys Glu Ile Leu Val His Ser Leu Arg Leu Leu Glu Asn
1               5                   10                  15

Gly Asp Ala Arg Gly Trp Cys Asp Leu Phe His Pro Glu Gly Val Leu
            20                  25                  30

Glu Tyr Pro Tyr Ala Pro Pro Gly Trp Lys Thr Arg Phe Glu Gly Arg
        35                  40                  45

Glu Thr Ile Trp Ala His Met Arg Leu His Pro Glu His Val Thr Trp
    50                  55                  60

Arg Phe Thr Asp Val Gln Phe Tyr Glu Thr Ala Asp Pro Asp Leu Ala
65                  70                  75                  80

Ile Gly Glu Tyr His Gly Asp Gly Val Val Thr Val Ser Gly Gly Lys
                85                  90                  95

Tyr Ala Ala Asp Tyr Ile Thr Val Leu Arg Thr Arg Asp Gly Gln Ile
            100                 105                 110

Leu Leu Leu Arg Val Phe Trp Asn Pro Leu Arg Ile Leu Glu Ala Ala
        115                 120                 125

Gly Gly Val Glu Ala Ala Ala Lys Ile Val Gln Gly Ala
    130                 135                 140

<210> SEQ ID NO 12
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 12

Met Asn Ala Lys Glu Ile Val Val His Ser Leu Arg Leu Leu Glu Asn
1               5                   10                  15

Gly Asp Ala Arg Gly Trp Cys Asp Leu Phe His Pro Glu Gly Val Leu
            20                  25                  30

Glu Tyr Pro Tyr Ala Pro Pro Gly His Lys Thr Arg Phe Glu Gly Arg
        35                  40                  45

Glu Thr Ile Trp Ala His Met Arg Leu Phe Pro Glu Tyr Val Thr Val
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val His Thr Val Ser Gly Gly Lys
                85                  90                  95

Leu Ala Ala Asp Tyr Ile Ser Val Leu Arg Thr Arg Asp Gly Gln Ile
            100                 105                 110

Leu Leu Tyr Arg Val Phe Phe Asn Pro Leu Arg Val Leu Glu Ala Leu
        115                 120                 125

Gly Gly Val Glu Ala Ala Ala Lys Ile Val Gln Gly Ala
    130                 135                 140

<210> SEQ ID NO 13
```

<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 13

Met Asn Ala Lys Glu Ile Val Val His Ala Leu Arg Leu Leu Glu Asn
1               5                   10                  15

Gly Asp Ala Arg Gly Trp Cys Asp Leu Phe His Pro Glu Gly Val Leu
            20                  25                  30

Glu Tyr Pro Tyr Ala Pro Pro Gly His Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val His Thr Val Ser Gly Gly Lys
                85                  90                  95

Leu Ala Ala Asp Tyr Ile Ser Val Leu Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 14
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 14

Met Asn Ala Lys Glu Ile Val Val His Ala Leu Arg Leu Leu Glu Asn
1               5                   10                  15

Gly Asp Ala Arg Gly Trp Cys Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val His Thr Val Ser Gly Gly Lys
                85                  90                  95

Leu Ala Ala Asp Tyr Ile Ser Val Leu Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

```
<210> SEQ ID NO 15
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 15

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Tyr Asp Tyr Ile Ala Val Trp Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 16
<211> LENGTH: 129
<212> TYPE: PRT
<213> ORGANISM: Artificial Sequence
<220> FEATURE:
<223> OTHER INFORMATION: Synthetic

<400> SEQUENCE: 16

Met Asn Ala Lys Glu Ile Val Val His Ala Leu Arg Leu Leu Glu Asn
1               5                   10                  15

Gly Asp Ala Arg Gly Trp Cys Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val His Thr Val Ser Gly Gly Lys
                85                  90                  95

Leu Ala Ala Asp Tyr Ile Ser Val Leu Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly
```

<210> SEQ ID NO 17
<211> LENGTH: 129
<212> TYPE: PRT
<213> ORGANISM: Artificial Sequence
<220> FEATURE:
<223> OTHER INFORMATION: Synthetic

<400> SEQUENCE: 17

```
Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Tyr Asp Tyr Ile Ala Val Trp Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly
```

<210> SEQ ID NO 18
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 18

```
Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Phe Asp Tyr Ile Ala Val Trp Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140
```

<210> SEQ ID NO 19
<211> LENGTH: 141

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 19

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Tyr Asp Phe Ile Ala Val Trp Arg Thr Arg Asp Gly Gln Ile
            100                 105                 110

Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 20
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 20

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Tyr Asp Tyr Ile Ala Val Trp Arg Thr Arg Asp Gly Gln Ile
            100                 105                 110

Leu Leu Phe Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140
```

<210> SEQ ID NO 21
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 21

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Tyr Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Phe Asp Phe Ile Ala Val Trp Arg Thr Arg Asp Gly Gln Ile
            100                 105                 110

Leu Leu Tyr Arg Leu Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 22
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 22

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Phe Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Phe Asp Phe Ile Ala Val Trp Arg Thr Arg Asp Gly Gln Ile
            100                 105                 110

-continued

```
Leu Leu Tyr Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 23
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (130)..(141)
<223> OTHER INFORMATION: amino acids are optionally absent

<400> SEQUENCE: 23

Met Asn Ala Lys Glu Ile Val Val His Ala Leu Arg Leu Leu Glu Asn
1               5                   10                  15

Gly Asp Ala Arg Gly Trp Ser Asp Leu Phe His Pro Glu Gly Val Leu
            20                  25                  30

Glu Phe Pro Tyr Pro Pro Gly Tyr Lys Thr Arg Phe Glu Gly Arg
        35                  40                  45

Glu Thr Ile Trp Ala His Met Arg Leu Phe Pro Glu Tyr Met Thr Ile
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Leu Thr Ala Ser Gly Gly Lys
                85                  90                  95

Leu Ala Phe Asp Phe Ile Ala Val Trp Arg Thr Arg Asp Gly Gln Ile
            100                 105                 110

Leu Leu Phe Arg Leu Phe Phe Asn Pro Leu Arg Val Leu Glu Pro Leu
        115                 120                 125

Gly Gly Val Glu Ala Ala Ala Lys Ile Val Gln Gly Ala
    130                 135                 140

<210> SEQ ID NO 24
<211> LENGTH: 141
<212> TYPE: PRT
<213> ORGANISM: Artificial Sequence
<220> FEATURE:
<223> OTHER INFORMATION: Synthetic

<400> SEQUENCE: 24

Met Asn Ala Lys Glu Ile Leu Val His Ser Leu Arg Leu Leu Glu Asn
1               5                   10                  15

Gly Asp Ala Arg Gly Trp Cys Asp Leu Phe His Pro Glu Gly Val Leu
            20                  25                  30

Glu Phe Pro Tyr Ala Pro Pro Gly Trp Lys Thr Arg Phe Glu Gly Arg
        35                  40                  45

Glu Thr Ile Trp Ala His Met Arg Leu Phe Pro Glu His Leu Thr Val
    50                  55                  60

Arg Phe Thr Asp Val Gln Phe Tyr Glu Thr Ala Asp Pro Asp Leu Ala
65                  70                  75                  80

Ile Gly Glu Phe His Gly Asp Gly Val Ala Thr Val Ser Gly Gly Lys
                85                  90                  95
```

```
Leu Ala Gln Asp Tyr Ile Ser Val Leu Arg Thr Arg Asp Gly Gln Ile
            100                 105                 110

Leu Leu Tyr Arg Asp Phe Trp Asn Pro Leu Arg His Leu Glu Ala Leu
        115                 120                 125

Gly Gly Val Glu Ala Ala Ala Lys Ile Val Gln Gly Ala
    130                 135                 140
```

HIGH AFFINITY DIGOXIGENIN BINDING PROTEINS

RELATED APPLICATIONS

This application is a U.S. national phase of International Application No. PCT/US2014/025500, filed on Mar. 13, 2014, which claims priority to U.S. Provisional Application No. 61/784,618, filed Mar. 14, 2013, both of which are incorporated by reference herein in their entirety.

STATEMENT OF GOVERNMENT RIGHTS

This invention was made with government support under HDTRA1-11-1-0041 awarded by Defense Threat Reduction Agency. The government has certain rights in the invention.

BACKGROUND

The ability to design proteins with high affinity and selectivity for any given small molecule would have numerous applications in biosensing, diagnostics, and therapeutics, and is a rigorous test of our understanding of the physiochemical principles that govern molecular recognition phenomena. Attempts to design ligand binding proteins have met with little success, however, and the computational design of precise molecular recognition between proteins and small molecules remains an "unsolved problem".

SUMMARY OF THE INVENTION

The present invention provides polypeptides that are high affinity polypeptide ligands of the steroid digoxigenin (DIG) or the related steroids digitoxigenin, progesterone, and β-estradiol, as well as digoxin. The inventors have identified positions of the polypeptides of the invention that provide specificity of the polypeptides for DIG or one or more of the related steroids. As such, the polypeptides of the invention can be used, for example, in steroid biosensors and diagnostics, as well as for therapeutic applications.

In one aspect, the invention provides isolated polypeptides comprising or consisting of an amino acid sequence according to SEQ ID NO:1, wherein the amino acid sequence is at least 70% identical to the amino acid sequence of SEQ ID NO: 15, and wherein the amino acid sequence is not the amino acid sequence of SEQ ID NO: 24.

In various embodiments, the polypeptides comprise or consist of the amino acid sequence of one of SEQ ID NOS: 2—The isolated polypeptide of claim 1, comprising the amino acid sequence of SEQ ID NO: 2-23. In another embodiment, each of residues 34, 101, and 115 are Y. In a further embodiment, 1, 2, or all 3 of residues 34, 101, and 115 are F. In a further embodiment, residue 84 is Y. In another embodiment, at least one of the following is true:

Residue 7 is L;
Residue 41 is W;
Residue 58 is H;
Residue 61 is H;
Residue 64 is W;
Residue 90 is V;
Residue 97 is Y;
Residue 103 is T;
Residue 115 is L;
Residue 119 is W;
Residue 124 is I; and/or
Residue 128 is A.

In another aspect, pharmaceutical compositions are provided, comprising one or more polypeptides of the invention and a pharmaceutically acceptable carrier. The invention also provides isolated nucleic acids encoding a polypeptide of the invention, recombinant expression vector comprising the isolated nucleic acid of the invention operably linked to a control sequence, and recombinant host cell comprising the recombinant expression vectors of the invention.

In a further aspect, the invention provides methods for treating digoxin overdose and/or toxicity, comprising administering to a subject in need thereof an amount effective of one or more polypeptides or pharmaceutical compositions of the invention to treat the digoxin toxicity.

In another aspect, the invention provides methods for detecting digoxin, comprising contacting a sample of interest with one or more polypeptides of the invention under suitable conditions for binding the detectable polypeptide to digoxin present in the sample to form a polypeptide-digoxin binding complex, and detecting the polypeptide-digoxin binding complex.

$$Z = \frac{x - \mu}{\sigma}$$

where x is the sum of enrichment values at position i, µ is the mean sum of enrichment values for all interrogated positions within the fragment library, and σ is the standard deviation of the sums of enrichment values for all interrogated positions within the fragment library. Blue is very optimal (mutations to all other amino acids are disfavored) and red is very suboptimal (mutations are preferred). c, Equilibrium fluorescence polarization measurements of DIG-PEG$_3$-Alexa488 treated with increasing amounts of DIG10. DIG5, scaffold 1z1s, and negative control bovine serum albumin (left panel). Solid lines represent fits to the data to obtain dissociation constants ($K_d$ values) (right panel). Error bars represent standard deviations for at least three independent measurements. $K_d$ values of relevant designs and affinity matured DIG10 variants are given in the right panel. d, Mutations identified during affinity maturation to generate DIG10.1a, DIG10.2, and DIG10.3 mapped on to the computational model of DIG10.3.

Figure 3:
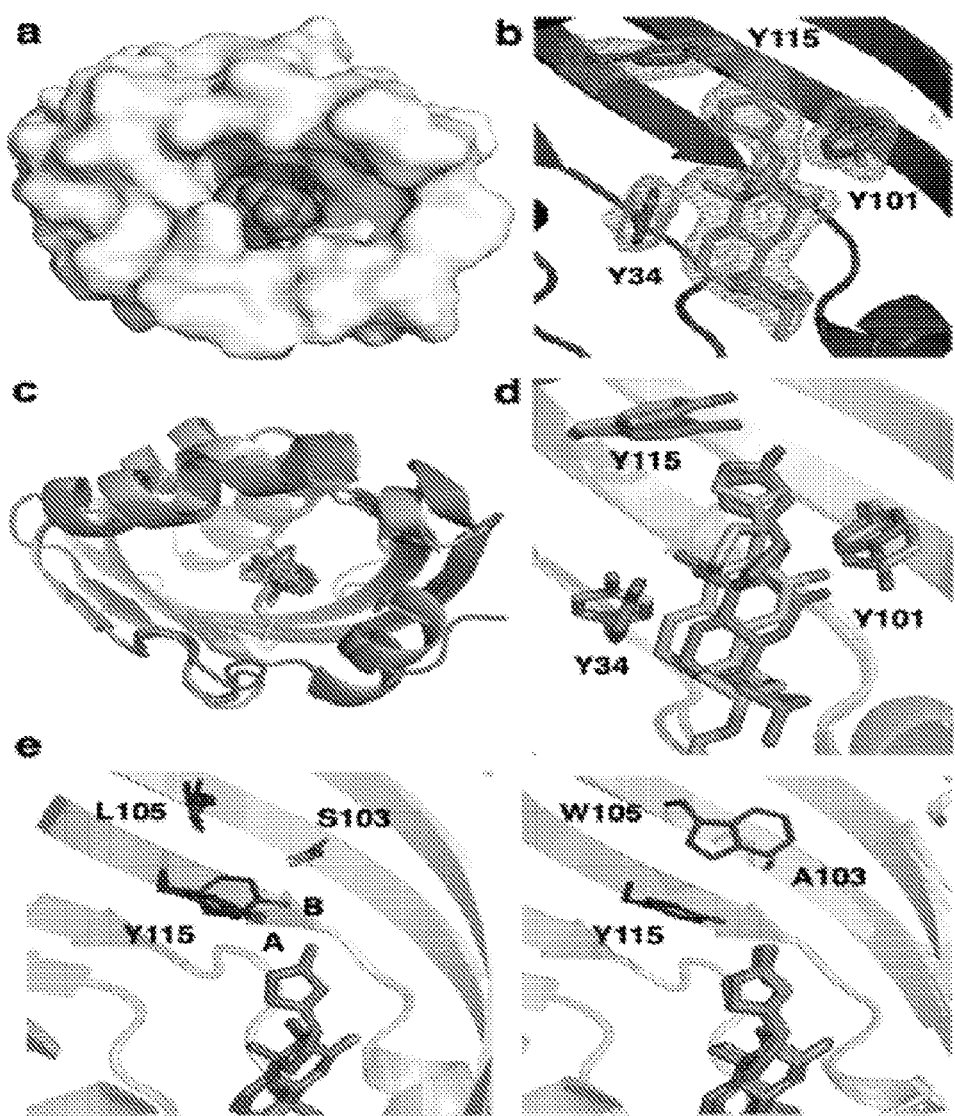

FIG. 3. Crystal Structures of the DIG10.2- and DIG0.3-DIG Complexes. a, Surface representation of the DIG10.2-DIG complex showing the high overall shape complementarity of the interface. DIG is depicted in spheres. DIG10.2 is a dimer and crystallized with four copies in the asymmetric unit. b, 2F$_o$-F$_c$ omit map electron density of DIG interacting with Tyr34, Tyr101, and Tyr115 contoured at 1.0 sigma. c, Backbone superposition of the crystal structure of the DIG10.2-DIG complex with the computational model shows close agreement between the two. d, Binding site backbone superposition shows that the ligand and the three programmed Tyr hydroxyl groups are in their designed conformations. e, Configurational side chain entropy between the four crystallographic copies of the DIG10.2-DIG (left panel) complex and chains A, B, C, H, and I of the DIG10.3-DIG (right panel) complex. The side chains of DIG10.3 at positions 103, 105, and 115 each adopt only a single rotamer. DIG10.2 Tyr115 conformation A adopts a more canonical hydrogen-bonding geometry than that of conformation B.

FIG. 4. Steroid Binding Selectivity. a, The x-ray crystal structure of the DIG10.3-DIG complex (left panel) and the chemical structures of steroids interrogated in equilibrium competition fluorescence polarization assays (right panel). b, Steroid selectivity profile of DIG10.3. Solid lines represent fits to the data to obtain half-maximal inhibitory concentrations (IC$_{50}$ values) and error bars indicate standard deviations for at least three independent measurements. c, Steroid selectivity profile of DIG10.3 Tyr101Phe. Dashed lines show qualitative assessments of the inhibitory effects for cases in which the data could not be fit due to experimental limitations (see Supplementary Methods). d, Steroid selectivity profile of DIG10.3 Tyr34Phe. e, Steroid selectivity profile of DIG10.3 Tyr34Phe/Tyr99Phe/Tyr101F.

Figure 5A:
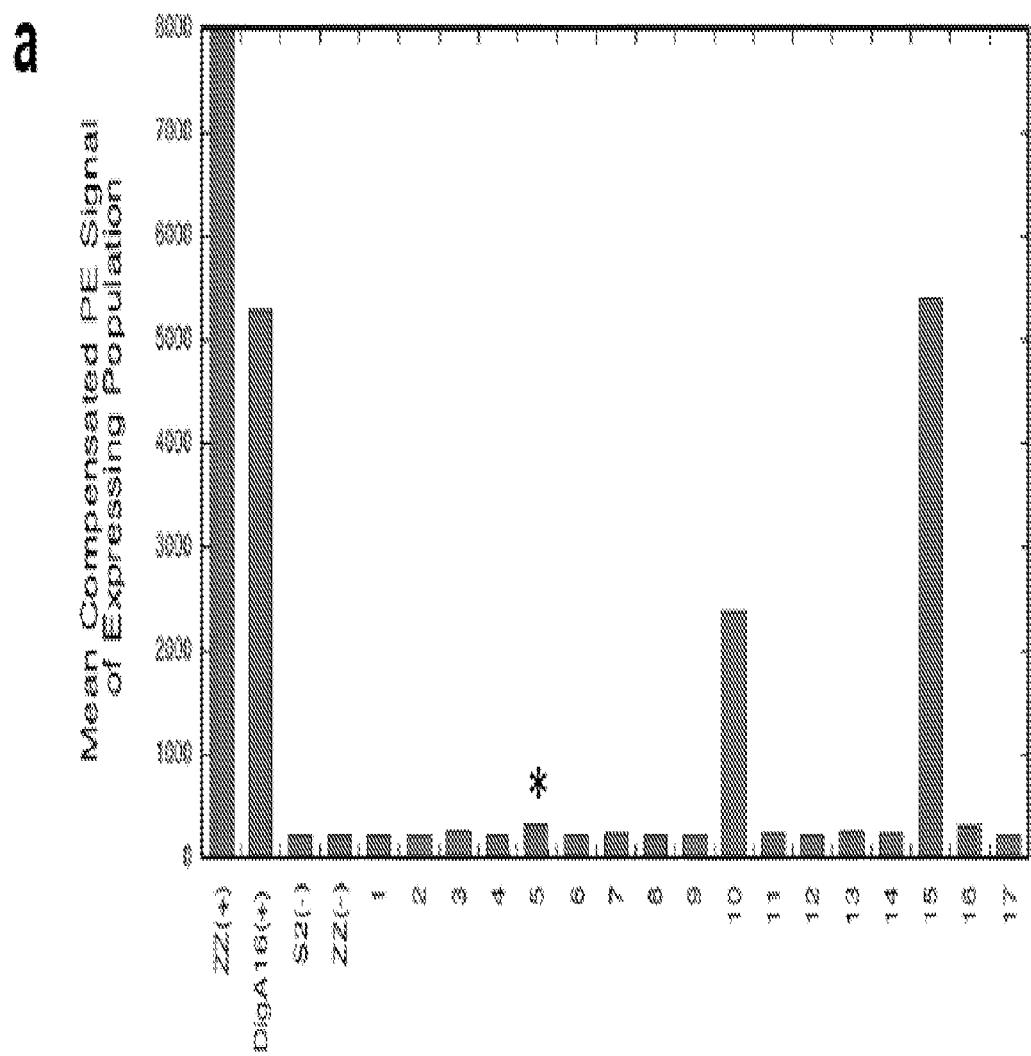
Figure 5B:
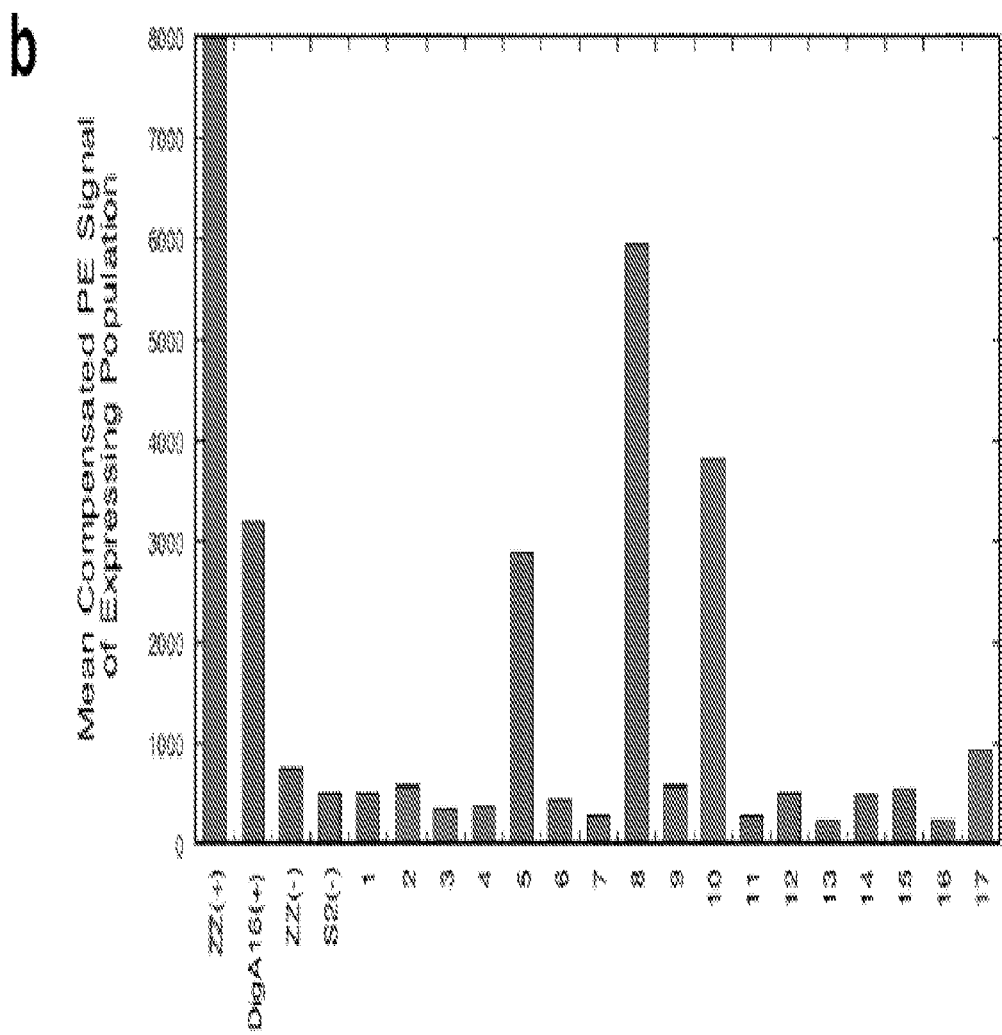

FIG. 5. Experimental characterization of computationally designed DIG binders by yeast surface display. a, Compensated mean binding (PE) signals of the expressing populations of yeast cells displaying computationally designed proteins on their cell surfaces. Binding was interrogated by labeling cells with a pre-incubated mixture of 2.7 µM biotinylated DIG-functionalized BSA (~10 DIG/BSA) and phycoerythrin (PE)-conjugated streptavidin. Cell populations shown are an anti-DIG antibody serving as a positive control for binding (ZZ(+)), an engineered DIG-binding lipocalin (DigA16(+)), two negative controls for binding (ZZ(-) and S2(-)), and designed proteins DIG1 through DIG17. DIG10 and DIG15 show strong binding signals. DIG5 shows a reproducible signal that is slightly above background levels (starred). b, Binding was interrogated by labeling cells with a pre-incubated mixture of 2.7 µM biotinylated DIG-functionalized RNase (~6 DIG/RNase) and phycoerythrin (PE)-conjugated streptavidin. DIG5, DIG8, and DIG10 show strong binding signals. DIG10 and DIG5 bind to both labels.

Figure 6A:
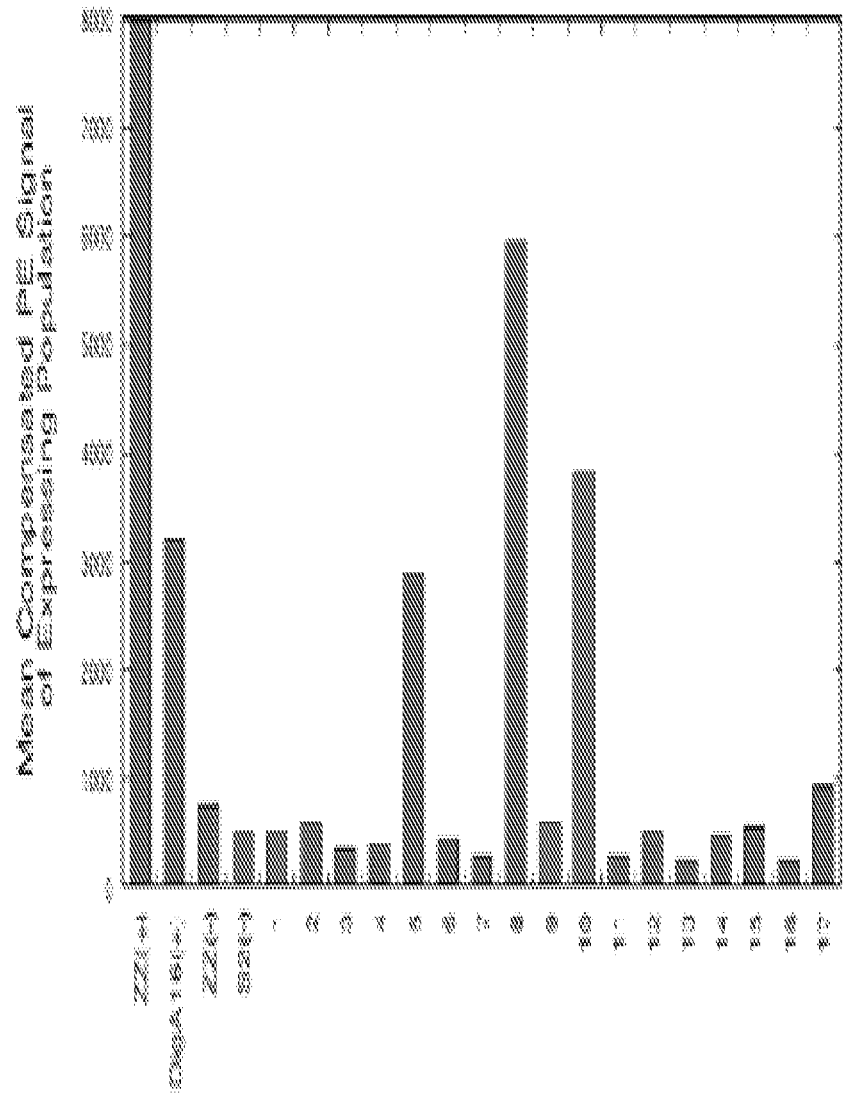
Figure 6B:
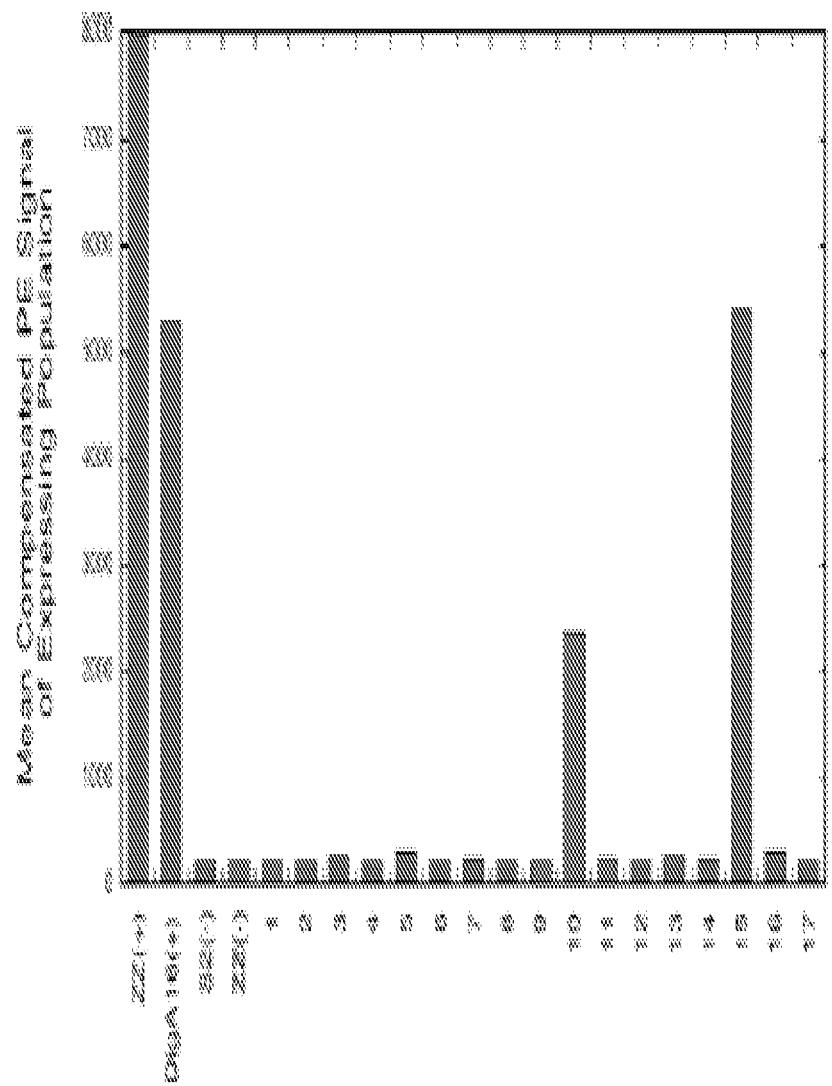
Figure 6C:
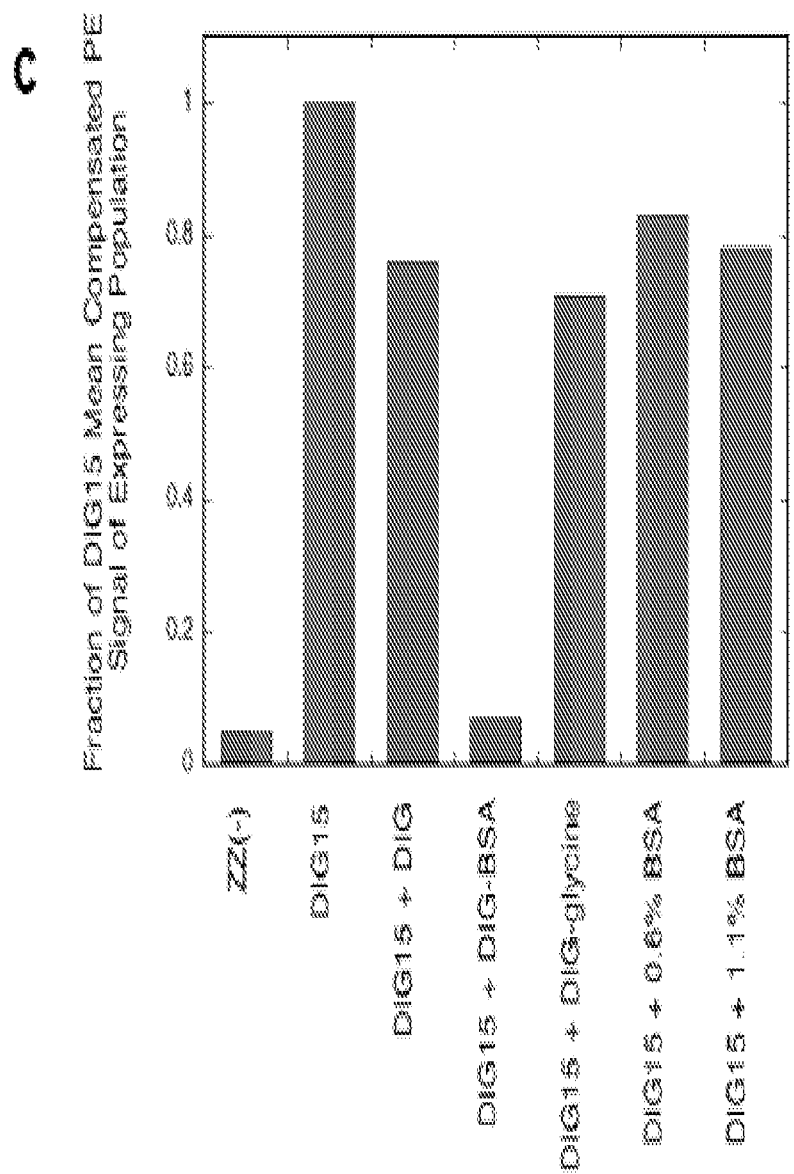

FIG. 6. Experimental yeast surface display competition assays of DIG5, DIG8, and DIG15. a, Compensated mean binding (PE) signals of the expressing populations of yeast cells displaying DIG5 and DIG5 scaffold 1z1s. 1z1s (structural genomics target PA3332) is a protein of unknown function from *Pseudomonas aeruginosa* and has no functionally characterized homologs with >20% sequence identity. 1z1s belongs to the nuclear transport 2 (NTF2)-like structural superfamily, a functionally diverse fold class of which the steroid-metabolizing enzyme ketosteroid isomerase is also a member. Cells were labeled with 2.7 µM DIG-RNase-biotin and SAPE. In the presence of 790 µM unlabeled DIG, the signal is reduced to that of the negative control ZZ(-), revealing that binding is specific for DIG and not other assay components. Scaffold 1z1s does not show a binding signal, suggesting that binding is mediated by the designed interface. b, Compensated mean binding (PE) signals of the expressing populations of yeast cells displaying DIG8 and DIG8 scaffold 3hk4. Cells were labeled with 2.7 µM DIG-RNase-biotin and SAPE. In the presence of 790 µM unlabeled DIG, the DIG8 signal is reduced by half, suggesting that binding is likely specific for DIG. The binding signal is not reduced to background levels probably because binding is weak and the unlabeled DIG is not present in high enough concentration to overcome the avidity affects of the DIG-RNase-biotin label. This explanation is corroborated by the observation that unlabeled 130 µM RNase does not affect the DIG8 signal. Scaffold 3hk4, NTF2-like superfamily member and structural genomics target MLR7391 (PDB ID 3hk4) from *Mesorhizobium loti*, does bind to DIG-RNase-biotin with a weaker (and more avidity-based) signal than DIG8. 3hk4 has not been functionally characterized. c, Compensated mean binding (PE) signals of the expressing populations of yeast cells displaying DIG15. Cells were labeled with 2.7 µM DIG-BSA-biotin and SAPE. In the presence of 1.6 mM unlabeled DIG, the binding signal is only reduced slightly. Similar effects are seen with ~1.6 mM DIG-linker conjugate (DIG-NHS ester reacted with glycine) and BSA. However, the signal was completely reduced upon incubation with 18 µM DIG-BSA. The signal is slightly reduced in the presence of additional BSA (0.6% or 1.1% BSA). Either the DIG15 binding signal is not reduced to background levels in the presence of unlabeled DIG because binding is weak and the amount of competitor in the assay is not enough to overcome the avidity affects of the DIG-RNase-biotin label or because the design recognizes both DIG and BSA non-specifically. Due to these complications, DIG15 was not characterized further.

Figure 7A:
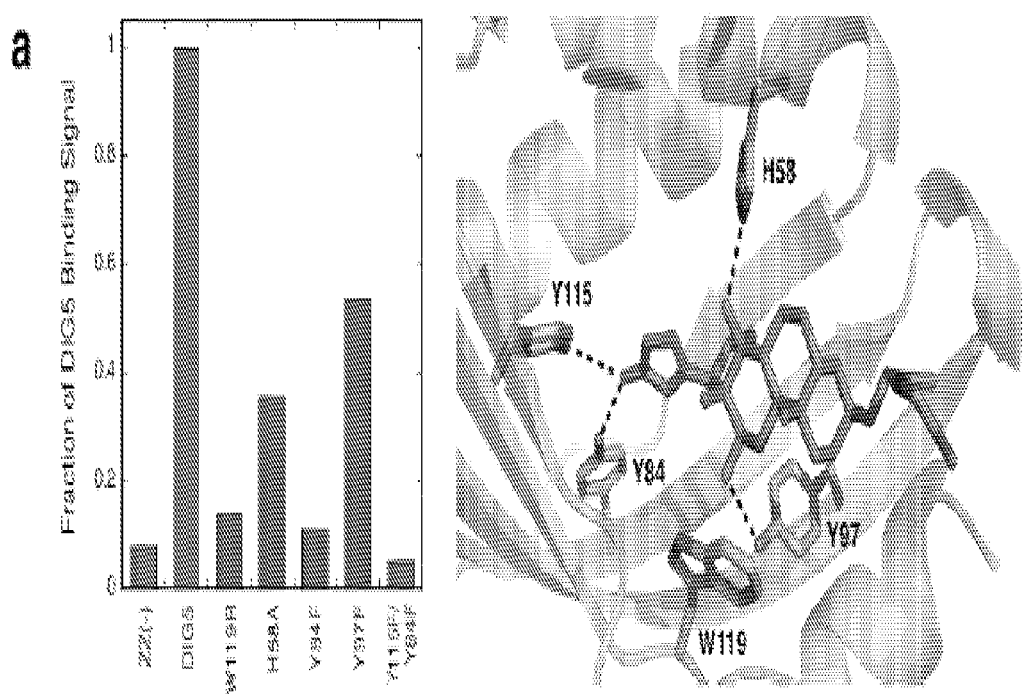
Figure 7B:
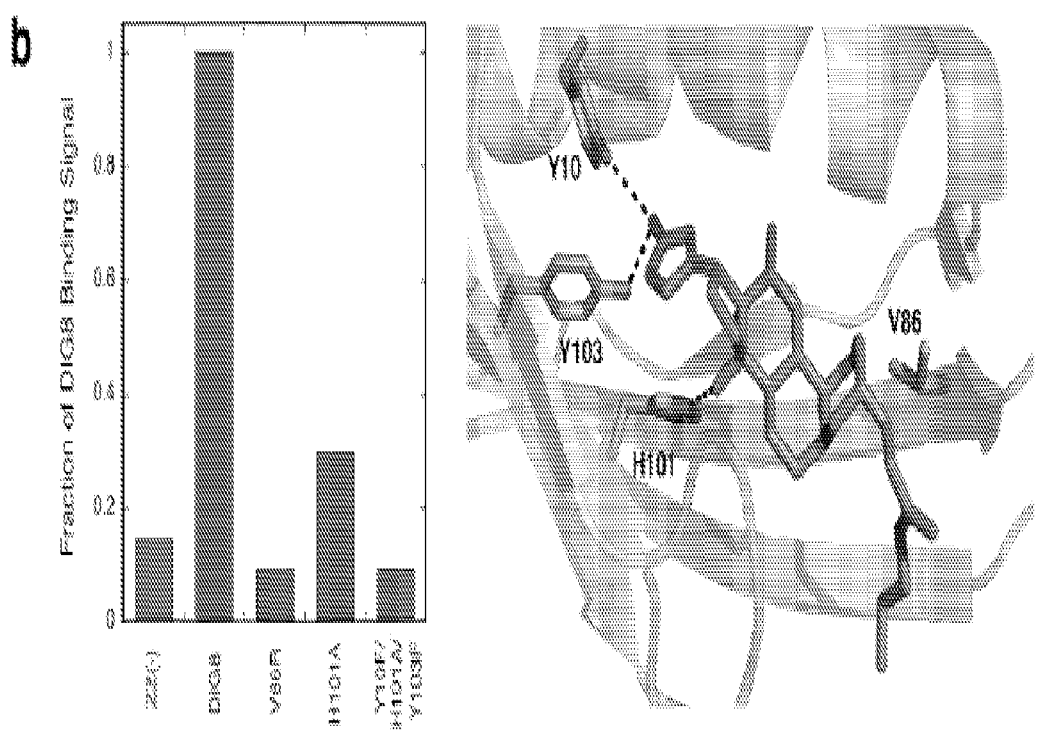

FIG. 7. Yeast surface display knockout mutagenesis studies of DIG5 and DIG8. a, Functional substitutions of DIG5 key modeled interacting residues leads to expressing-population compensated mean binding (PE) signals that are reduced relative to DIG5 (left panel). Cells were labeled with 1.5 µM DIG-RNase-biotin and SAPE. Mutation of binding site residue Trp119 to larger Arg indicates that DIG binds in the intended pocket of the computational model (right panel). Mutation of hydrogen bonding residue Tyr84 to Phe alone and in combination with the Tyr115Phe substitution leads to a binding signal that is reduced to background negative control (ZZ(−)) levels, confirming that this residue is necessary for binding. Mutation of His58 and Tyr97, which make hydrogen bonds in the computational model, to Ala and Phe, respectively, also lead to reduced binding signals. c, Functional substitutions of DIG8 key modeled interacting residues leads to expressing-population compensated mean binding (PE) signals that are reduced relative to DIG8 (left panel). Cells were labeled with 2.7 M DIG-RNase-biotin and SAPE. Mutation of binding site residue Val86 to larger Arg indicates that DIG binds in the intended pocket of the computational model (right panel). Simultaneous mutation of hydrogen bonding residues Tyr10, His101, and Tyr103 to Phe, Ala, and Phe, respectively, leads to a binding signal that is reduced to background negative control (ZZ(−)) levels. Mutation of His101 to Ala also leads to a reduced binding signal. Despite the observation that the DIG8 scaffold PDB ID 3hk4 does bind to DIG-RNase (FIG. 8), these results indicate that the designed interface could contribute to binding of the design.

Figure 8A:
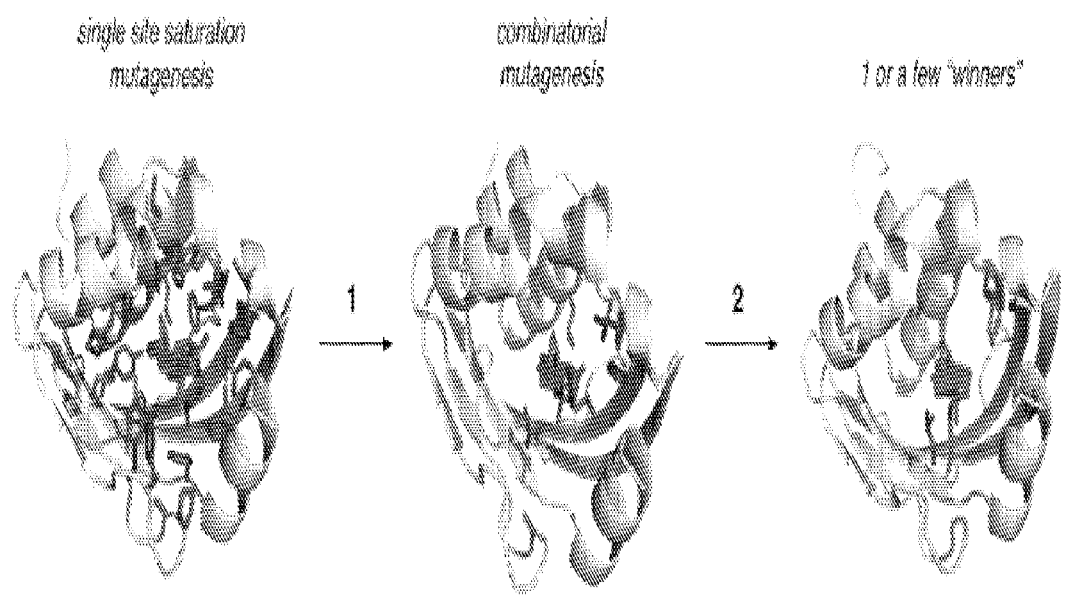
Figure 8B:
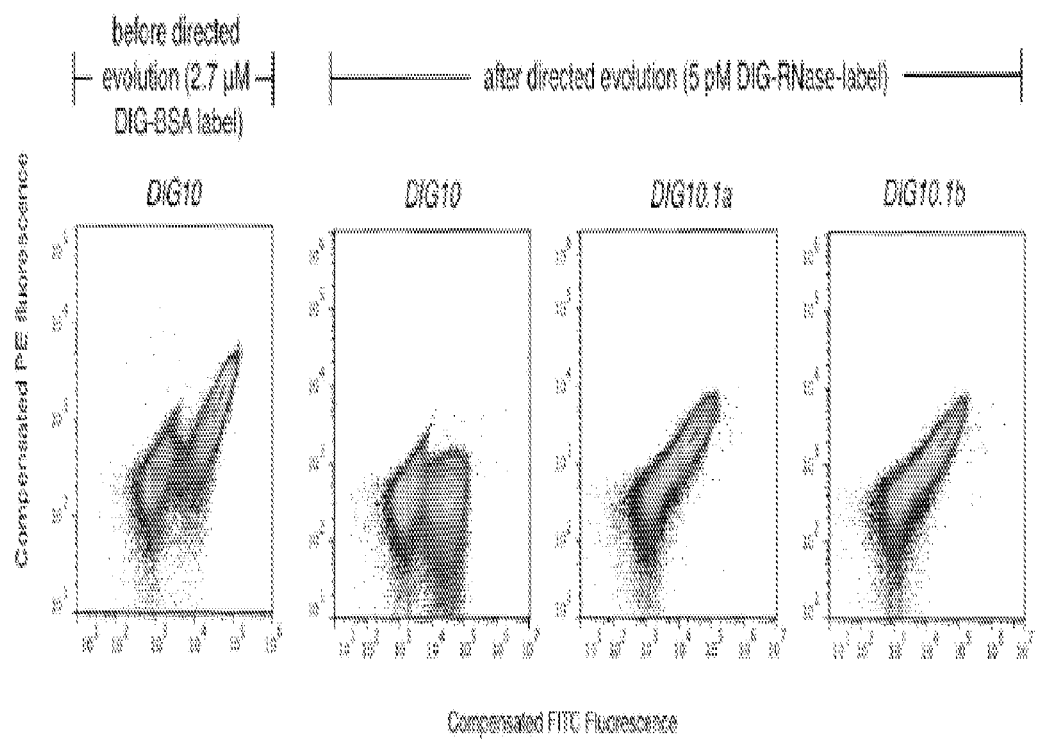

FIG. 8. Affinity maturation of DIG10: Round 1. a, Strategy for round 1 affinity maturation of DIG10. A single site-saturation mutagenesis library was constructed by mutating each of 34 positions in the binding pocket (magenta sticks, left panel) to all other amino acids by Kunkel mutagenesis with degenerate NNK primers. After several rounds of selections with highly avid DIG-BSA-biotin and SAPE (step 1), eight positions were identified for which mutations lead to improved binding. Beneficial mutations, chemically similar residue types, and the DIG10 "wild type" amino acids at these positions (magenta sticks, middle panel) were combined combinatorially by Kunkel mutagenesis with degenerate primers. Following several rounds of increasingly stringent selections with DIG-BSA-biotin or DIG-RNase and SAPE (step 2), two variants, DIG10.1a, and DIG10.1b, were identified, each having five mutations from DIG10 (sticks, right panel). b, Flow cytometric analysis of cells expressing DIG10, DIG10.1a, and DIG10.1 b. DIG10 shows a strong binding signal when labeled with a pre-incubated mixture of 2.7 µM DIG-BSA-biotin and SAPE but not when subjected to a more stringent multistep labeling procedure in which cells were first labeled with 5 pM DIG-RNase and then with SAPE. DIG10.1a and DIG10.1b show strong binding signals from the latter labeling procedure, however, demonstrating that these variants have improved binding affinities.

Figure 9A:
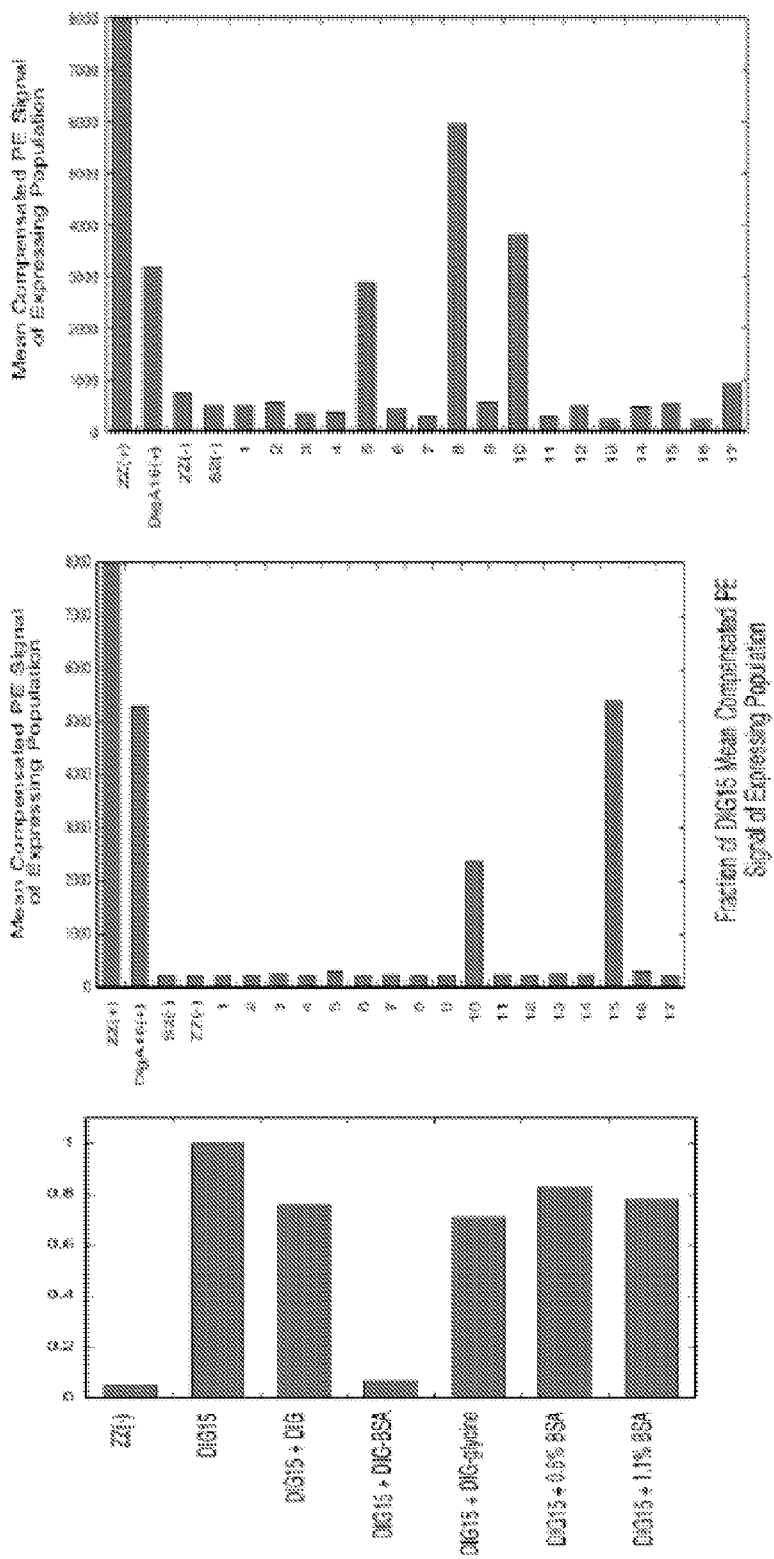
Figure 9B:
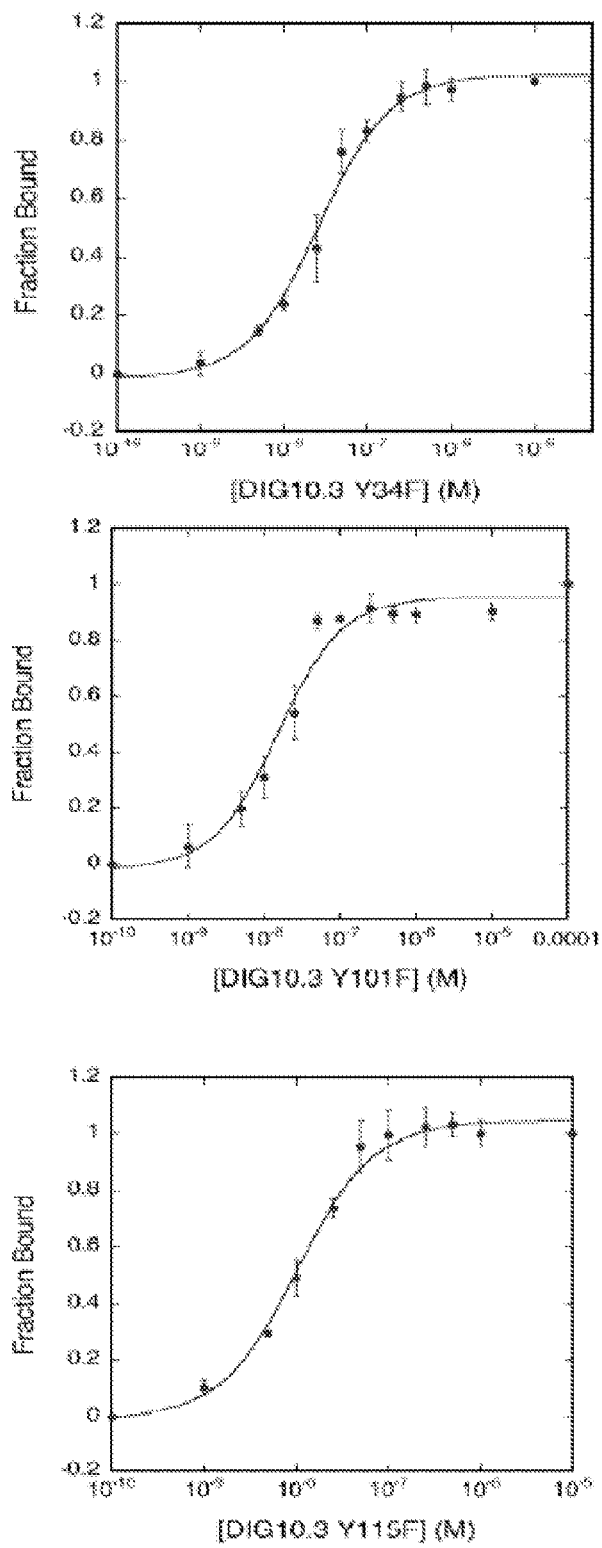
Figure 9C:
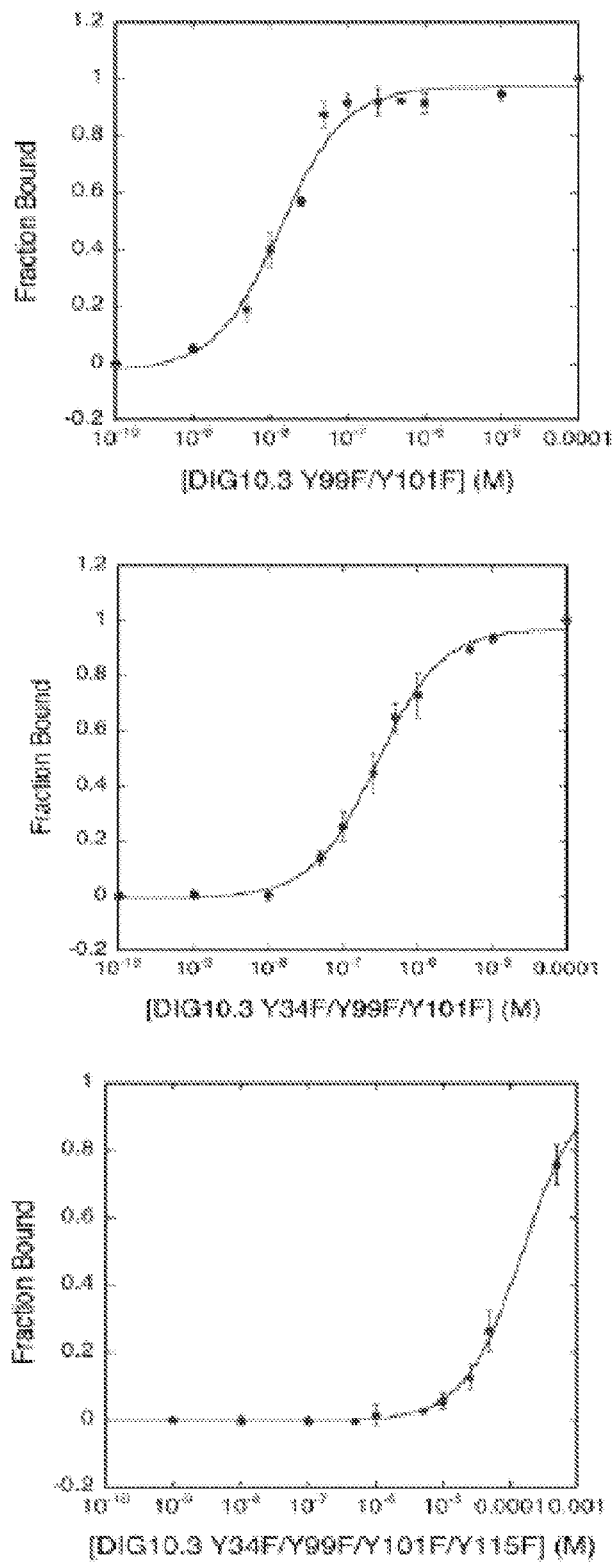

FIG. 9. Fluorescence polarization affinity measurements of DIG10 evolved variants, a, Equilibrium fluorescence polarization measurements of DIG-PEG$_3$-Alexa488 treated with increasing amounts of DIG10.1 (left panel), DIG10.2 (middle panel), and DIG10.3 (right panel). Solid lines represent fits to the data to obtain dissociation constants ($K_d$ values). For DIG10.1, [DIG-PEG$_3$-Alexa488]=10 nM. For DIG10.2, [DIG-PEG$_3$-Alexa488]=1 nM. For DIG10.3, [DIG-PEG$_3$-Alexa488]=0.5 nM. b, Equilibrium fluorescence polarization measurements of DIG-PEG$_3$-Alexa488 treated with increasing amounts of DIG10.3 variants Tyr34Phe (panel 1), Tyr101Phe (panel 2), Tyr115Phe (panel 3), Tyr99Phe/Tyr101Phe (panel 4), Tyr34Phe/Tyr99Phe/Tyr101Phe (panel 5), and Tyr34Phe/Tyr99Phe/Tyr101Phe/Tyr115Phe (panel 6). Solid lines represent fits to the data to obtain dissociation constants ($K_d$ values). Error bars represent standard deviations for at least three independent measurements collected using at least two different batches of purified protein. For Tyr34Phe, Tyr101Phe, Tyr115Phe, and Tyr99Phe/Tyr01Phe. [DIG-PEG$_3$-Alexa488]=2 nM. For Tyr34Phe/Tyr99Phe/Tyr101Phe and Tyr34Phe/Tyr99Phe/Tyr101Phe/Tyr115Phe, [DIG-PEG$_3$-Alexa488]=10 nM.

Figure 10A:
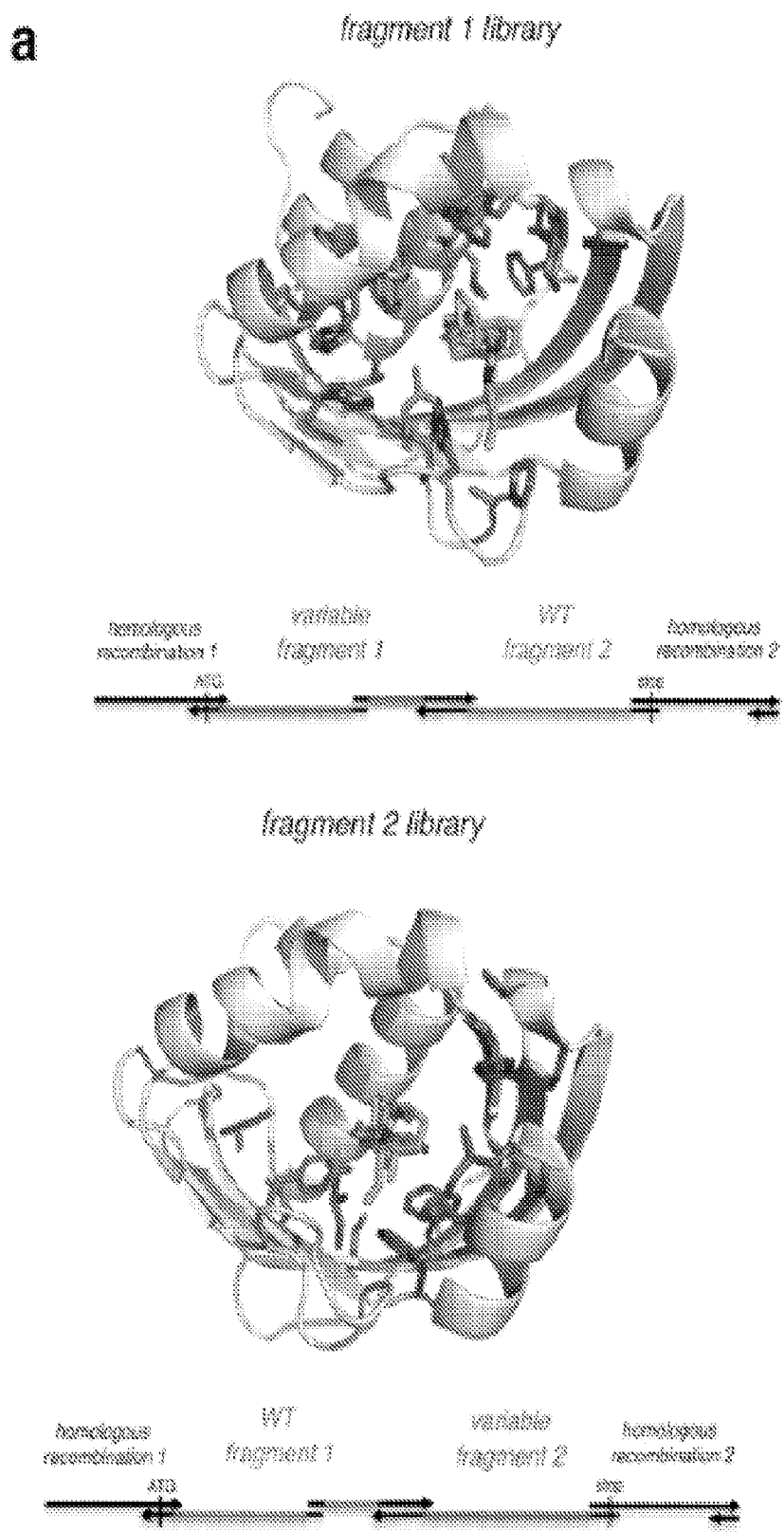
Figure 10B:
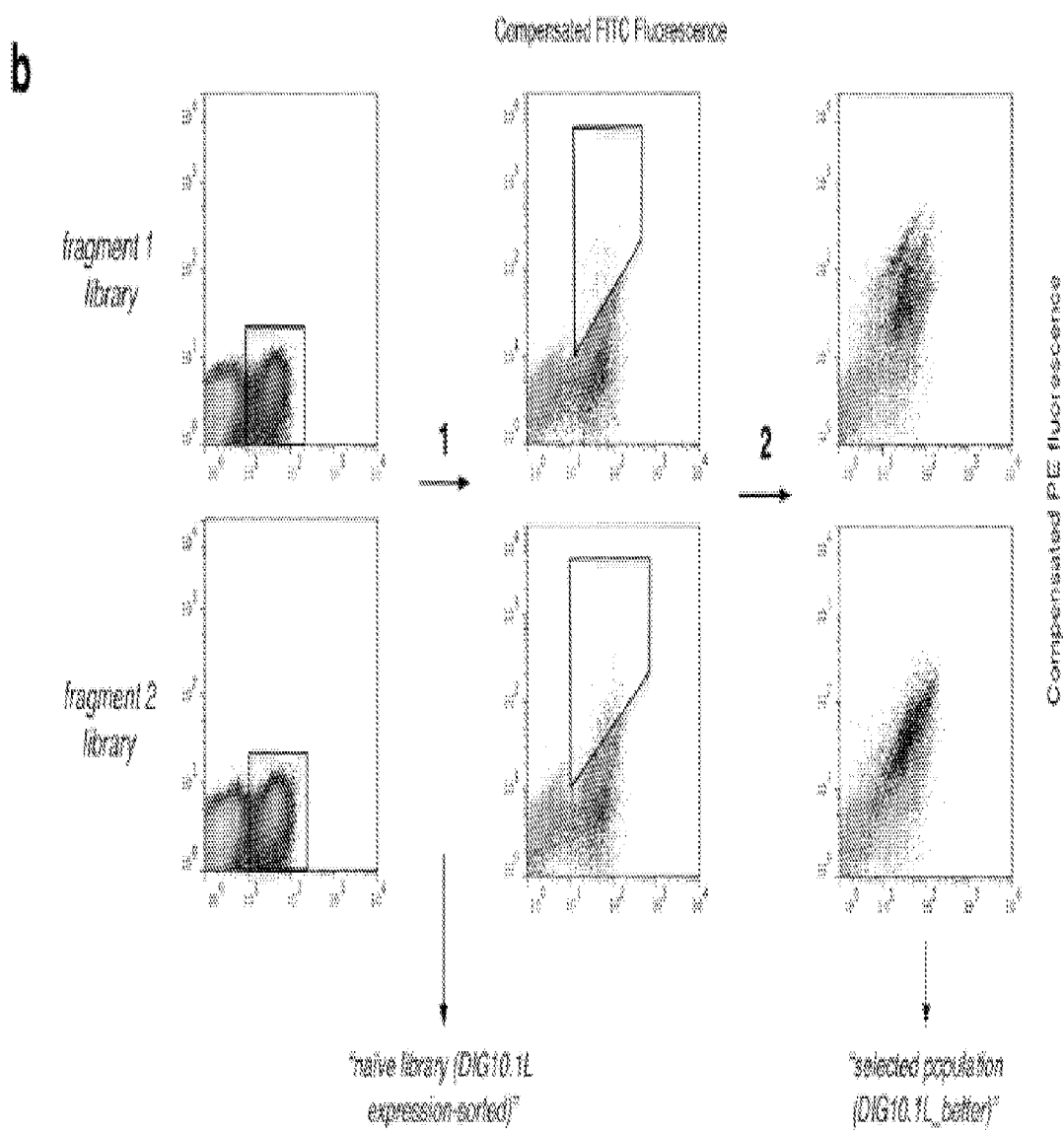

FIG. 10. DIG10.1a deep sequencing library construction and selections. a, DIG10.1a-based deep sequencing fragment libraries. Residues included in the fragment 1 (left) and fragment 2 (right) libraries are depicted, respectively (upper panels). Libraries were constructed by recursive PCR using a combination of mutagenized (colored) and wild-type (gray) oligos (lower panels). b, Flow cytometry plots of yeast surface display selections for deep sequencing experiments. Fragment libraries 1 and 2 were first labeled with anti-cmyc-FITC and the expressing populations were collected using fluorescent gates (black squares, left panel step 1). Expressing cells were recovered, labeled with 100 nM monovalent DIG-PEG$_3$-biotin and then SAPE, and then library clones having higher PE binding signals than DIG10.1a were collected using fluorescent gates (black quadrilaterals, center panel, step 2). To reduce noise, this procedure was repeated once more using the same conditions. Following these two rounds of binding selections, the selected cells showed higher binding signals than DIG10.1a (right panel). DNA from the expression-sorted naïve libraries and the selected libraries were subjected to deep sequencing.

Figure 11A:
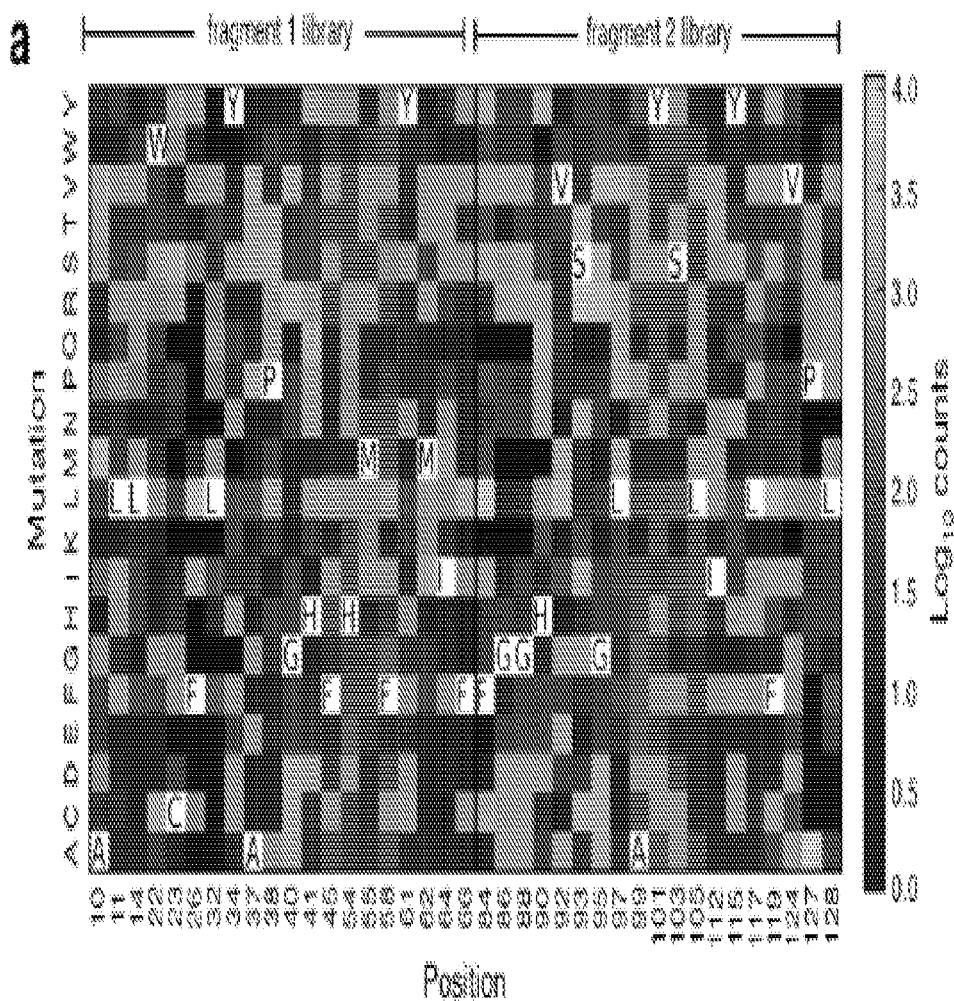
Figure 11B:
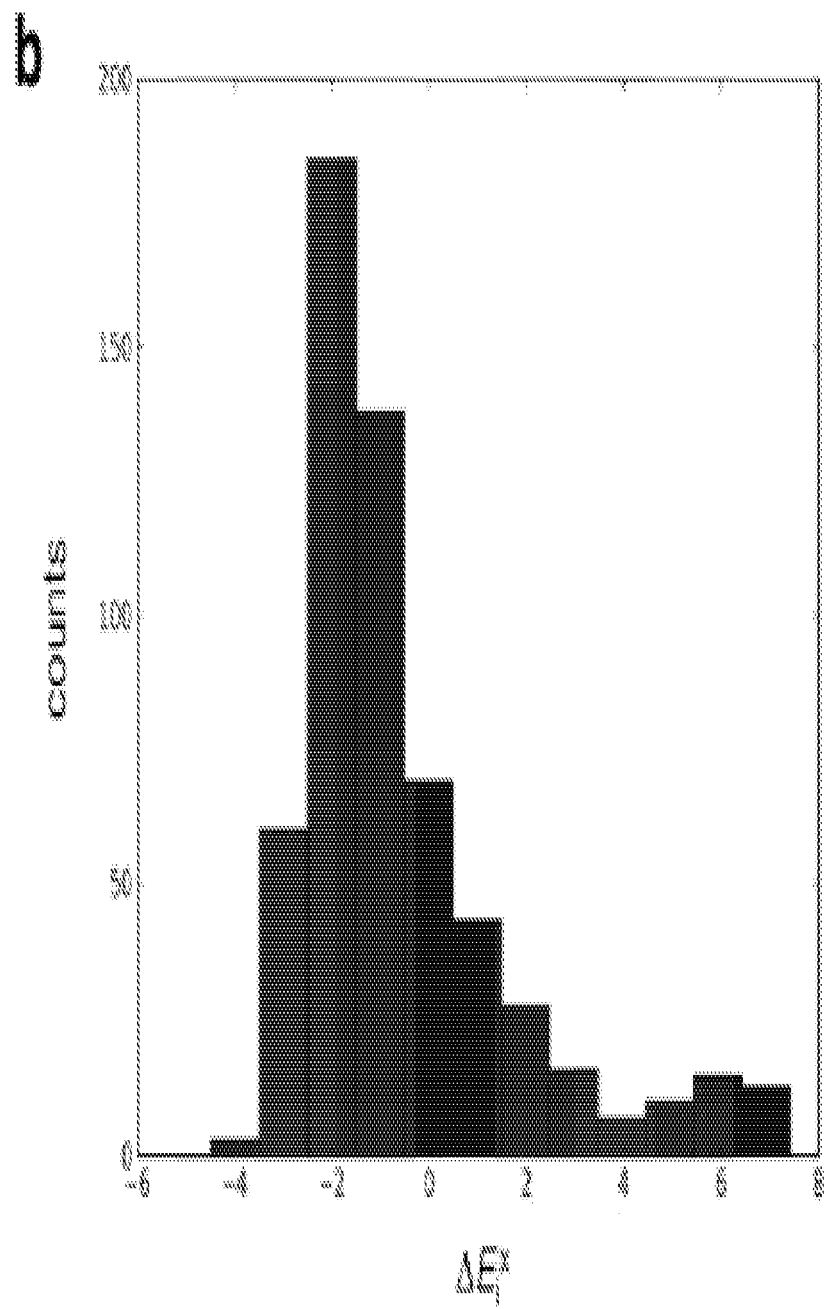

FIG. 11. DIG10.1a deep sequencing library statistics. a, A data matrix showing the number of counts for each single mutation in the unselected N-terminal (fragment 1) and C-terminal (fragment 2) deep sequencing libraries. The DIG10.1a amino acid at each position is indicated in bold using its one-letter amino acid code. b, A histogram of the deep sequencing data in FIG. 2a indicates that most mutations are deleterious for binding.

Figure 12A:
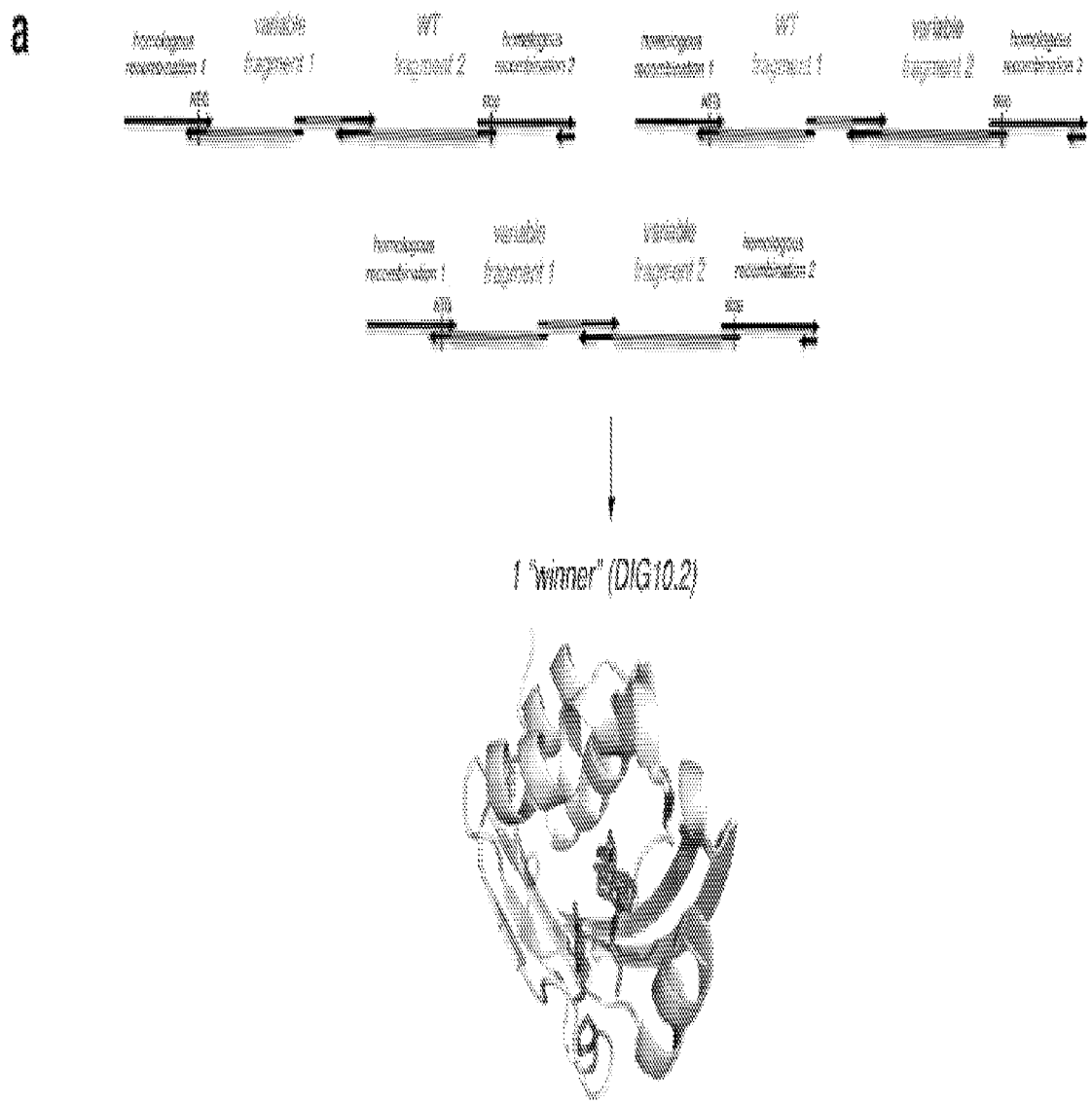
Figure 12B:
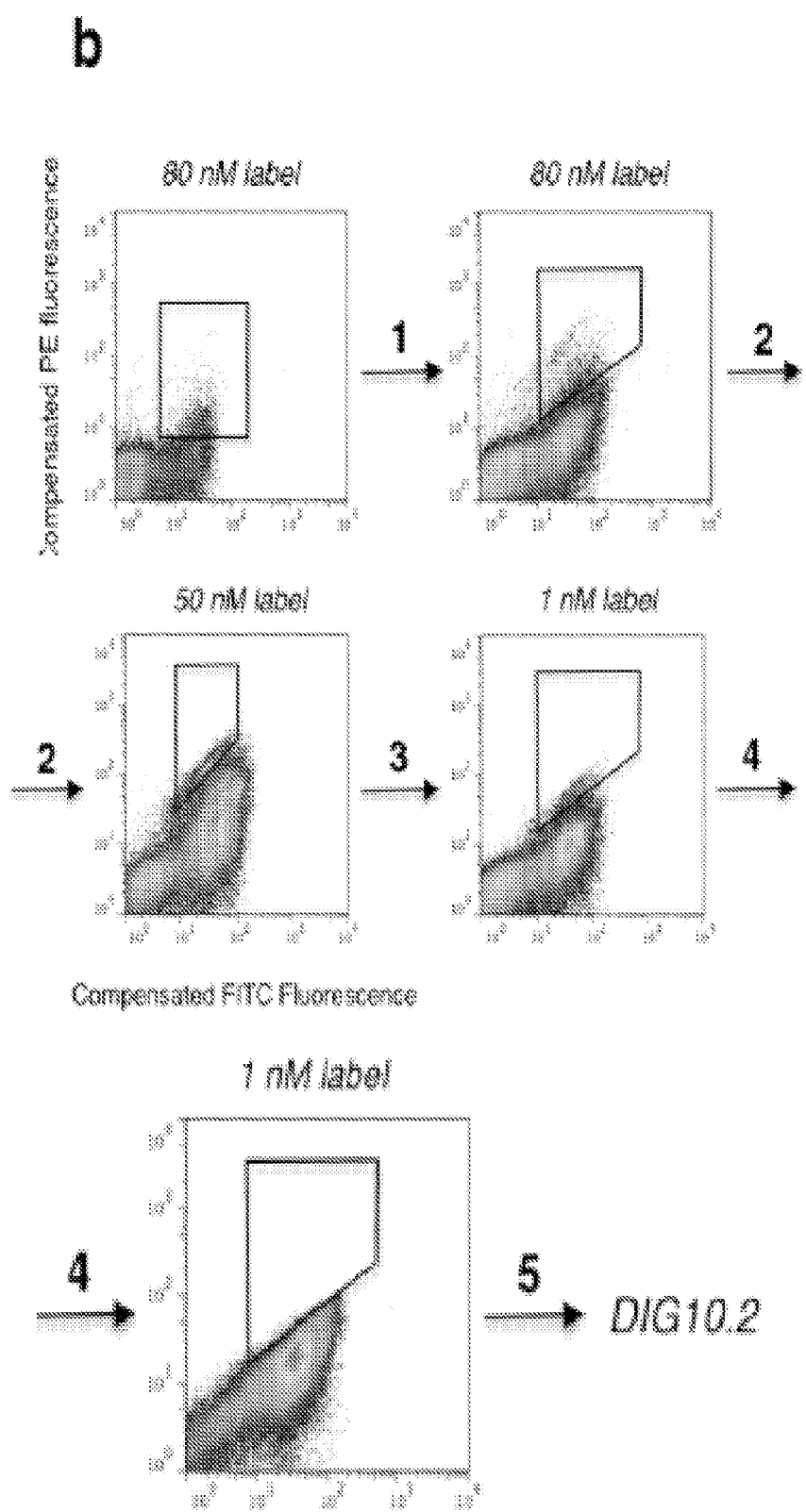

FIG. 12. Affinity maturation of DIG10.1a: Round 2. a, The round 2 DIG10.1a affinity maturation library was constructed by pooling the products of three recursive PCR reactions using different combinations of mutagenized and wild-type (gray) oligos (upper panel). After several rounds of selections of the library with monovalent DIG-BSA-biotin and then SAPE, a single best variant, DIG10.2, having two mutations from DIG10.1a, was identified. b, Flow cytometry plots of yeast surface display selections for affinity maturation round 2. Yeast cells were subjected to five increasingly stringent rounds of selections with DIG-PEG$_3$-biotin and then SAPE using fluorescent gates (black quadrilaterals).

Figure 13A:
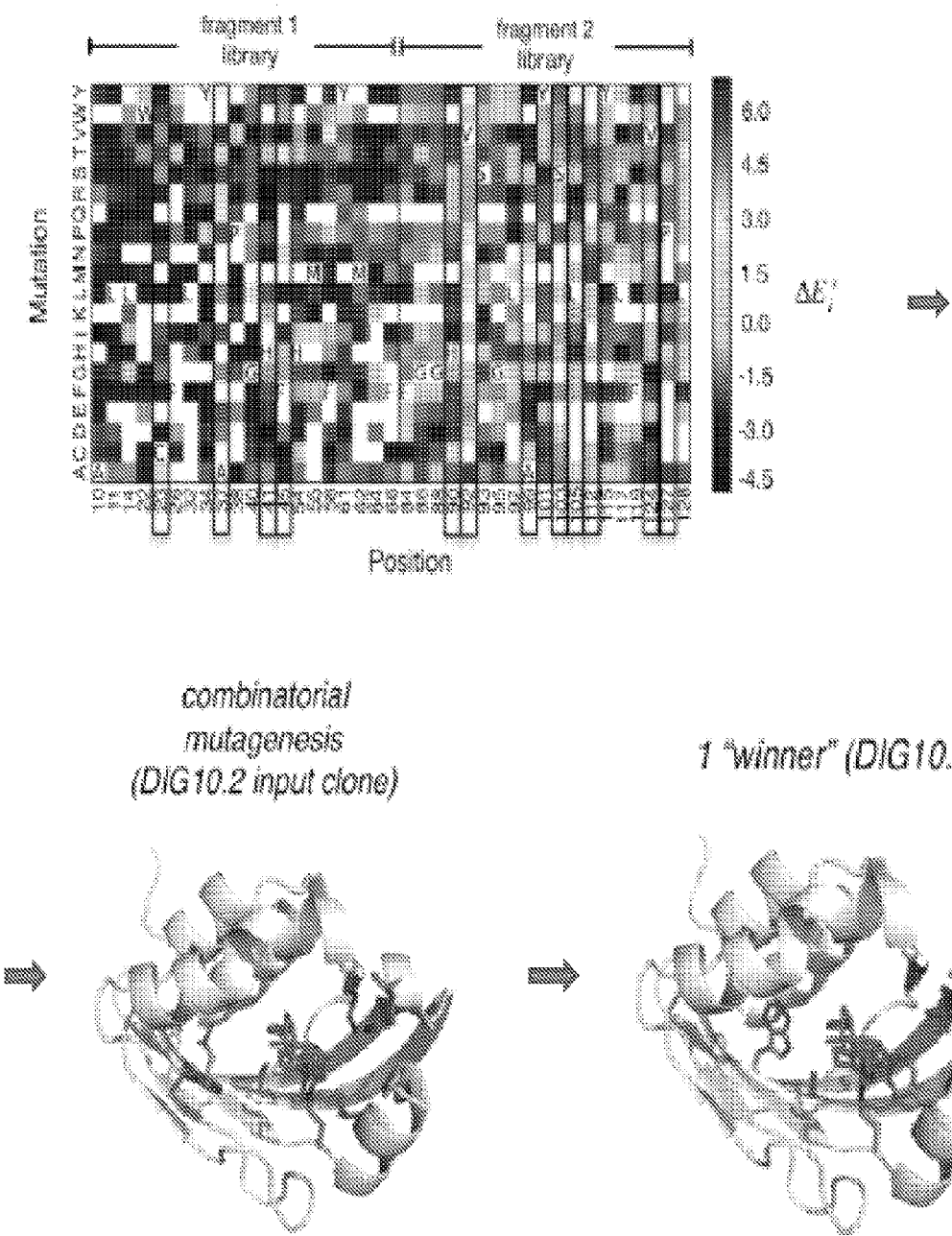
Figure 13B:
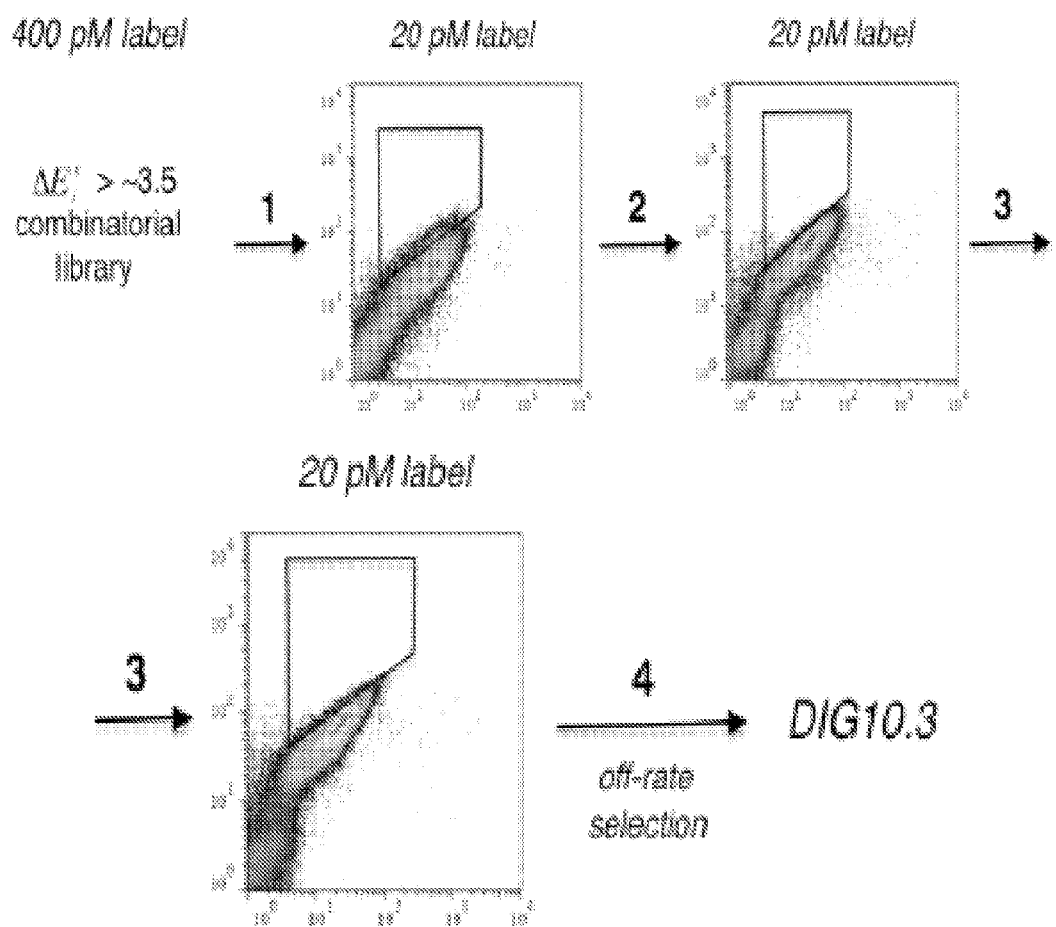

FIG. 13. Affinity maturation of DIG10.2: Round 3. a, Strategy for round 3 affinity maturation of DIG10.2. Mutations having $\Delta E_i^x > \sim 3.5$ in the deep sequencing experiment (left panel) and the DIG10.2 amino acids at these positions (middle panel) were combined combinatorially by Kunkel mutagenesis with degenerate primers. Selections converged to a single variant, DIG10.3, having six mutations from DIG10.2 (right panel). b, Flow cytometry plots of yeast surface display selections for affinity maturation round 3. The library was subjected to four increasingly stringent rounds of selections with DIG-PEG$_3$-biotin and then SAPE using fluorescent gates (black quadrilaterals). An off-rate selection was used in the last round.

Figure 14:
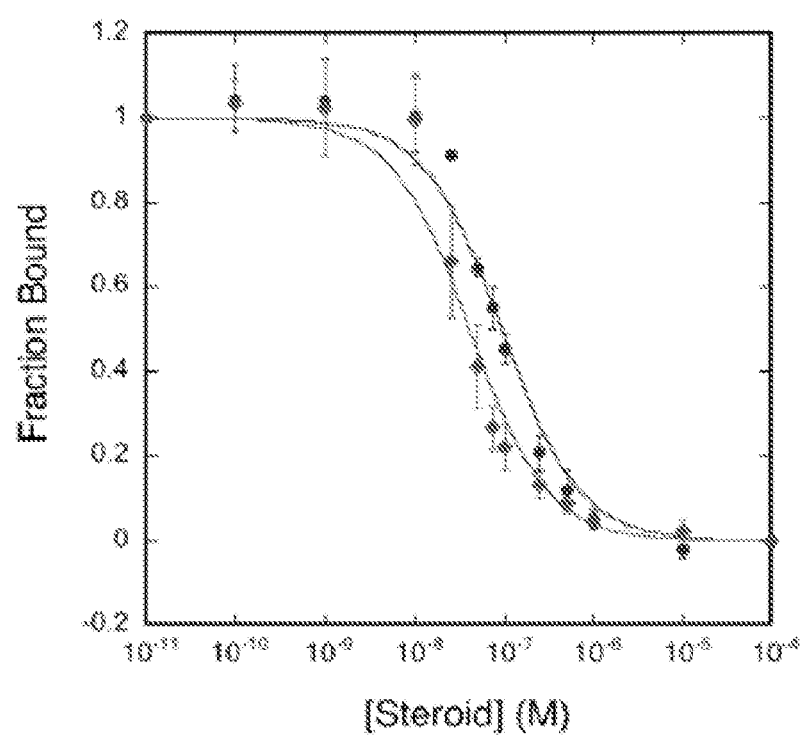

FIG. 14. Equilibrium competition fluorescence polarization assays of DIG10.3 with digoxin. Unlabeled digoxin or digoxigenin was added to a solution of DIG10.3 and DIG-PEG$_3$-Alexa488 in increasing amounts. Solid lines represent fits to the data to obtain the half-maximal inhibitory concentrations (IC$_{50}$ values). Error bars represent standard deviations for at least three independent measurements collected using at least two different batches of purified protein. The affinity of DIG10.3 for digoxin is slightly higher than that for DIG.

Figure 15:
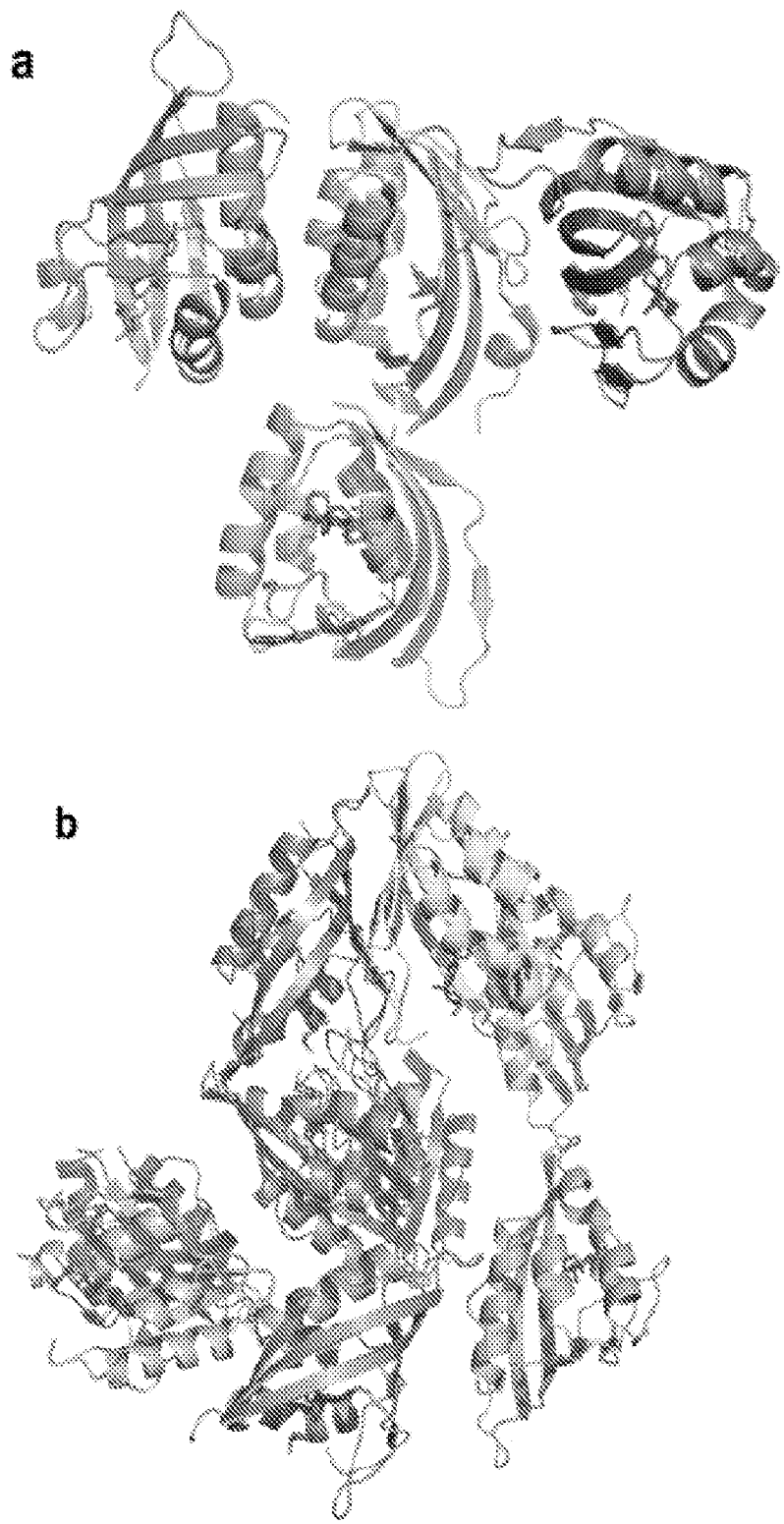

FIG. 15. Crystal packing in the DIG10.2-DIG and DIG10.3-DIG Complexes. a, The asymmetric unit of the DIG10.2 crystal structure contains four copies, each of which bind a molecule of DIG. b, The asymmetric unit of the DIG10.3 crystal structure contains nine copies, each of which bind a molecule of DIG.

Figure 16:
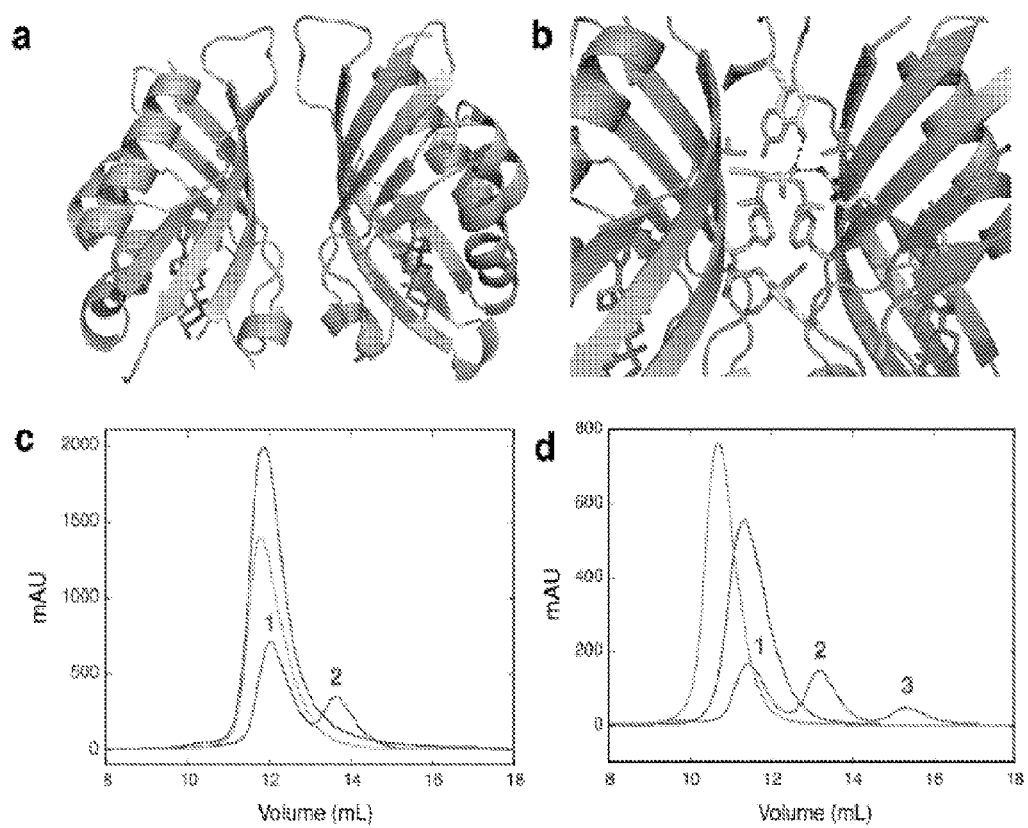

FIG. 16. Evidence that DIG proteins are dimeric. a, The dimeric unit of DIG10.2 observed in the crystal structure. The protomers are related by a pseudosymmetric or symmetric C2 axis. DIG is shown in magenta sticks. b, The dimer interface is formed by specific intermolecular salt-bridges, packing interactions, and hydrogen bonds between the solvent-facing sides of the curved β-sheets. c, Preparative Superdex 75 gel filtration traces of DIG10, DIG10.1b, molecular weight standard horse heart cytochrome c ($M_r$=29 kDa, red 1), and molecular weight standard bovine erythrocytes carbonic anhydrase ($M_r$=12.4 kDa, red 2). Both DIG10 and DIG10.1b elute near their expected dimeric molecular weights (36 kDa). Both proteins are well-behaved in solution, and the traces show no evidence for sample heterogeneity or higher-order aggregate species. d, Analytical Superdex 75 gel filtration traces of DIG10.3, pre-formed DIG10.3-DIG complex, molecular weight standard horse heart cytochrome c ($M_r$=29 kDa), molecular weight standard bovine erythrocytes carbonic anhydrase ($M_r$=12.4 kDa,) and bovine aprotinin (6.5 kDa, red 3). DIG10.3 elutes near its expected dimeric molecular weight (36 kDa). The DIG10.3-DIG complex elutes at a slightly shorter retention volume. DIG10.3 and the DIG10.3-DIG complex are both well behaved in solution, and the traces show no evidence for sample heterogeneity or higher-order aggregate species.

Figure 17:
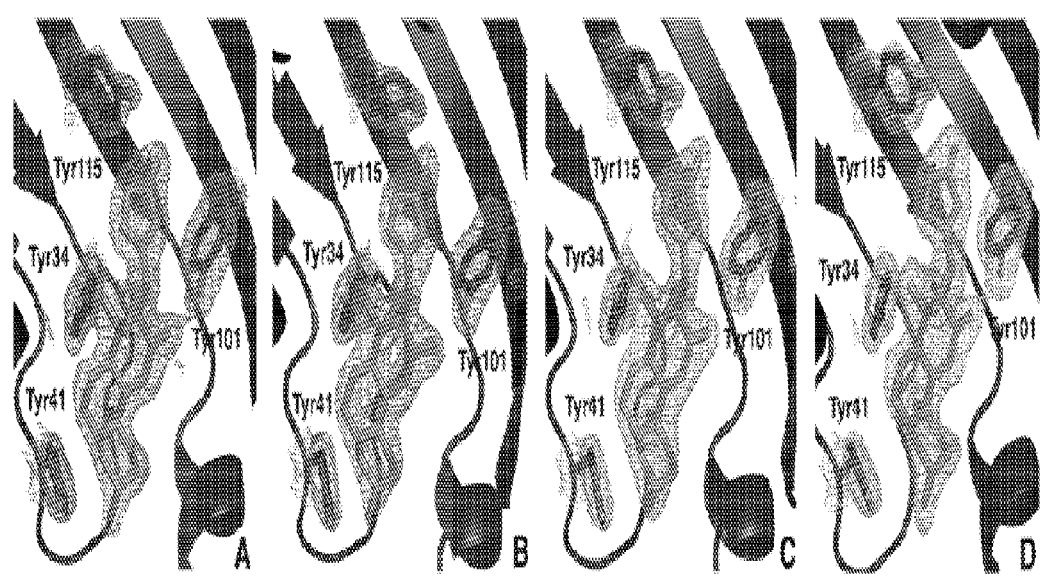

FIG. 17. Ligand binding site 2F$_o$-F$_c$ maps of the DIG10.2-DIG complex. 2F$_o$-F$_c$ omit map electron density of DIG interacting with Tyr34, Tyr41. Tyr101, and Tyr115 in chains A, B, C, and D contoured at 1.0 sigma.

Figure 18:
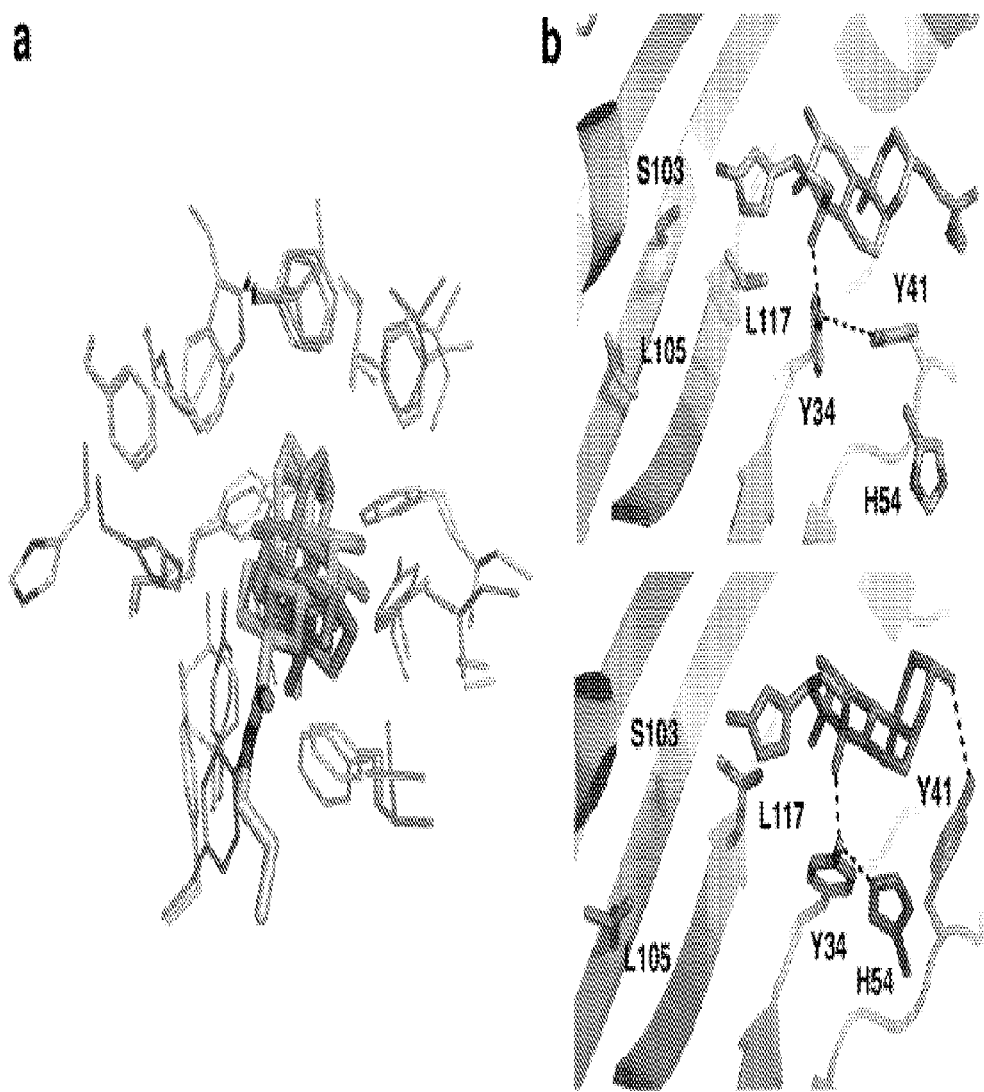

FIG. 18. Comparison of the side chain rotamers in the DIG10.2-DIG crystal structure versus the computational model. a, A backbone superposition of the computational model (gray) and the x-ray crystal structure of DIG10.2 shows that the majority of the amino acid side chains in the binding cavity adopt their modeled conformations. b, A side-by-side comparison of the computational model (top panel) and the x-ray crystal structure (bottom panel) of DIG10.2 highlighting the conformations of the six incorrectly modeled amino acids. Tyr34 adopts a statistically less probable rotamer (chi2=153°) in the crystal structure than the computational model (chi2=80°), which may result from an unanticipated hydrogen bond with His54: a subtle shift in the backbone position of this histidine allows it to face inwards towards the binding cavity and interact with Tyr34 instead of being fully solvent-exposed as predicted by the model. Perhaps to relieve hydrophobic clashes with the crystallographic Tyr34 rotamer, Leu117 also has a different side conformation. Finally, Try41, which engages in a second shell hydrogen-bonding interaction with Tyr34 in the computational model, adopts a different chi1 rotamer, and instead participates in a long (3.6 Å) hydrogen bond with the A-ring hydroxyl group of DIG. Ser103 and Leu105 also show different conformations in the structure and the computational model, but these residues are characterized by high conformational heterogeneity between the four protomers in the crystallographic asymmetric unit (see FIG. 3e).

Figure 19:
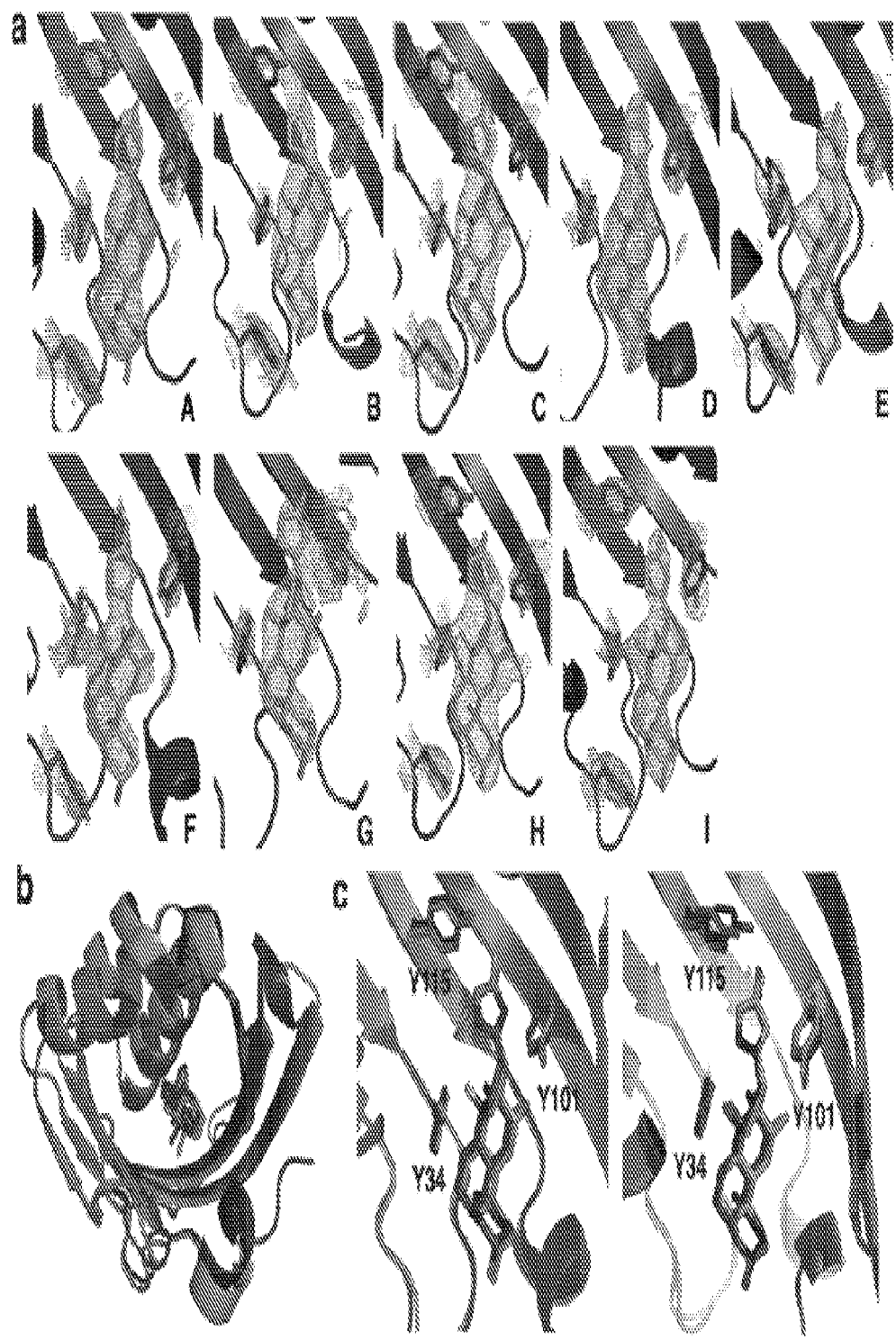

FIG. 19. Crystal structure of the DIG10.3-DIG complex. a, 2F$_o$-F$_c$ omit map electron density of DIG and hydrogen-bonding residues Tyr34, Tyr41, Tyr101, and Tyr115 in chains A though I of the DIG10.3-DIG crystal structure contoured at 1.0 sigma. At this contour level and poor resolution (3.2 Å), density is not observed for all hydrogen bonding residues in all crystallographic copies of the protein. b, Backbone binding site superposition of the crystal structures of DIG10.3 and DIG10.2. c, Backbone binding site superposition of the crystal structures of DIG10.3 and DIG10.2 chains A (left) and B (right). The DIG10.3 Tyr115 rotamer is similar to that observed in DIG10.2 chains A, C, and D but different from that observed in chain B. In DIG10.3 and chains A, C, and D of DIG10.2, the hydroxyl group of Tyr115 is plane with the lactone ring (~5° torsion), but in DIG10.2 chain B, it is out of plane (−70° torsion) and therefore expected to make a weaker interaction.

Figure 20:
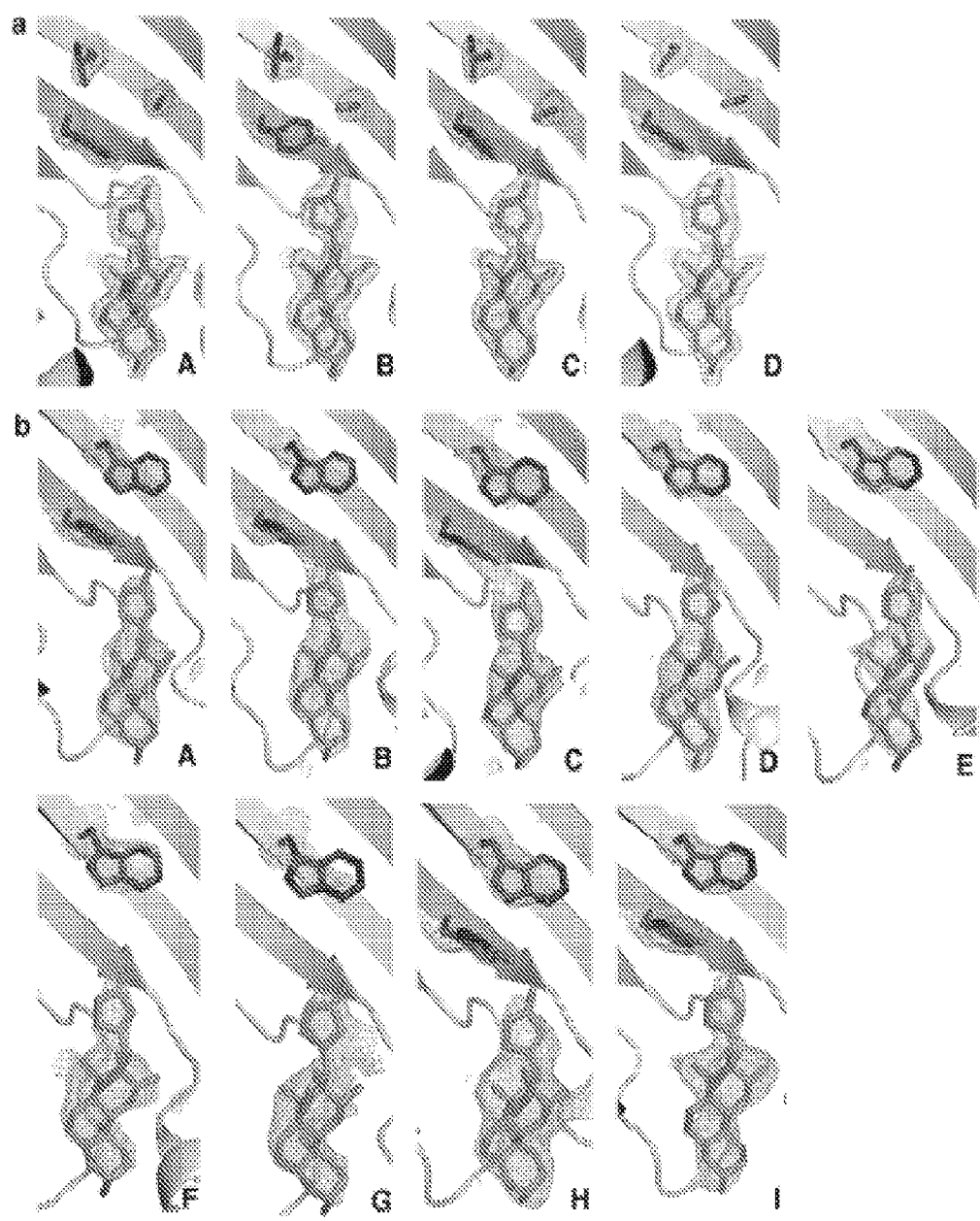

FIG. 20. Side chain conformational heterogeneity in the crystal structures of DIG10.2-DIG and DIG10.3-DIG. a, 2F$_o$-F$_c$ omit map electron density of DIG, Tyr115, Leu105, and S103 in chains A through D of the DIG10.2-DIG crystal structure contoured at 1.0 sigma. Tyr115, Leu105, and S103 all explore more than one rotameric conformation. b, 2F$_o$-F$_c$ omit map electron density of DIG, Tyr115 and Trp105 in chains A though I of the DIG10.3-DIG crystal structure contoured at 1.0 sigma. At this contour level and poor resolution (3.2 Å), density for Try115 is only observed in five of the nine copies; however, for copies in which density is observed, this amino acid is clearly in the same conformation. The position of Trp05, which is the same in all nine crystallographic copies, is inconsistent with the alternative conformation of Tyr115 observed in chain B of DIG10.2-DIG. These data suggest that DIG10.3 is more ordered than DIG10.2.

Figure 21A:
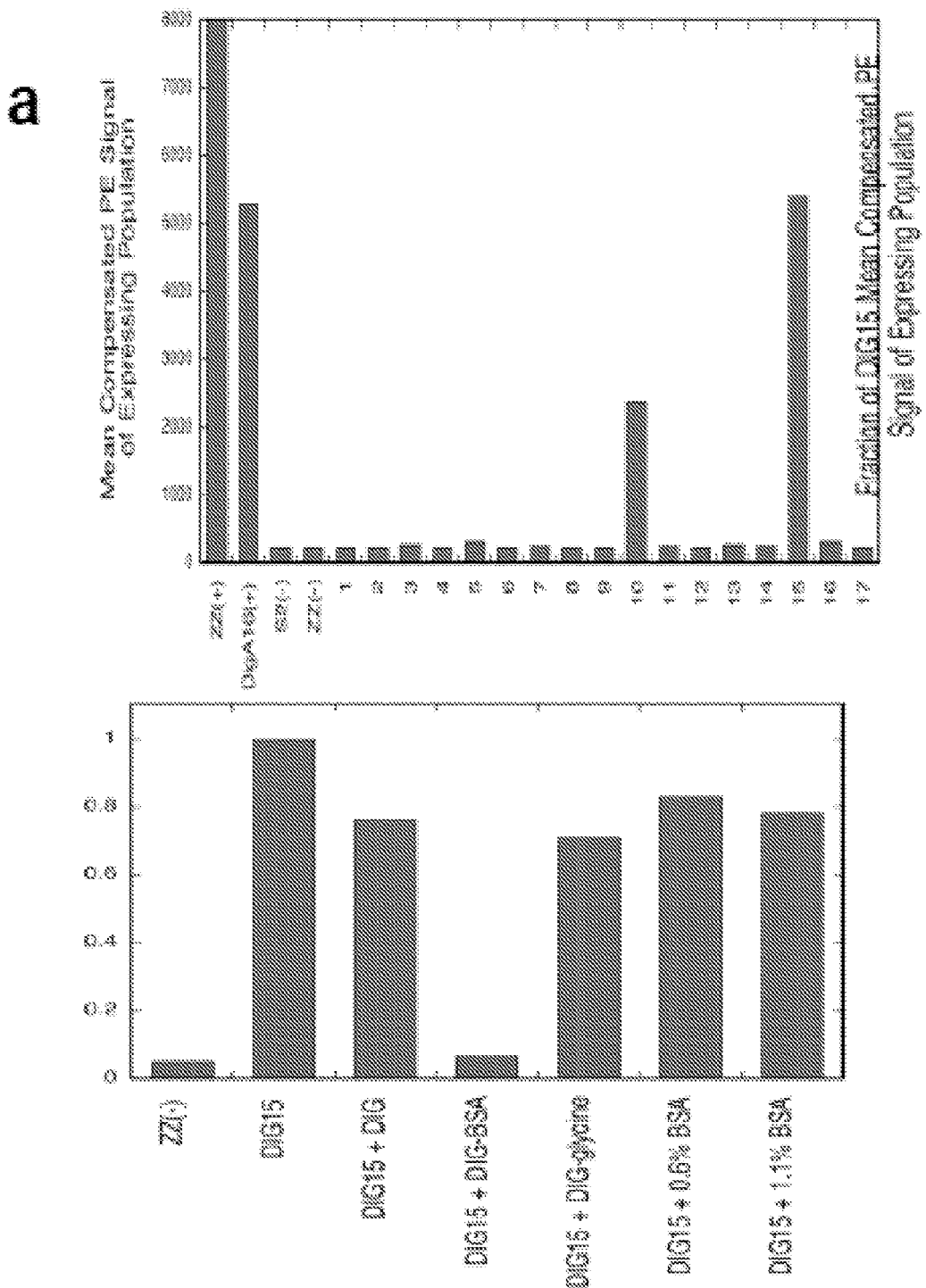
Figure 21B:
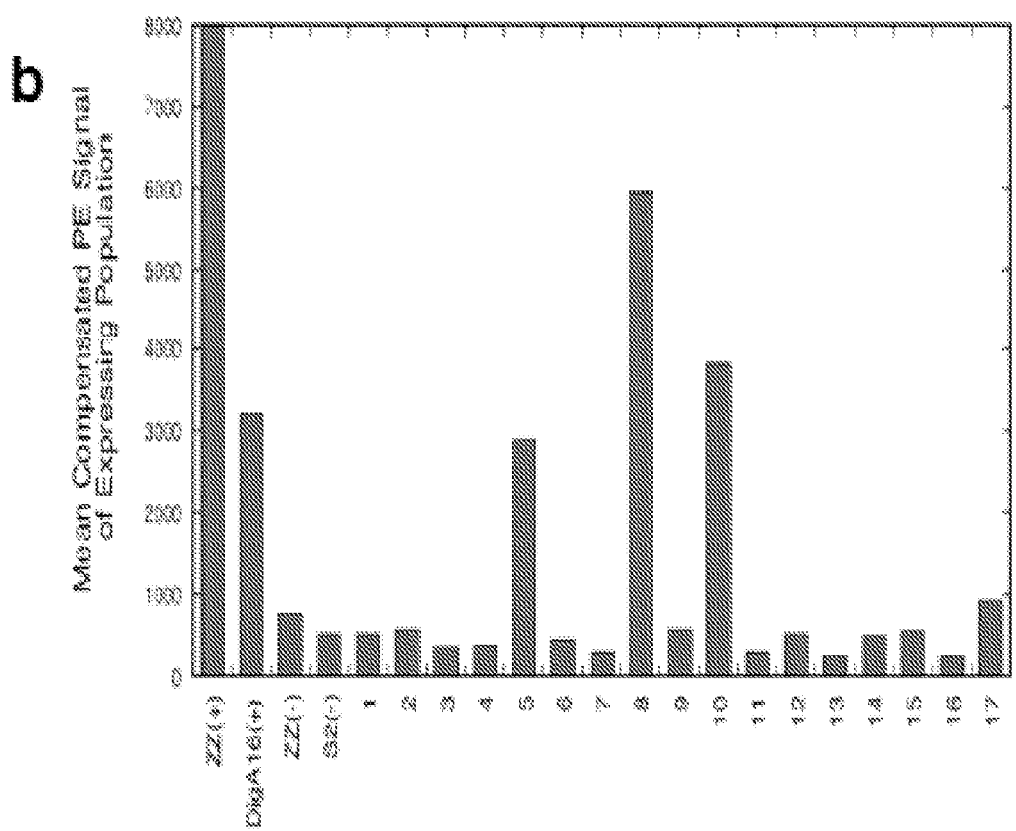

FIG. 21. CD Spectra of DIG10-based proteins. a, CD wavelength scan of DIG10.1a-TEV-his$_6$ at 25° C. (left panel) and 70° C. (right panel). Protein was prepared in PBS, pH 7.5. The protein exhibits α/β character expected from the structure. At temperatures above 65° C., the protein shows greater R-sheet character. b, Temperature melting curves of DIG10.1a-TEV-his$_6$ DIG10.2-TEV-his$_6$, DIG10.3-TEV-his$_6$, and 1z1s-TEV-his$_6$. Proteins are all stable at temperatures below 60° C. DIG10.3-TEV-his$_6$ does not unfold, even at 95° C.

FIG. 22. Sequence Alignment of DIG10-based Designs. Binding site residues are highlighted. Residues in magenta represent designed amino acids that differ from the scaffold 1z1s. Other colored residues indicate residues that evolved during affinity maturation to yield DIG10.1, DIG10.2, and DIG10.3, respectively. The three hydrogen-bonding tyrosines are marked with a star.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique.* 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe: F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides isolated polypeptides comprising or consisting of an amino acid sequence according to SEQ ID NO: 1, wherein the amino acid sequence is at least 70% identical to the amino acid sequence of SEQ ID NO: 15, (DIG10.3), and wherein the amino acid sequence is not the amino acid sequence of SEQ ID NO: 24 (PDB ID 1z1s):

MNAKEILVHSLRLLENGDARGWCDLFHPEGVLEFPYAPPGWKIRFEGRET

IWAHMRLFPEHLTVRFTDVQFYETADPDLAIGEFHGDCWATVSGGKLAQD

YISVIRTRDGQILLYRDEWNPLRITLEALGGVEAAAKIVQGA)

TABLE 1

| SEQ ID NO: 1 | | | |
|---|---|---|---|
| Residue # | Alignment AA | Specificity | Alternative residues |
| 1 | M | White/unlabeled: | Hydrophobic or absent |
| 2 | N | Green: | Any amino acid |
| 3 | A | White/unlabeled.: | Hydrophobic AAs |
| 4 | K | Green: | Any amino acid |
| 5 | E | Green: | Any amino acid |
| 6 | I | White/unlabeled: | Hydrophobic AAs |
| 7 | V | White/unlabeled: | Hydrophobic AAs |
| 8 | V | Green: | Any amino acid |
| 9 | H | Green: | Any amino acid |
| 10 | S, A | Gray/aqua - | Any amino acid |
| 11 | L | White/unlabeled: | Hydrophobic AAs |
| 12 | R | Green: | Any amino acid |
| 13 | L | White/unlabeled: | Any amino acid |
| 14 | L | White/unlabeled: | Hydrophobic AAs |
| 15 | E | Green: | Any amino acid |
| 16 | N | Green: | Any amino acid |
| 17 | G | White/unlabeled: | G, A, or S |
| 18 | D | Green: | Any amino acid |
| 19 | A | White/unlabeled: | Hydrophobic AAs |
| 20 | R | Green: | Any amino acid |
| 21 | G | Green | Any amino acid |
| 22 | W | White/unlabeled: | Aromatic/Polar neutral AAs |
| 23 | C, S | Gray/aqua - | Any amino acid |
| 24 | D | Green: | Any amino acid |
| 25 | L | White/unlabeled: | Hydrophobic AAs |
| 26 | F | White/unlabeled: | Hydrophobic AAs |
| 27 | H | Green: | Any amino acid |
| 28 | P | White/unlabeled: | Hydrophobic AAs |
| 29 | E | Green: | Any amino acid |
| 30 | G | White/unlabeled: | G, A, or S |
| 31 | V | Green: | Any amino acid |
| 32 | L | White/unlabeled: | Hydrophobic or Polar neutral AAs |
| 33 | E | Green: | Any amino acid |
| 34 | Y | Pink: | Aromatic |
| 35 | P | White/unlabeled: | Hydrophobic AAs |
| 36 | Y | Dark green: | Polar neutral |
| 37 | A, P | Gray/aqua - | Any amino acid |
| 38 | P | White/unlabeled: | Hydrophobic |
| 39 | P | White/unlabeled: | Hydrophobic AAs |
| 40 | G | White/unlabeled: | Hydrophobic AAs or G |
| 41 | H, Y | Gray/aqua - | Any amino acid |
| 42 | K | Green: | Any amino acid |
| 43 | T | White/unlabeled: | Polar neutral AAs |
| 44 | R | Green: | Any amino acid |
| 45 | F | White/unlabeled: | Hydrophobic or polar neutral AAs |
| 46 | E | Green: | Any amino acid |
| 47 | G | White/unlabeled: | G, A, or S |
| 48 | R | Green: | Any amino acid |
| 49 | E | Green: | Any amino acid |
| 50 | T | Green: | Any amino acid |
| 51 | I | White/unlabeled: | Hydrophobic AAs |
| 52 | W | Green: | Any amino acid |
| 53 | A | Green: | Any amino acid |
| 54 | H | White/unlabeled: | Basic, hydrophobic, or polar neutral AAs |
| 55 | M | White/unlabeled: | Hydrophobic |
| 56 | R | Green: | Any amino acid |
| 57 | L | Green: | Any amino acid |
| 58 | F | White/unlabeled: | Hydrophobic, basic, or polar neutral AAs |
| 59 | P | White/unlabeled: | Hydrophobic AAs |
| 60 | E | Green: | Any amino acid |
| 61 | Y | Green: | Any amino acid |
| 62 | V, M | Gray/aqua - | Hydrophobic AAs |
| 63 | T | Green: | Any AA |
| 64 | V, I | Gray/aqua - | Any amino acid |
| 65 | R | Green: | Any amino acid |
| 66 | F | White/unlabeled: | Hydrophobic AAs |
| 67 | T | Green: | Any amino acid |
| 68 | D | Green: | Any amino acid |
| 69 | V | White/unlabeled: | Hydrophobic AAs |
| 70 | Q | Green: | Any amino acid |
| 71 | F | White/unlabeled: | Hydrophobic AAs |

TABLE 1-continued

SEQ ID NO: 1

| Residue # | Alignment AA | Specificity | Alternative residues |
|---|---|---|---|
| 72 | Y | Dark green: | Aromatic AAs |
| 73 | E | Green: | Any amino acid |
| 74 | T | White/unlabeled: | Polar neutral AAs |
| 75 | A | Green: | Any amino acid |
| 76 | D | Green: | Any amino acid |
| 77 | P | White/unlabeled: | Hydrophobic AAs |
| 78 | D | Green: | Any amino acid |
| 79 | L | Green: | Any amino acid |
| 80 | A | White/unlabeled: | Hydrophobic AAs |
| 81 | I | Dark green: | Aliphatic AAs |
| 82 | G | White/unlabeled: | G, A, or S |
| 83 | E | Dark Lueen: | Acidic AAs |
| 84 | F | White/unlabeled: | Hydrophobic or charged AAs |
| 85 | H | Green: | Any amino acid |
| 86 | G | White/unlabeled: | Hydrophobic or polar neutral AAs |
| 87 | D | Green: | Any amino acid |
| 88 | G | White/unlabeled: | Hydrophobic or polar neutral |
| 89 | V | Green: | Any amino acid |
| 90 | H, L | Gray/aqua - | Any amino acid |
| 91 | T | Green: | Any amino acid |
| 92 | V, A | Gray/aqua - | Any amino acid |
| 93 | S | Green: | Any amino acid |
| 94 | G | Green: | Any amino acid |
| 95 | G | Green: | Any amino acid |
| 96 | K | Green: | Any amino acid |
| 97 | L | White/unlabeled: | Hydrophobic or polar neutral AAs |
| 98 | A | Green: | Any amino acid |
| 99 | A, Y | Gray/aqua - | Any amino acid |
| 100 | D | Green: | Any amino acid |
| 101 | Y | Pink: | Hydrophobic or basic AAs |
| 102 | I | Dark green: | Aliphatic AAs |
| 103 | S, A | Gray/aqua - | Any amino acid |
| 104 | V | Dark green: | Aliphatic AAs |
| 105 | L, W | Gray/aqua - | Any amino acid |
| 106 | R | Green: | Any amino acid |
| 107 | T | White/unlabeled: | Polar neutral AAs or hydrophobic residues |
| 108 | R | Green: | Any amino acid |
| 109 | D | Green: | Any amino acid |
| 110 | G | White/unlabeled: | G, A, or S |
| 111 | Q | Green: | Any amino acid |
| 112 | I | White/unlabeled: | Hydrophobic, polar neutral, or basic AAs |
| 113 | L | Green: | Any amino acid |
| 114 | L | Green: | Any amino acid |
| 115 | V | Pink: | Hydrophobic |
| 116 | R | Dark green: | Basic AAs |
| 117 | V, L | Gray/aqua - | Any amino acid |
| 118 | F | Dark green: | Aromatic AAs |
| 119 | F | White/unlabeled: | Aromatic, polar neutral, or basic |
| 120 | N | Dark green: | Polar neutral AAs |
| 121 | P | White/unlabeled: | Hydrophobic AAs |
| 122 | L | Dark green: | Aliphatic AAs |
| 123 | R | Green: | Any amino acid |
| 124 | V | White/unlabeled: | Hydrophobic, polar neutral, acidic |
| 125 | L | White/unlabeled: | Aliphatic As |
| 126 | E | Green: | Any amino acid |
| 127 | A, P | Gray/aqua - | Any amino acid |
| 128 | L | Green: | Any amino acid |
| 129 | G | Green: | Any amino acid |

As described in the examples that follow, the inventors describe a general method for the computational design of small molecule binding sites with pre-organized hydrogen bonding and hydrophobic interfaces and high overall shape complementary to the ligand, and use it to design the polypeptides of the present invention that are high affinity polypeptide ligands of the steroid digoxigenin (DIG) or the related steroids digitoxigenin, progesterone, and β-estradiol, as well as digoxin. The inventors have identified positions of the polypeptides of the invention that provide specificity of the polypeptides for DIG or one or more of the related steroids. As such, the polypeptides of the invention can be used, for example, in steroid biosensors and diagnostics, as well as for therapeutic applications. For example, digoxigenin (DIG), is the aglycone of digoxin, a cardiac glycoside used to treat heart disease. Digoxin has a narrow therapeutic window, and thus the polypeptides of the invention can be used, for example treat digoxin overdoses. The polypeptides can also be used, for example, to detect DIG and/or one or more of the related steroids. The polypeptides of the invention provide a cheaper, more selective alternative to currently used digoxigenin binding antibodies, which are costly to produce and are not selective for digoxigenin over other steroids. The polypeptides of the invention can also be used for in vivo biosensing applications, whereas the antibodies cannot because of their structurally necessary disulfide bonds and difficulty to express robustly.

The polypeptides of the invention are non-naturally occurring polypeptides designed using the computational methods of the invention (described herein). The starting polypeptide was SEQ ID NO: 24 (PDB ID 1z1s), which is a hypothetical protein from *Pseudomonas aeruginosa*. Thus, the polypeptides of the invention do not comprise or consist of SEQ ID NO: 24. Of the specific polypeptides tested, the polypeptide of SEQ ID NO: 15, (DIG10.3) was the best binder. Thus, the polypeptides of the invention are at least 70% identical with to the amino acid sequence of SEQ ID NO:15, over its full length. In various embodiments, the polypeptides of the invention are at least 75%, 80%, 85%, 90%, 91%, 92%, 93%, 94%, 95%, 96%, 97%, 98%, or 99% identical with to the amino acid sequence of SEQ ID NO:15, over its full length.

SEQ ID NO:1 is presented in Table 1, which includes the following information:

(a) "Residue number": Position in the polypeptide amino acid sequence;

(b) "Alignment amino acid": Residues that are in exemplary polypeptides;

(c) Specificity: Indication of toleration for amino acid substitution at the specific residue based on biochemical analysis; and (d) Alternative residues: Tolerated residues at the position based on deep mutational scanning analysis.

As used herein, the amino acid residues are abbreviated as follows: alanine (Ala, A), asparagine (Asn; N), aspartic acid (Asp; D), arginine (Arg; R), cysteine (Cys; C), glutamic acid (Glu; E), glutamine (Gin; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val: V).

Deep mutational scanning of DIG10.1 (SEQ ID NO: 13) was carried out to reveal all point mutations that will preserve or enhance function ($\Delta E \geq 0$) and those that negatively affect function ($\Delta E \leq 0$). This data is summarized in the "Specificity" section of Table 1, with the recited colors representing the following information:

Gray/aqua—positions that differ between the DIG10 series constructs described and tested in the examples that follow;

Pink: Mutation of these residues switches the steroid specificity profile of the polypeptides. Only conservative substitutions permitted;

Green: Surface residues not at critical dimer interface; these can be mutated without affecting function; and Dark green: Surface residues at dimer interface; conservative substitutions permitted White/unlabeled: Active site/core residues, conservative substitutions permitted.

Thus, some residues can be substituted with any amino acid, and thus the "alternative residues" noted in the Tables herein are listed as "any amino acid." Other positions can only tolerate conservative substitutions, and thus the "alternative residues" for these positions will define one or more amino acid grouping, as noted in the Tables herein. These amino acid groupings are defined as follows:

Polar neutral AA's: H, N, Q, Y, T, S, and C;
Hydrophobic AA's: A, I, L, V, M, F, W, P, and G:
  Aliphatic AA's (subset of hydrophobic AA's): A, I, L, V, and M;
  Aromatic AA's (subset of hydrophobic AA's): Y, W, and F;
Charged AA's: K, R, D, E, and H:
  Basic AA's (subset of charged AA's): K and R; and
  Acidic AA's (subset of charged AA's): D and E.

In one embodiment, the isolated polypeptides comprise or consist of the amino acid sequence of SEQ ID NO: 2 (Table 2). In this embodiment, the specificity defining residues ("pink") are limited to those residues in the polypeptides that have been made and tested in the examples that follow. As is shown in the examples, modifications at these positions (residues 34, 101, and 115) between Y and F change the steroid specificity profile of the resulting polypeptide.

TABLE 2

SEQ ID NO: 2

| Residue # | Alignment AA | Specificity | Alternative residues |
|---|---|---|---|
| 1 | M | White/unlabeled: | Hydrophobic or absent |
| 2 | N | Green: | Any amino acid |
| 3 | A | White/unlabeled: | Hydrophobic AAs |
| 4 | K | Green: | Any amino acid |
| 5 | E | Green: | Any amino acid |
| 6 | I | White/unlabeled: | Hydrophobic AAs |
| 7 | V | White/unlabeled: | Hydrophobic AAs |
| 8 | V | Green: | Any amino acid |
| 9 | H | Green: | Any amino acid |
| 10 | S, A | Gray/aqua- | Any amino acid |
| 11 | L | White/unlabeled: | Hydrophobic AAs |
| 12 | R | Green: | Any amino acid |
| 13 | L | White/unlabeled: | Any amino acid |
| 14 | L | White/unlabeled: | Hydrophobic AAs |
| 15 | E | Green: | Any amino acid |
| 16 | N | Green: | Any amino acid |
| 17 | G | White/unlabeled: | G, A, or S |
| 18 | D | Green: | Any amino acid |
| 19 | A | White/unlabeled: | Hydrophobic AAs |
| 20 | R | Green: | Any amino acid |
| 21 | G | Green | Any amino acid |
| 22 | W | White/unlabeled: | Aromatic/Polar neutral AAs |
| 23 | C, S | Gray/aqua- | Any amino acid |
| 24 | D | Green: | Any amino acid |
| 25 | L | White/unlabeled.: | Hydrophobic AAs |
| 26 | F | White/unlabeled: | Hydrophobic AAs |
| 27 | H | Green: | Any amino acid |
| 28 | P | White/unlabeled: | Hydrophobic AAs |
| 29 | E | Green: | Any amino acid |
| 30 | G | White/unlabeled: | G, A, or S |
| 31 | V | Green: | Any amino acid |
| 32 | L | White/unlabeled: | Hydrophobic or Polar neutral AAs |
| 33 | F | Green: | Any amino acid |
| 34 | Y | Pink: | F or Y |
| 35 | P | White/unlabeled: | Hydrophobic AAs |
| 36 | Y | Dark green: | Polar neutral |
| 37 | A, P | Gray/aqua- | Any amino acid |
| 38 | P | White/unlabeled: | Hydrophobic |
| 39 | P | White/unlabeled: | Hydrophobic AAs |
| 40 | G | White/unlabeled: | Hydrophobic AAs or G |

TABLE 2-continued

SEQ ID NO: 2

| Residue # | Alignment AA | Specificity | Alternative residues |
|---|---|---|---|
| 41 | H, Y | Gray/aqua- | Any amino acid |
| 42 | K | Green: | Any amino acid |
| 43 | T | White/unlabeled: | Polar neutral AAs |
| 44 | R | Green: | Any amino acid |
| 45 | F | White/unlabeled: | Hydrophobic or polar neutral AAs |
| 46 | E | Green: | Any amino acid |
| 47 | G | White/unlabeled: | G, A, or S |
| 48 | R | Green: | Any amino acid |
| 49 | E | Green: | Any amino acid |
| 50 | T | Green: | Any amino acid |
| 51 | I | White/unlabeled: | Hydrophobic AAs |
| 52 | W | Green: | Any amino acid |
| 53 | A | Green: | Any amino acid |
| 54 | H | White/unlabeled: | Basic, hydrophobic, or polar neutral AAs |
| 55 | M | White/unlabeled: | Hydrophobic |
| 56 | R | Green: | Any amino acid |
| 57 | L | Green: | Any amino acid |
| 58 | F | White/unlabeled: | Hydrophobic, basic, or polar neutral AAs |
| 59 | P | White/unlabeled: | Hydrophobic AAs |
| 60 | E | Green: | Any amino acid |
| 61 | Y | Green: | Any amino acid |
| 62 | V, M | Gray/aqua- | Hydrophobic AAs |
| 63 | T | Green: | Any AA |
| 64 | V, I | Gray/aqua- | Any amino acid |
| 65 | R | Green: | Any amino acid |
| 66 | F | White/unlabeled: | Hydrophobic AAs |
| 67 | T | Green: | Any amino acid |
| 68 | D | Green: | Any amino acid |
| 69 | V | White/unlabeled: | Hydrophobic AAs |
| 70 | Q | Green: | Any amino acid |
| 71 | F | White/unlabeled: | Hydrophobic AAs |
| 72 | Y | Dark green: | Aromatic AAs |
| 73 | E | Green: | Any amino acid |
| 74 | T | White/unlabeled: | Polar neutral AAs |
| 75 | A | Green: | Any amino acid |
| 76 | D | Green: | Any amino acid |
| 77 | P | White/unlabeled: | Hydrophobic AAs |
| 78 | D | Green: | Any amino acid |
| 79 | L | Green: | Any amino acid |
| 80 | A | White/unlabeled: | Hydrophobic AAs |
| 81 | I | Dark green: | Aliphatic AAs |
| 82 | G | White/unlabeled: | G, A, or S |
| 83 | E | Dark green: | Acidic AAs |
| 84 | F | White/unlabeled: | Hydrophobic or charged AAs |
| 85 | H | Green: | Any amino acid |
| 86 | G | White/unlabeled: | Hydrophobic or polar neutral AAs or G |
| 87 | D | Green: | Any amino acid |
| 88 | G | White/unlabeled: | Hydrophobic or polar neutral |
| 89 | V | Green: | Any amino acid |
| 90 | H, L | Gray/aqua- | Any amino acid |
| 91 | T | Green: | Any amino acid |
| 92 | V, A | Gray/aqua- | Any amino acid |
| 93 | S | Green: | Any amino acid |
| 94 | G | Green: | Any amino acid |
| 95 | G | Green: | Any amino acid |
| 96 | K | Green: | Any amino acid. |
| 97 | L | White/unlabeled: | Hydrophobic or polar neutral AAs |
| 98 | A | Green: | Any amino acid |
| 99 | A, Y | Gray/aqua- | Any amino acid |
| 100 | D | Green: | Any amino acid |
| 101 | Y | Pink: | F or Y |
| 102 | I | Dark green: | Aliphatic AAs |
| 103 | S, A | Gray/aqua- | Any amino acid |
| 104 | V | Dark green: | Aliphatic AAs |
| 105 | L, W | Gray/aqua- | Any amino acid |
| 106 | R | Green: | Any amino acid |
| 107 | T | White/unlabeled: | Polar neutral AAs or hydrophobic residues |
| 108 | R | Green: | Any amino acid |

TABLE 2-continued

SEQ ID NO: 2

| Residue # | Alignment AA | Specificity | Alternative residues |
|---|---|---|---|
| 109 | D | Green: | Any amino acid |
| 110 | G | White/unlabeled: | G, A, or S |
| 111 | Q | Green: | Any amino acid |
| 112 | I | White/unlabeled: | Hydrophobic, polar neutral, or basic AAs |
| 113 | L | Green: | Any amino acid |
| 114 | L | Green: | Any amino acid |
| 115 | Y | Pink: | F or Y |
| 116 | R | Dark green: | Basic AAs |
| 117 | V, L | Gray/aqua- | Any amino acid |
| 118 | F | Dark green: | Aromatic AAs |
| 119 | F | White/unlabeled: | Aromatic, polar neutral, or basic |
| 120 | N | Dark green: | Polar neutral AAs |
| 121 | P | White/unlabeled: | Hydrophobic AAs |
| 122 | L | Dark green: | Aliphatic AAs |
| 123 | R | Green: | Any amino acid |
| 124 | V | White/unlabeled: | Hydrophobic, polar neutral, acidic |
| 125 | L | White/unlabeled: | Aliphatic AAs |
| 126 | E | Green: | Any amino acid |
| 127 | A, P | Gray/aqua- | Any amino acid |
| 128 | L | Green: | Any amino acid |
| 129 | G | Green: | Any amino acid |

In a further embodiment, the isolated polypeptides comprise or consist of the amino acid sequence of SEQ ID NO: 3 (Table 3). This embodiment differs from SEQ ID NO:2 (Table 2) in that the surface residues at the dimer interface ("dark green") are limited to those residues in the polypeptides that have been made and tested in the examples that follow.

TABLE 3

SEQ ID NO: 3

| Residue # | Alignment AA | Specificity | Alternative residues |
|---|---|---|---|
| 1 | M | White/unlabeled: | Hydrophobic or absent |
| 2 | N | Green: | Any amino acid |
| 3 | A | White/unlabeled: | Hydrophobic AAs |
| 4 | K | Green: | Any amino acid |
| 5 | E | Green: | Any amino acid |
| 6 | I | White/unlabeled: | Hydrophobic AAs |
| 7 | V | White/unlabeled: | Hydrophobic AAs |
| 8 | V | Green: | Any amino acid |
| 9 | H | Green: | Any amino acid |
| 10 | S, A | Gray/aqua- | Any amino acid |
| 11 | L | White/unlabeled: | Hydrophobic AAs |
| 12 | R | Green: | Any amino acid |
| 13 | L | White/unlabeled: | Any amino acid |
| 14 | L | White/unlabeled: | Hydrophobic AAs |
| 15 | E | Green: | Any amino acid |
| 16 | N | Green: | Any amino acid |
| 17 | G | White/unlabeled: | G, A, or S |
| 18 | D | Green: | Any amino acid |
| 19 | A | White/unlabeled: | Hydrophobic AAs |
| 20 | R | Green: | Any amino acid |
| 21 | G | Green | Any amino acid |
| 22 | W | White/unlabeled: | Aromatic/Polar neutral AAs |
| 23 | C, S | Gray/aqua- | Any amino acid |
| 24 | D | Green: | Any amino acid |
| 25 | L | White/unlabeled: | Hydrophobic AAs |
| 26 | F | White/unlabeled: | Hydrophobic AAs |
| 27 | H | Green: | Any amino acid |
| 28 | P | White/unlabeled: | Hydrophobic AAs |
| 29 | E | Green: | Any amino acid |
| 30 | G | White/unlabeled: | G, A, or S |
| 31 | V | Green: | Any amino acid |
| 32 | L | White/unlabeled: | Hydrophobic or Polar neutral AAs |
| 33 | E | Green: | Any amino acid |

TABLE 3-continued

SEQ ID NO: 3

| Residue # | Alignment AA | Specificity | Alternative residues |
|---|---|---|---|
| 34 | Y | Pink: | F or Y |
| 35 | P | White/unlabeled: | Hydrophobic AAs |
| 36 | Y | Dark green: | Y |
| 37 | A, P | Gray/aqua- | Any amino acid |
| 38 | P | White/unlabeled: | Hydrophobic |
| 39 | P | White/unlabeled: | Hydrophobic AAs |
| 40 | G | White/unlabeled: | Hydrophobic AAs or G |
| 41 | H, Y | Gray/aqua- | Any amino acid |
| 42 | K | Green: | Any amino acid |
| 43 | T | White/unlabeled: | Polar neutral AAs |
| 44 | R | Green: | Any amino acid |
| 45 | F | White/unlabeled: | Hydrophobic or polar neutral AAs |
| 46 | E | Green: | Any amino acid |
| 47 | G | White/unlabeled.: | G, A, or S |
| 48 | R | Green: | Any amino acid |
| 49 | E | Green: | Any amino acid |
| 50 | T | Green: | Any amino acid |
| 51 | I | White/unlabeled: | Hydrophobic AAs |
| 52 | W | Green: | Any amino acid |
| 53 | A | Green: | Any amino acid |
| 54 | H | White/unlabeled: | Basic, hydrophobic, or polar neutral AAs |
| 55 | M | White/unlabeled: | Hydrophobic |
| 56 | R | Green: | Any amino acid |
| 57 | L | Green: | Any amino acid |
| 58 | F | White/unlabeled: | Hydrophobic, basic, or polar neutral AAs |
| 59 | P | White/unlabeled.: | Hydrophobic AAs |
| 60 | E | Green: | Any amino acid |
| 61 | Y | Green: | Any amino acid |
| 62 | V, M | Gray/aqua- | Hydrophobic AAs |
| 63 | T | Green: | Any AA |
| 64 | V, I | Gray/aqua- | Any amino acid |
| 65 | R | Green: | Any amino acid |
| 66 | F | White/unlabeled: | Hydrophobic As |
| 67 | T | Green: | Any amino acid |
| 68 | D | Green: | Any amino acid |
| 69 | V | White/unlabeled: | Hydrophobic AAs |
| 70 | Q | Green: | Any amino acid |
| 71 | F | White/unlabeled: | Hydrophobic As |
| 72 | Y | Dark green: | Y |
| 73 | E | Green: | Any amino acid |
| 74 | T | White/unlabeled: | Polar neutral AAs |
| 75 | A | Green: | Any amino acid |
| 76 | D | Green: | Any amino acid |
| 77 | P | White/unlabeled: | Hydrophobic AAs |
| 78 | D | Green: | Any amino acid |
| 79 | L | Green: | Any amino acid |
| 80 | A | White/unlabeled.: | Hydrophobic AAs |
| 81 | I | Dark green: | I |
| 82 | G | White/unlabeled: | G, A, or S |
| 83 | E | Dark green: | E |
| 84 | F | White/unlabeled: | Hydrophobic or charged AAs |
| 85 | H | Green: | Any amino acid |
| 86 | G | White/unlabeled: | Hydrophobic or polar neutral AAs or G |
| 87 | D | Green: | Any amino acid |
| 88 | G | White/unlabeled: | Hydrophobic or polar neutral |
| 89 | V | Green: | Any amino acid |
| 90 | H, L | Gray/aqua- | Any amino acid |
| 91 | T | Green: | Any amino acid |
| 92 | V, A | Gray/aqua- | Any amino acid |
| 93 | S | Green: | Any amino acid |
| 94 | G | Green: | Any amino acid |
| 95 | G | Green: | Any amino acid |
| 96 | K | Green: | Any amino acid |
| 97 | L | White/unlabeled: | Hydrophobic or polar neutral AAs |
| 98 | A | Green: | Any amino acid |
| 99 | A, Y | Gray/aqua- | Any amino acid |
| 100 | D | Green: | Any amino acid |
| 101 | Y | Pink: | F or Y |
| 102 | I | Dark green: | I |
| 103 | S, A | Gray/aqua- | Any amino acid |

TABLE 3-continued

SEQ ID NO: 3

| Residue # | Alignment AA | Specificity | Alternative residues |
|---|---|---|---|
| 104 | V | Dark green: | V |
| 105 | L, W | Gray/aqua- | Any amino acid |
| 106 | R | Green: | Any amino acid |
| 107 | T | White/unlabeled: | Polar neutral AAs or hydrophobic residues |
| 108 | R | Green: | Any amino acid |
| 109 | D | Green: | Any amino acid |
| 110 | G | White/unlabeled: | G, A, or S |
| 111 | Q | Green: | Any amino acid |
| 112 | I | White/unlabeled: | Hydrophobic, polar neutral, or basic AAs |
| 113 | L | Green: | Any amino acid |
| 114 | L | Green: | Any amino acid |
| 115 | V | Pink: | F or Y |
| 116 | R | Dark green: | R |
| 117 | V, L | Gray/aqua- | Any amino acid |
| 118 | F | Dark green: | F |
| 119 | F | White/unlabeled: | Aromatic, polar neutral, or basic |
| 120 | N | Dark green: | N |
| 121 | P | White/unlabeled: | Hydrophobic AAs |
| 122 | L | Dark green: | L |
| 123 | R | Green: | Any amino acid |
| 124 | V | White/unlabeled: | Hydrophobic, polar neutral, acidic |
| 125 | L | White/unlabeled: | Aliphatic AAs |
| 126 | E | Green: | Any amino acid |
| 127 | A, P | Gray/aqua- | Any amino acid |
| 128 | L | Green: | Any amino acid |
| 129 | G | Green: | Any amino acid |

In another embodiment, the isolated polypeptides comprise or consist of the amino acid sequence of SEQ ID NO: 4 (Table 4). In this embodiment, the polypeptides differ from the polypeptides of SEQ ID NO: 3 (Table 3) in that the active/core site residues ("white") are more narrowly defined.

TABLE 4

SEQ ID NO: 4

| Residue # | Alignment AA | Specificity | Alternative residues |
|---|---|---|---|
| 1 | M | White/unlabeled: | Polar neutral AAs or Met |
| 2 | N | Green: | Any amino acid |
| 3 | A | White/unlabeled: | Aliphatic AAs |
| 4 | K | Green: | Any amino acid |
| 5 | E | Green: | Any amino acid |
| 6 | I | White/unlabeled: | Aliphatic AAs |
| 7 | V | White/unlabeled: | Aliphatic AAs |
| 8 | V | Green: | Any amino acid |
| 9 | H | Green: | Any amino acid |
| 10 | S, A | Gray/aqua- | Any amino acid |
| 11 | L | White/unlabeled: | Aliphatic AAs |
| 12 | R | Green: | Any amino acid |
| 13 | L | White/unlabeled: | Aliphatic acid |
| 14 | L | White/unlabeled: | Aliphatic AAs |
| 15 | E | Green: | Any amino acid |
| 16 | N | Green: | Any amino acid |
| 17 | G | White/unlabeled: | G, A, or S |
| 18 | D | Green: | Any amino acid |
| 19 | A | White/unlabeled: | Aliphatic AAs |
| 20 | R | Green: | Any amino acid |
| 21 | G | Green | Any amino acid |
| 22 | W | White/unlabeled: | Aromatic AAs |
| 23 | C, S | Gray/aqua- | Any amino acid |
| 24 | D | Green: | Any amino acid |
| 25 | L | White/unlabeled: | Aliphatic AAs |
| 26 | F | White/unlabeled: | Aromatic AAs |
| 27 | H | Green: | Any amino acid |
| 28 | P | White/unlabeled: | Hydrophobic As |
| 29 | E | Green: | Any amino acid |

TABLE 4-continued

SEQ ID NO: 4

| Residue # | Alignment AA | Specificity | Alternative residues |
|---|---|---|---|
| 30 | G | White/unlabeled: | G, A, or S |
| 31 | V | Green: | Any amino acid |
| 32 | L | White/unlabeled: | Aliphatic AAs |
| 33 | E | Green: | Any amino acid |
| 34 | Y | Pink: | F or Y |
| 35 | P | White/unlabeled: | Hydrophobic AAs |
| 36 | Y | Dark green: | Y |
| 37 | A, P | Gray/aqua- | Any amino acid |
| 38 | P | White/unlabeled: | Aliphatic or P |
| 39 | P | White/unlabeled: | Aliphatic AAs or P |
| 40 | G | White/unlabeled: | Aliphatic AAs or G |
| 41 | H, Y | Gray/aqua- | Any amino acid |
| 42 | K | Green: | Any amino acid |
| 43 | T | White/unlabeled: | Polar neutral AAs |
| 44 | R | Green: | Any amino acid |
| 45 | F | White/unlabeled: | Hydrophobic or polar neutral AAs |
| 46 | E | Green: | Any amino acid |
| 47 | G | White/unlabeled: | G, A, or S |
| 48 | R | Green: | Any amino acid |
| 49 | E | Green: | Any amino acid |
| 50 | T | Green: | Any amino acid |
| 51 | I | White/unlabeled: | Aliphatic AAs |
| 52 | W | Green: | Any amino acid |
| 53 | A | Green: | Any amino acid |
| 54 | H | White/unlabeled: | Basic, hydrophobic, or polar neutral AAs |
| 55 | M | White/unlabeled: | Hydrophobic |
| 56 | R | Green: | Any amino acid |
| 57 | L | Green: | Any amino acid |
| 58 | F | White/unlabeled: | Aromatic AAs |
| 59 | P | White/unlabeled: | Hydrophobic AAs |
| 60 | E | Green: | Any amino acid |
| 61 | Y | Green: | Any amino acid |
| 62 | V, M | Gray/aqua- | Hydrophobic AAs |
| 63 | T | Green: | Any AA |
| 64 | V, I | Gray/aqua- | Any amino acid |
| 65 | R | Green: | Any amino acid |
| 66 | F | White/unlabeled: | Aromatic AAs |
| 67 | T | Green: | Any amino acid |
| 68 | D | Green: | Any amino acid |
| 69 | V | White/unlabeled: | Aliphatic AAs |
| 70 | Q | Green: | Any amino acid |
| 71 | F | White/unlabeled: | Aromatic AAs |
| 72 | Y | Dark green: | Y |
| 73 | E | Green: | Any amino acid |
| 74 | T | White/unlabeled: | Polar neutral AAs |
| 75 | A | Green: | Any amino acid |
| 76 | D | Green: | Any amino acid |
| 77 | P | White/unlabeled: | Hydrophobic AAs |
| 78 | D | Green: | Any amino acid |
| 79 | L | Green: | Any amino acid |
| 80 | A | White/unlabeled: | Aliphatic AAs |
| 81 | I | Dark green: | I |
| 82 | G | White/unlabeled: | G, A, or S |
| 83 | E | Dark green: | E |
| 84 | F | White/unlabeled: | Aromatic AAs |
| 85 | H | Green: | Any amino acid |
| 86 | G | White/unlabeled: | Hydrophobic or polar neutral AAs or G |
| 87 | D | Green: | Any amino acid |
| 88 | G | White/unlabeled: | Hydrophobic or polar neutral |
| 89 | V | Green: | Any amino acid |
| 90 | H, L | Gray/aqua- | Any amino acid |
| 91 | T | Green: | Any amino acid |
| 92 | V, A | Gray/aqua- | Any amino acid |
| 93 | S | Green: | Any amino acid |
| 94 | G | Green: | Any amino acid |
| 95 | G | Green: | Any amino acid |
| 96 | K | Green: | Any amino acid |
| 97 | L | White/unlabeled: | Hydrophobic or polar neutral AAs |
| 98 | A | Green: | Any amino acid |
| 99 | A, Y | Gray/aqua- | Any amino acid |

TABLE 4-continued

SEQ ID NO: 4

| Residue # | Alignment AA | Specificity | Alternative residues |
|---|---|---|---|
| 100 | D | Green: | Any amino acid |
| 101 | Y | Pink: | F or Y |
| 102 | I | Dark green: | I |
| 103 | S, A | Gray/aqua- | Any amino acid |
| 104 | V | Dark green: | V |
| 105 | L, W | Gray/aqua- | Any amino acid |
| 106 | R | Green: | Any amino acid |
| 107 | T | White/unlabeled: | Polar neutral AAs |
| 108 | R | Green: | Any amino acid |
| 109 | D | Green: | Any amino acid |
| 110 | G | White/unlabeled: | G, A, or S |
| 111 | Q | Green: | Any amino acid |
| 112 | I | White/unlabeled: | Aliphatic AAs |
| 113 | L | Green: | Any amino acid |
| 114 | L | Green: | Any amino acid |
| 115 | Y | Pink: | F or Y |
| 116 | R | Dark green: | R |
| 117 | V, L | Gray/aqua- | Any amino acid |
| 118 | F | Dark green: | F |
| 119 | F | White/unlabeled: | Aromatic, polar neutral, or basic |
| 120 | N | Dark green: | N |
| 121 | P | White/unlabeled: | Hydrophobic AAs |
| 122 | L | Dark green: | L |
| 123 | R | Green: | Any amino acid |
| 124 | V | White/unlabeled: | Hydrophobic, polar neutral, acidic |
| 125 | L | White/unlabeled: | Aliphatic AAs |
| 126 | E | Green: | Any amino acid |
| 127 | A, P | Gray/aqua- | Any amino acid |
| 128 | L | Green: | Any amino acid |
| 129 | G | Green: | Any amino acid |

In another embodiment, the isolated polypeptides comprise or consist of the amino acid sequence of SEQ ID NO: 5 (Table 5). In this embodiment, the polypeptides differ from those of SEQ ID NO: 4 (Table 4) in that the active/core site residues ("white") are limited to specific amino acid residues identified in the mutational analysis as preserving or enhancing function in the deep mutational assay, and/or to residues present in the polypeptides made and tested.

TABLE 5

SEQ ID NO: 5

| Residue # | Alignment AA | Specificity | Alternative residues |
|---|---|---|---|
| 1 | M | White/unlabeled: | M or absent |
| 2 | N | Green: | Any amino acid |
| 3 | A | White/unlabeled: | A |
| 4 | K | Green: | Any amino acid |
| 5 | E | Green: | Any amino acid |
| 6 | I | White/unlabeled: | I |
| 7 | V | White/unlabeled: | V or L |
| 8 | V | Green: | Any amino acid |
| 9 | H | Green: | Any amino acid |
| 10 | S, A | Gray/aqua- | Any amino acid |
| 11 | L | White/unlabeled: | L |
| 12 | R | Green: | Any amino acid |
| 13 | L | White/unlabeled: | L |
| 14 | L | White/unlabeled: | L, I |
| 15 | E | Green: | Any amino acid |
| 16 | N | Green: | Any amino acid |
| 17 | G | White/unlabeled: | G |
| 18 | D | Green: | Any amino acid |
| 19 | A | White/unlabeled: | A |
| 20 | R | Green: | Any amino acid |
| 21 | G | Green | Any amino acid |
| 22 | W | White/unlabeled: | W, Y |
| 23 | C, S | Gray/aqua- | Any amino acid |
| 24 | D | Green: | Any amino acid |
| 25 | L | White/unlabeled: | L |
| 26 | F | White/unlabeled: | F, T, Y |
| 27 | H | Green: | Any amino acid |
| 28 | P | White/unlabeled: | P |
| 29 | E | Green: | Any amino acid |
| 30 | G | White/unlabeled: | G |
| 31 | V | Green: | Any amino acid |
| 32 | L | White/unlabeled: | L or S |
| 33 | E | Green: | Any amino acid |
| 34 | Y | Pink: | F or Y |
| 35 | P | White/unlabeled: | P |
| 36 | Y | Dark green: | Y |
| 37 | A, P | Gray/aqua- | Any amino acid |
| 38 | P | White/unlabeled: | P, V |
| 39 | P | White/unlabeled: | P |
| 40 | G | White/unlabeled: | G |
| 41 | H, Y | Gray/aqua- | Any amino acid |
| 42 | K | Green: | Any amino acid |
| 43 | T | White/unlabeled: | T |
| 44 | R | Green: | Any amino acid |
| 45 | F | White/unlabeled: | F, H, T, Y |
| 46 | E | Green: | Any amino acid |
| 47 | G | White/unlabeled: | G |
| 48 | R | Green: | Any amino acid |
| 49 | E | Green: | Any amino acid |
| 50 | T | Green: | Any amino acid |
| 51 | I | White/unlabeled: | I |
| 52 | W | Green: | Any amino acid |
| 53 | A | Green: | Any amino acid |
| 54 | H | White/unlabeled: | H, C, I, T |
| 55 | M | White/unlabeled: | M, F, I |
| 56 | R | Green: | Any amino acid |
| 57 | L | Green: | Any amino acid |
| 58 | F | White/unlabeled: | F, H, A, I, P, V, W |
| 59 | P | White/unlabeled: | P |
| 60 | E | Green: | Any amino acid |
| 61 | Y | Green: | Any amino acid |
| 62 | V, M | Gray/aqua- | Hydrophobic AAs |
| 63 | T | Green: | Any AA |
| 64 | V, I | Gray/aqua- | Any amino acid |
| 65 | R | Green: | Any amino acid |
| 66 | F | White/unlabeled: | F |
| 67 | T | Green: | Any amino acid |
| 68 | D | Green: | Any amino acid |
| 69 | V | White/unlabeled: | V |
| 70 | Q | Green: | Any amino acid |
| 71 | F | White/unlabeled: | F |
| 72 | Y | Dark green: | Y |
| 73 | E | Green: | Any amino acid |
| 74 | T | White/unlabeled: | T |
| 75 | A | Green: | Any amino acid |
| 76 | D | Green: | Any amino acid |
| 77 | P | White/unlabeled: | P |
| 78 | D | Green: | Any amino acid |
| 79 | L | Green: | Any amino acid |
| 80 | A | White/unlabeled: | A |
| 81 | I | Dark Green: | I |
| 82 | G | White/unlabeled: | G |
| 83 | E | Dark green: | E |
| 84 | F | White/unlabeled: | F, A, D, W, Y |
| 85 | H | Green: | Any amino acid |
| 86 | G | White/unlabeled: | F, I, L, T G |
| 87 | D | Green: | Any amino acid |
| 88 | G | White/unlabeled: | G, A, F, I, L, N |
| 89 | V | Green: | Any amino acid |
| 90 | H, L | Gray/aqua- | Any amino acid |
| 91 | T | Green: | Any amino acid |
| 92 | V, A | Gray/aqua- | Any amino acid |
| 93 | S | Green: | Any amino acid |
| 94 | G | Green: | Any amino acid |
| 95 | G | Green: | Any amino acid |
| 96 | K | Green: | Any amino acid |
| 97 | L | White/unlabeled: | I, F, L, M, S, T, W, Y |
| 98 | A | Green: | Any amino acid |
| 99 | A, Y | Gray/aqua- | Any amino acid |
| 100 | D | Green: | Any amino acid |

TABLE 5-continued

SEQ ID NO: 5

| Residue # | Alignment AA | Specificity | Alternative residues |
|---|---|---|---|
| 101 | Y | Pink: | F or Y |
| 102 | I | Dark green: | I |
| 103 | S, A | Gray/aqua- | Any amino acid |
| 104 | V | Dark green: | V |
| 105 | L, W | Gray/aqua- | Any amino acid |
| 106 | R | Green: | Any amino acid |
| 107 | T | White/unlabeled: | T |
| 108 | R | Green: | Any amino acid |
| 109 | D | Green: | Any amino acid |
| 110 | G | White/unlabeled: | G |
| 111 | Q | Green: | Any amino acid |
| 112 | I | White/unlabeled: | I |
| 113 | L | Green: | Any amino acid |
| 114 | L | Green: | Any amino acid |
| 115 | Y | Pink: | F or Y |
| 116 | R | Dark green: | R |
| 117 | V, L | Gray/aqua- | Any amino acid |
| 118 | F | Dark green: | F |
| 119 | F | White/unlabeled: | F, G, M, R, W |
| 120 | N | Dark green: | N |
| 121 | P | White/unlabeled: | P |
| 122 | L | Dark green: | L |
| 123 | R | Green: | Any amino acid |
| 124 | V | White/unlabeled: | V, E, F, I, N, P, R, S, W |
| 125 | L | White/unlabeled: | L |
| 126 | E | Green: | Any amino acid |
| 127 | A, P | Gray/aqua- | Any amino acid |
| 128 | L | Green: | Any amino acid |
| 129 | G | Green: | Any amino acid |

In another embodiment, the isolated polypeptides comprise or consist of the amino acid sequence of SEQ ID NO: 6 (Table 6). In this embodiment, polypeptides differ from those of SEQ ID NO: 5 (Table 5) in that the active/core site residues ("white") are limited to substitutions in the polypeptides made and tested in the examples that follow.

TABLE 6

SEQ ID NO: 6

| Residue # | Alignment AA | Specificity | Alternative residues |
|---|---|---|---|
| 1 | M | White/unlabeled: | M or absent |
| 2 | N | Green: | Any amino acid |
| 3 | A | White/unlabeled: | A |
| 4 | K | Green: | Any amino acid |
| 5 | E | Green: | Any amino acid |
| 6 | I | White/unlabeled: | I |
| 7 | V | White/unlabeled: | V or L |
| 8 | V | Green: | Any amino acid |
| 9 | H | Green: | Any amino acid |
| 10 | S, A | Gray/aqua- | Any amino acid |
| 11 | L | White/unlabeled: | L |
| 12 | R | Green: | Any amino acid |
| 13 | L | White/unlabeled: | L |
| 14 | L | White/unlabeled: | L |
| 15 | F | Green: | Any amino acid |
| 16 | N | Green: | Any amino acid |
| 17 | G | White/unlabeled: | G |
| 18 | D | Green: | Any amino acid |
| 19 | A | White/unlabeled: | A |
| 20 | R | Green: | Any amino acid |
| 21 | G | Green | Any amino acid |
| 22 | W | White/unlabeled: | W |
| 23 | C, S | Gray/aqua- | Any amino acid |
| 24 | D | Green: | Any amino acid |

TABLE 6-continued

SEQ ID NO: 6

| Residue # | Alignment AA | Specificity | Alternative residues |
|---|---|---|---|
| 25 | L | White/unlabeled: | L |
| 26 | F | White/unlabeled: | F |
| 27 | H | Green: | Any amino acid |
| 28 | P | White/unlabeled: | P |
| 29 | E | Green: | Any amino acid |
| 30 | G | White/unlabeled: | G |
| 31 | V | Green: | Any amino acid |
| 32 | L | White/unlabeled: | L |
| 33 | E | Green: | Any amino acid |
| 34 | Y | Pink: | F or Y |
| 35 | P | White/unlabeled: | P |
| 36 | Y | Dark green: | Y |
| 37 | A, P | Gray/aqua- | Any amino acid |
| 38 | P | White/unlabeled: | P |
| 39 | P | White/unlabeled: | P |
| 40 | G | White/unlabeled: | G |
| 41 | H, Y | Gray/aqua- | Any amino acid |
| 42 | K | Green: | Any amino acid |
| 43 | T | White/unlabeled: | T |
| 44 | R | Green: | Any amino acid |
| 45 | F | White/unlabeled: | F |
| 46 | E | Green: | Any amino acid |
| 47 | G | White/unlabeled: | G |
| 48 | R | Green: | Any amino acid |
| 49 | E | Green: | Any amino acid |
| 50 | T | Green: | Any amino acid |
| 51 | I | White/unlabeled: | I |
| 52 | W | Green: | Any amino acid |
| 53 | A | Green: | Any amino acid |
| 54 | H | White/unlabeled: | H |
| 55 | M | White/unlabeled: | M |
| 56 | R | Green: | Any amino acid |
| 57 | L | Green: | Any amino acid |
| 58 | F | White/unlabeled: | F, H |
| 59 | P | White/unlabeled: | P |
| 60 | E | Green: | Any amino acid |
| 61 | Y | Green: | Any amino acid |
| 62 | V, M | Gray/aqua- | Hydrophobic AAs |
| 63 | T | Green: | Any AA |
| 64 | V, I | Gray/aqua- | Any amino acid |
| 65 | R | Green: | Any amino acid |
| 66 | F | White/unlabeled: | F |
| 67 | T | Green: | Any amino acid |
| 68 | D | Green: | Any amino acid |
| 69 | V | White/unlabeled: | V |
| 70 | Q | Green: | Any amino acid |
| 71 | F | White/unlabeled: | F |
| 72 | Y | Dark green: | Y |
| 73 | E | Green: | Any amino acid |
| 74 | T | White/unlabeled: | T |
| 75 | A | Green: | Any amino acid |
| 76 | D | Green: | Any amino acid |
| 77 | P | White/unlabeled: | P |
| 78 | D | Green: | Any amino acid |
| 79 | L | Green: | Any amino acid |
| 80 | A | White/unlabeled: | A |
| 81 | I | Dark Green: | I |
| 82 | G | White/unlabeled: | G |
| 83 | E | Dark green: | E |
| 84 | F | White/unlabeled: | F, Y |
| 85 | H | Green: | Any amino acid |
| 86 | G | White/unlabeled: | G |
| 87 | D | Green: | Any amino acid |
| 88 | G | White/unlabeled: | G |
| 89 | V | Green: | Any amino acid |
| 90 | H, L | Gray/aqua- | Any amino acid |
| 91 | T | Green: | Any amino acid |
| 92 | V, A | Gray/aqua- | Any amino acid |
| 93 | S | Green: | Any amino acid |
| 94 | G | Green: | Any amino acid |
| 95 | G | Green: | Any amino acid |
| 96 | K | Green: | Any amino acid |
| 97 | L | White/unlabeled: | LY |
| 98 | A | Green: | Any amino acid |
| 99 | A, Y | Gray/aqua- | Any amino acid |

TABLE 6-continued

SEQ ID NO: 6

| Residue # | Alignment AA | Specificity | Alternative residues |
|---|---|---|---|
| 100 | D | Green: | Any amino acid |
| 101 | Y | Pink: | F or Y |
| 102 | I | Dark Green: | I |
| 103 | S, A | Gray/aqua- | Any amino acid |
| 104 | V | Dark green: | V |
| 105 | L, W | Gray/aqua- | Any amino acid |
| 106 | R | Green: | Any amino acid |
| 107 | T | White/unlabeled: | T |
| 108 | R | Green: | Any amino acid |
| 109 | D | Green: | Any amino acid |
| 110 | G | White/unlabeled: | G |
| 111 | Q | Green: | Any amino acid |
| 112 | I | White/unlabeled: | I |
| 113 | L | Green: | Any amino acid |
| 114 | L | Green: | Any amino acid |
| 115 | Y | Pink: | F or Y |
| 116 | R | Dark green: | R |
| 117 | V, L | Gray/aqua- | Any amino acid |
| 118 | F | Dark Green: | F |
| 119 | F | White/unlabeled: | FW |
| 120 | N | Dark green: | N |
| 121 | P | White/unlabeled: | P |
| 122 | L | Dark green: | L |
| 123 | R | Green: | Any amino acid |
| 124 | V | White/unlabeled: | V, I |
| 125 | L | White/unlabeled: | L |
| 126 | E | Green: | Any amino acid |
| 127 | A, P | Gray/aqua- | Any amino acid |
| 128 | L | Green: | Any amino acid |
| 129 | G | Green: | Any amino acid |

In another embodiment, the isolated polypeptides comprise or consist of the polypeptide of SEQ ID NO: 7, which differs from SEQ ID NO: 6 (Table 6) by being limited at the surface residues ("green") or at highly variable regions in the peptides tested ("gray/aqua") to the residues shown in Table 7.

TABLE 7

(SEQ ID NO: 7)

| Residue # | Alignment AA | Specificity | Alternative residues |
|---|---|---|---|
| 2 | N | Green: | N, D, S, T, C |
| 4 | K | Green: | Charged AAs |
| 5 | E | Green: | Charged AAs |
| 8 | V | Green: | Hydrophobic or aliphatic AAs or Charged AAs |
| 9 | H | Green: | Charged or polar neutral AAs |
| 10 | S, A | Gray/aqua- | Aliphatic or polar neutral AAs |
| 12 | R | Green: | Charged AAs |
| 15 | E | Green: | Charged AAs |
| 16 | N | Green: | Polar neutral AAs |
| 18 | D | Green: | Charged AAs |
| 20 | R | Green: | Charged AAs |
| 21 | G | Green | Polar neutral AAs |
| 23 | C, S | Gray/aqua- | Polar neutral AAs or A |
| 24 | D | Green: | Charged AAs |
| 27 | H | Green: | Polar neutral or Charged AAs |
| 29 | E | Green: | Charged AAs |
| 31 | V | Green: | Hydrophobic or aliphatic AAs or Charged AAs |
| 33 | E | Green: | Charged AAs |
| 37 | A, P | Gray/aqua- | Hydrophobic, polar neutral, or Charged AAs |
| 41 | H, Y | Gray/aqua- | Hydrophobic or basic AAs |
| 42 | K | Green: | Charged AAs |
| 44 | R | Green: | Charged AAs |
| 46 | E | Green: | Charged AAs |
| 48 | R | Green: | Charged AAs |

TABLE 7-continued

(SEQ ID NO: 7)

| Residue # | Alignment AA | Specificity | Alternative residues |
|---|---|---|---|
| 49 | E | Green: | Charged AAs |
| 50 | T | Green: | Polar neutral AAs |
| 52 | W | Green: | Aromatic AAs or Charged AAs |
| 53 | A | Green: | Aliphatic AAs or Charged AAs |
| 56 | R | Green: | Charged AAs |
| 57 | L | Green: | Aliphatic AAs or Charged AAs |
| 60 | E | Green: | Charged AAs |
| 61 | Y | Green: | Aromatic AAs |
| 62 | V, M | Gray/aqua- | Hydrophobic or Aliphatic AAs |
| 63 | T | Green: | Polar neutral |
| 64 | V, I | Gray/aqua- | Hydrophobic AAs |
| 65 | R | Green: | Charged AAs |
| 67 | T | Green: | Polar neutral AAs |
| 68 | D | Green: | Charged AAs |
| 70 | Q | Green: | Polar neutral AAs |
| 73 | E | Green: | Charged AAs |
| 75 | A | Green: | Aliphatic AAs |
| 76 | D | Green: | Charged AAs |
| 78 | D | Green: | Charged AAs |
| 79 | L | Green: | Aliphatic AAs |
| 85 | H | Green: | Polar neutral AAs |
| 87 | D | Green: | Charged AAs |
| 89 | V | Green: | Aliphatic AAs or Charged AAs |
| 90 | H, L | Gray/aqua- | H, L, A, C, F, I, Q, R, S, T, V, Y |
| 91 | T | Green: | Polar neutral AAs or Charged AAs |
| 92 | V, A | Gray/aqua- | V, A, D, F, F, G, I, K, L, M, P, Q, R, S, T, W |
| 93 | S | Green: | Polar neutral or basic AAs |
| 94 | G | Green: | G, A, S |
| 95 | G | Green: | Polar neutral, acidic, or aromatic AAs |
| 96 | K | Green: | Charged AAs |
| 98 | A | Green: | Aliphatic AAs |
| 99 | A, Y | Gray/aqua- | Hydrophobic or polar neutral Aas |
| 100 | D | Green: | Charged AAs |
| 103 | S, A | Gray/aqua- | S, A, C, D, L, N, R, T, V, W |
| 105 | L, W | Gray/aqua- | L, W, A, F, I, K, M, S, T, V |
| 106 | R | Green: | Charged AAs |
| 108 | R | Green: | Charged AAs |
| 109 | D | Green: | Charged AAs |
| 111 | Q | Green: | Polar neutral AAs |
| 113 | L | Green: | Aliphatic or Charged AAs |
| 114 | L | Green: | Aliphatic or Charged AAs |
| 117 | V, L | Gray/aqua- | V, L, A, D, G, M, N, S, Y |
| 123 | R | Green: | Charged AAs |
| 126 | E | Green: | Charged AAs |
| 127 | A, P | Gray/aqua- | Aliphatic or polar neutral AAs |
| 128 | L | Green: | L, E, G, H, I, K, P, Q, R, T, V, or A |
| 129 | G | Green: | G, A, S |

In another embodiment, the isolated polypeptides comprise or consist of the polypeptide of SEQ ID NO: 8, which differs from SEQ ID NO: 6 (Table 6) by being limited at the surface residues ("green") or at highly variable regions in the peptides tested ("gray/aqua") to the residues shown in Table 8. In one embodiment, no more than 4 of the residues of SEQ ID NO: 8 are cysteine. In various embodiments, no more than 1, 2, or 3 of the residues of SEQ ID NO: 8 are cysteine.

TABLE 8

(SEQ ID NO: 8)

| Residue # | Alignment AA | Specificity | Alternative residues |
|---|---|---|---|
| 2 | N | Green: | N |
| 4 | K | Green: | K or C |
| 5 | E | Green: | K or C |
| 8 | V | Green: | V or C |
| 9 | H | Green: | H or C |
| 10 | S, A | Gray/aqua- | S, or A |
| 12 | R | Green: | R or C |

TABLE 8-continued (SEQ ID NO: 8)

| | | | |
|---|---|---|---|
| 15 | E | Green: | E or C |
| 16 | N | Green: | N or C |
| 18 | D | Green: | D or C |
| 20 | R | Green: | R or C |
| 21 | G | Green | G or C |
| 23 | C, S | Gray/aqua- | C, S, T, A |
| 24 | D | Green: | D or C |
| 27 | H | Green: | H or C |
| 29 | E | Green: | E or C |
| 31 | V | Green: | V or C |
| 33 | E | Green: | E or C |
| 37 | A, P | Gray/aqua- | A, P, E, K, P, Q, R, T |
| 41 | H, Y | Gray/aqua- | H, Y, F, K, L, T, V, W |
| 42 | K | Green: | K or C |
| 44 | R | Green: | R or C |
| 46 | E | Green: | E or C |
| 48 | R | Green: | R or C |
| 49 | E | Green: | E or C |
| 50 | T | Green: | T or C |
| 52 | W | Green: | W or C |
| 53 | A | Green: | A or C |
| 56 | R | Green: | R or C |
| 57 | L | Green: | L or C |
| 60 | E | Green: | E or C |
| 61 | Y | Green: | Y, H, R, W |
| 62 | V, M | Gray/aqua- | V, M |
| 63 | T | Green: | T or C |
| 64 | V, I | Gray/aqua- | V, I, G, K, P, W |
| 65 | R | Green: | R or C |
| 67 | T | Green: | T or C |
| 68 | D | Green: | D or C |
| 70 | Q | Green: | Q or C |
| 73 | E | Green: | E or C |
| 75 | A | Green: | A or C |
| 76 | D | Green: | D or C |
| 78 | D | Green: | D or C |
| 79 | L | Green: | L or C |
| 85 | H | Green: | H or C |
| 87 | D | Green: | D or C |
| 89 | V | Green: | V or C |
| 90 | H, L | Gray/aqua- | H, L, A, C, F, I, Q, R, S, T, V, Y |
| 91 | T | Green: | T or C |
| 92 | V, A | Gray/aqua- | V, A, D, E, F, G, I, K, L, M, P, Q, R, S, T, W |
| 93 | S | Green: | S, H or C |
| 94 | G | Green: | G or C |
| 95 | G | Green: | L3: G, E, W, Y or C |
| 96 | K | Green: | K or C |
| 98 | A | Green: | A or C |
| 99 | A, Y | Gray/aqua- | A, Y, C, F, G, I, L, N, T, V |
| 100 | D | Green: | D or C |
| 103 | S, A | Gray/aqua- | S, A, C, D, L, N, R, T, V, W |
| 105 | L, W | Gray/aqua- | L, W, A, F, I, K, M, S, T, V |
| 106 | R | Green: | R or C |
| 108 | R | Green: | R or C |
| 109 | D | Green: | D or C |
| 111 | Q | Green: | Q or C |
| 113 | L | Green: | L or C |
| 114 | L | Green: | L or C |
| 117 | V, L | Gray/aqua- | V, L, A, D, G, M, N, S, Y |
| 123 | R | Green: | R or C |
| 126 | E | Green: | E or C |
| 127 | A, P | Gray/aqua- | A, P, H, I, L, S, V |
| 128 | L | Green: | L, E, G, H, I, K, P, Q, R, T, V, C, or A |
| 129 | G | Green: | G or C |

In another embodiment, the isolated polypeptides comprise or consist of the polypeptide of SEQ ID NO: 9, which differs from SEQ ID NO: 6 (Table 6) by being limited at the surface residues ("green") or at highly variable regions in the peptides tested ("gray/aqua") to the residues shown in Table 9. The residues shown in Table 9 are all present in polypeptides made/tested in the examples that follow.

TABLE 9

(SEQ ID NO: 9)

| | | | |
|---|---|---|---|
| 2 | N | Green: | N |
| 4 | K | Green: | K |
| 5 | E | Green: | K |
| 8 | V | Green: | V |
| 9 | H | Green: | H |
| 10 | S, A | Gray/aqua- | S |
| 12 | R | Green: | R |
| 15 | E | Green: | E |
| 16 | N | Green: | N |
| 18 | D | Green: | D |
| 20 | R | Green: | R |
| 21 | G | Green | G |
| 23 | C, S | Gray/aqua- | C or S |
| 24 | D | Green: | D |
| 27 | H | Green: | H |
| 29 | E | Green: | E |
| 31 | V | Green: | V |
| 33 | E | Green: | E |
| 37 | A, P | Gray/aqua- | A or P |
| 41 | H, Y | Gray/aqua- | H, Y, or W |
| 42 | K | Green; | K |
| 44 | R | Green: | R |
| 46 | E | Green: | E |
| 48 | R | Green: | R |
| 49 | E | Green: | E |
| 50 | T | Green: | T |
| 52 | W | Green: | W |
| 53 | A | Green: | A |
| 56 | R | Green: | R |
| 57 | L | Green: | L |
| 60 | E | Green: | E |
| 61 | Y | Green: | Y, H |
| 62 | V, M | Gray/aqua- | V, M |
| 63 | T | Green: | T |
| 64 | V, I | Gray/aqua- | V, I, W |
| 65 | R | Green: | R |
| 67 | T | Green: | T |
| 68 | D | Green: | D |
| 70 | Q | Green: | Q |
| 73 | E | Green: | E |
| 75 | A | Green: | A |
| 76 | D | Green; | D |
| 78 | D | Green: | D |
| 79 | L | Green: | L |
| 85 | H | Green: | H |
| 87 | D | Green: | D |
| 89 | V | Green: | V |
| 90 | H, L | Gray/aqua- | H, L, V |
| 91 | T | Green: | T or C |
| 92 | V, A | Gray/aqua- | V, A |
| 93 | S | Green: | S |
| 94 | G | Green: | G |
| 95 | G | Green: | G |
| 96 | K | Green: | K |
| 98 | A | Green: | A |
| 99 | A, Y | Gray/aqua- | A, Y |
| 100 | D | Green: | D |
| 103 | S, A | Gray/aqua- | S, A, T |
| 105 | L, W | Gray/aqua- | L, W |
| 106 | R | Green: | R |
| 108 | R | Green: | R |
| 109 | D | Green: | D |
| 111 | Q | Green: | Q |
| 113 | L | Green: | L |
| 114 | L | Green: | L |
| 117 | V, L | Gray/aqua- | V, L |
| 123 | R | Green: | R |
| 126 | E | Green: | E |
| 127 | A, P | Gray/aqua- | A, P |
| 128 | L | Green: | L or A |
| 129 | G | Green: | G |

In one further embodiment of any of the polypeptides of the invention, each of residues 34, 101, and 115 are Y. In this embodiment, the polypeptides of the invention show high specificity for DIG. In another embodiment of any of the polypeptides of the invention, 1, 2, or all 3 of residues 34, 101, and 115 are F. In these various embodiments, the steroid specificity of the polypeptides of the invention is shifted such that certain variants bind better to digoxigenin and others bind better to related steroids digitoxigenin, progesterone, and (β-estradiol, as described in more detail herein.

In another embodiment of any of the polypeptides of the invention, residue 84 is Y. In this embodiment, polypeptides of the invention are exemplified by Dig5.1 (SEQ ID: 11), which differs in its hydrogen bonding pattern compared to the DIG10 series in that the residue that contacts the lactone ring of DIG—in the DIG10 series this is Y115, but in DIG5.1 it is Y84. In a further embodiment of this embodiment, at least one of the following is true:

Residue 7 is L;
Residue 41 is W;
Residue 58 is H;
Residue 61 is H;
Residue 64 is W;
Residue 90 is V;
Residue 97 is Y:
Residue 103 is T;
Residue 115 is L;
Residue 119 is W;
Residue 124 is I; and/or
Residue 128 is A.

In various embodiments, 2, 3, 4, 5, 6, 7, 8, 9, 10, 11, or all 12 of the residues are as defined.

In various further embodiments, the isolated polypeptide of the invention comprises or consists of a polypeptide selected from the group consisting of: (Residues in parentheses are optional)

DIG5
(SEQ ID NO: 10)
MNAKEILVHSLRLLENGDARGWCDLFHPEGVLEFPYAPPGWKTRFEGRET

IWAHMRLHPEHVTVRFTDVQFYETADPDLAIGEYHGDGVVTVSGGKYAAD

FITVLRTRDGQILLYRVFWNPLRALEAAG(GVEAAAKIVQGA);

DIG5.1
(SEQ ID NO: 11)
MNAKEILVHSLRLLENGDARGWCDLFHPEGVLEYPYAPPGWKTRFEGRET

IWAHMRLHPEHVTWRFTDVQFYETADPDLAIGEYHGDGVVTVSGGKYAAD

YITVLRTRDGQILLLRVFWNPLRILEAAG(GVEAAAKIVQGA);

DIG10
(SEQ ID NO: 12)
MNAKEIVVHSLRLLENGDARGWCDLFHPEGVLEYPYAPPGHKTRFEGRET

IWAHMRLFPEYVTVRTFTDVQFYETADPDLAIGEFHGDGVHTVSGGKLAA

DYISVLRTRDGQILLYRVFFNPLRVLEALG(GVEAAAKIVQGA);

DIG10.1
(SEQ ID NO: 13)
MNAKEIVVHALRLLENGDARGWCDLFHPEGVLEYPYAPPGHKTRFEGRET

IWAHMRLFPEYMTIRETDVQFYETADPDLAIGEFHGDGVHTVSGGKLAAD

YISVLRTRDQILLYRLFFNPLRVLEPLG(GVEAAAKIVQGA);

DIG10.2
(SEQ ID NO: 14)
MNAKEIVVHALRLLENGDARGWCDLFHPEGVLEYPYPPPGYKTRFEGRET

IWAHMRLFPEYMTIRFTDVQFYETADPDLAIGEFHGDGVHTVSGGKLAAD

YISVLRTRDGQILLYRLFFNPLRVLEPLG(GVEAAAKAQGA);

DIG10.3
(SEQ ID NO: 15)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAYD

YIAVWRTRDGQILLYRLFFNPLRVLEPLG(GVEAAAKIVQGA);

DIG10.2,
(SEQ ID NO: 16)
MNAKEIVVHALRLLENGDARGWCDLFHPEGVLEYPYPPPGYKTRFEGRET

IWAHMRLFPEYMTIRFTDCQFYETADPDLAIGEFHGDGVHTVSGGKLAAD

YISVLRTRDGQILLYRLFFNPLRVLEPLG

DIG10.3,
(SEQ ID NO: 17)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAYD

YIAVWRTRDGQILLYRLFFNPLRVLEPLG

DIG10.3 Y99F
(SEQ ID NO: 18)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAFD

YIAVWRTRDGQILLYRLFFNPLRVLEPLG(GVEAAAKIVQGA);

DIG10.3 Y101F
(SEQ ID NO: 19)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAYD

FIAVWRTRDGQILLYRLFFNPLRVLEPLG(GVEAAAKIVQGA);

DIG10.3 Y115F
(SEQ ID NO: 20)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAYD

YIAVWRTRDGQILLFRLFFNPLRVLEPLG(GVEAAAKIVQGA);

DIG10.3 Y99F/Y101F
(SEQ ID NO: 21)
MNAKEIVVHALRLLENGDARGWSDLFHPEGVLEYPYPPPGYKTRFEGRET

IWAHMRLFPEYMTIRFTDVQFYETADPDLAIGEFHGDGVLTASGGKLAFD

FIAVWRTRDGQILLYRLFFNPLRVLEPLG(GVEAAAKIVQGA);

DIG10.3 Y34E/Y99F/Y101F
(SEQ ID NO: 22)
MNAKEIVVHALRLLENGDARGWSDLFHPEGVLEFPYPPPGYKTRFEGRET

IWAHMRLFPEYMTIRFTDVQFYETADPDLAIGEFHGDGVLTASGGKLAFD

FIAVWRTRDGQILLYRLFFNPLRVLEPLG(GVEAAAKIVQGA);

and

DIG10.3 Y34F/Y99F/Y101F/Y115F
(SEQ. ID NO: 23)
MNAKEIVVHALRLLENGDARGWSDLFHPEGVLEFPYPPPGYKTRFEGRET

IWAHMRLFPEYMTIRFTDVQFYETADPDLAIGEFHGDGVLTASGGKLAFD

FIAVWRTRDGQILLFRLFFNPLRVLEPLG(GVEAAAKIVQGA).

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, etc. Such linkage can be covalent or non-covalent as is understood by those of skill in the art.

In a further embodiment, the polypeptides of any embodiment of any aspect of the invention may further comprise a tag, such as a detectable moiety. The tag(s) can be linked to the polypeptide through covalent bonding, including, but not limited to, disulfide bonding, hydrogen bonding, electrostatic bonding, nucleophilc (i.e. Cys, Lys) conjugation chemistry, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used diagnostically to, for example, identify the presence of digoxin or other steroid in a sample of interest. However, they may also be used for other detection and/or analytical and/or diagnostic purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such as $^{33}P$, $^{32}P$, $^{35}S$, $^{3}H$, and $^{125}I$. Polypeptides of the invention can be attached to radionuclides directly or indirectly via a chelating agent by methods well known in the art.

When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also be attached to solid supports, which are particularly useful for in vitro assays or purification of digoxin or other steroids. Such solid supports might be porous or nonporous, planar or nonplanar and include, but are not limited to, glass, cellulose, polyacrylamide, nylon, polystyrene, polyvinyl chloride or polypropylene supports. The polypeptides can also, for example, usefully be conjugated to filtration media, such as NHS-activated Sepharose or CNBr-activated Sepharose for purposes of affinity chromatography. They can also usefully be attached to paramagnetic microspheres, typically by biotin-streptavidin interaction. As another example, the polypeptides of the invention can usefully be attached to the surface of a microtiter plate for ELISA.

In another aspect, the present invention provides pharmaceutical compositions, comprising one or more polypeptides of the invention and a pharmaceutically acceptable carrier. In this embodiment, the polypeptides of the invention may be used, for example, to treat digoxin overdoses. The pharmaceutical composition may comprise in addition to the polypeptide of the invention (a) a lyoprotectant; (b) a surfactant; (c) a bulking agent; (d) a tonicity adjusting agent; (e) a stabilizer: (f) a preservative and/or (gi a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant. e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a still further aspect, the present invention provides host cells that have been transfected with the recombinant expression vectors disclosed herein, wherein the host cells can be either prokaryotic (such as bacteria) or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (RI. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In another aspect, the invention provides methods for treating digoxin overdose and/or toxicity, comprising administering to a subject in need thereof an amount effective of one or more polypeptides or pharmaceutical compositions of the invention to treat the digoxin toxicity. Digitalis or its constituents, digoxin and digitoxin, are the primary cardiotonic steroids that are used to treat cardiac arrhythmias, cardiac insufficiency and congestive heart failure. Digoxin and digitoxin have narrow therapeutic ranges (1.0-1.9 nmol/L or approximately 0.8-1.5 ng/ml serum digoxin concentration) and overdose is not uncommon. Digoxin overdose and/or life-threatening digoxin toxicity are treated in the methods of the invention through the administration of one or more of the polypeptides of the invention that counteract the effects of digoxin or digitalis by binding to digoxin thereby preventing it from inhibiting or regulating the expression or function of $Na^+/K^+$ ATPase. In a preferred embodiment, each of residues 34, 101, and 115 of the polypeptide are Y. In this embodiment, the polypeptides of the invention show high specificity for DIG.

The subject may be any subject suffering from or at risk of suffering from digoxin overdose and/or toxicity, including but not limited to subjects being treated with digitalis or digoxin for cardiac arrhythmias, cardiac insufficiency and congestive heart failure. The subject may be a mammal, such as a human. As used herein, "treating" means to provide any clinical benefit in reducing digoxin toxicity or the effects of digoxin overdose.

As used herein, an "amount effective" refers to an amount of the polypeptide that is effective for treating the digoxin overdose and/or toxicity. The pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In another aspect, the invention provides methods for detecting digoxin, comprising contacting a sample of interest with a detectable polypeptide of the invention under suitable conditions for binding the detectable polypeptide to digoxin present in the sample to form a polypeptide-digoxin binding complex, and detecting the polypeptide-digoxin binding complex. In one embodiment, the sample is a biological sample, including but not limited to blood, serum, nasal secretions, tissue or other biological material from a subject to be tested. The polypeptides of the invention for use in this aspect may comprise a conjugate as disclosed above, to provide a tag useful for any detection technique suitable for a given assay. The tag used will depend on the specific detection/analysis/diagnosis techniques and/or methods used. The methods may be carried out in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape.

In one non-limiting embodiment, polypeptides with an Y residue at positions 34, 99, and 101 (including but not limited to Dig10.3 (SEQ ID NO:15) may be used in assays for detecting DIG and/or digoxin and/or distinguishing them from other steroids. In other non-limiting embodiments, (a) polypeptides with an F residue at position 101, a Y residue at position 34, and a F or Y at position 99 (including but not limited to DIG10.3 Y101F (SEQ ID NO:19)) may be used for detecting digitoxigenin and/or distinguishing it from other steroids (such as from DIG, digoxin, or progesterone); (b) polypeptides with an F residue at each of residues 34 and 101, and either Y or F at position 99 (including but not limited to DIG10.3 Y34F/Y99F/Y101F (SEQ ID NO:23)) may be used to detect digitoxigenin and/or progesterone, and/or to distinguish them from other steroids (such as from DIG or digoxin).

EXAMPLE 1

Figure 1A:
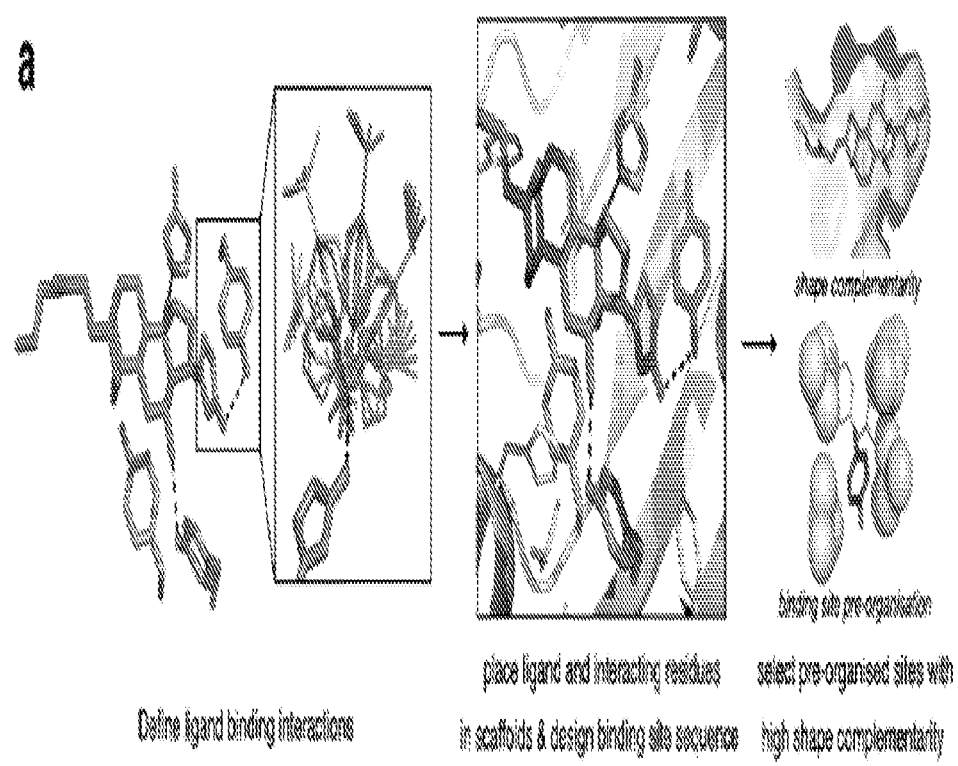
FIG. 1. Computational Design Methodology and Experimental Validation, a, Overview of the computational design procedure. First, the geometric positions of a set of pre-chosen interaction side chains are defined with respect to the ligand (left panel), and rotamers for each interaction side chain are enumerated (left panel, inset). Second, a set of scaffolds is searched for backbones that can accommodate all of the desired interactions. For cases in which all chosen interaction residues can be placed in the scaffold protein and orient the ligand in the native binding cavity with no backbone clashes, the binding site sequence is optimized for binding affinity (center panel). Designs having native-like properties, such as high shape complementarity and binding site pre-organization, are chosen for experimental characterization (right panel). b, Ranking of the 17 experimentally characterized DIG designs by ligand interaction energy (Rosetta energy units, Reu) and the average (geometric mean) Boltzmann weight of the conformations of the side chains that hydrogen bond to the ligand. DIG10, depicted in red, scores the best by both metrics. c, Flow cytometric analysis of yeast cells expressing computationally designed proteins as part of a surface-targeted fusion protein with a C-terminal c-Myc tag. Yeast surface expression and DIG binding were confirmed by labeling the cells with a fluorescein (FITC)-conjugated anti-c-Myc antibody and a pre-incubated mixture of 2.7 μM biotinylated DIG-functionalized BSA (~10 DIG/BSA) and phycoerythrin (PE)-conjugated streptavidin, respectively. Cell populations shown are a negative control for binding (ZZ(−)), an anti-DIG antibody serving as a positive control for binding (ZZ(+)), DIG10, DIG10 in the presence of excess (730 μM) unlabeled DIG competitor, and scaffold 1z1s. DIG10 labeled with 2.7 μM biotinylated DIG-functionalized RNase (~6 DIG/RNase) is also shown. d, On-yeast substitutions of DIG10 designed hydrogen-bonding residues Tyr34, Tyr101, and Tyr115 to Phe and binding cavity residue Val117 to Arg reduces expressing-population compensated mean binding (PE) signals to background nonbinding (ZZ(−)) levels.

We developed a computational method for designing ligand binding proteins with three properties characteristic of naturally occurring binding sites: (1) specific energetically favorable hydrogen bonding and van der Waals interactions with the ligand, (2) high overall shape complementarity to the ligand, and (3) structural pre-organization in the unbound protein state, which minimizes entropy loss upon ligand binding[15,16]. To program in specific interactions with the small molecule, disembodied binding sites are created by positioning amino acid side chains around the ligand in orientations optimal for hydrogen bonding and other energetically favorable interactions and then placed at geometrically compatible binding sites in a set of scaffold protein structures. The surrounding side chain identities and conformations are then optimized to generate additional protein-ligand interactions and buttressing protein-protein interactions (FIG. 1a). Designs with protein-small molecule shape complementarity below those typical of native protein complexes[17] or having interface side chain conformations with low Boltzmann-weighted probabilities in the unbound state[16] are then discarded.

Figure 1B:
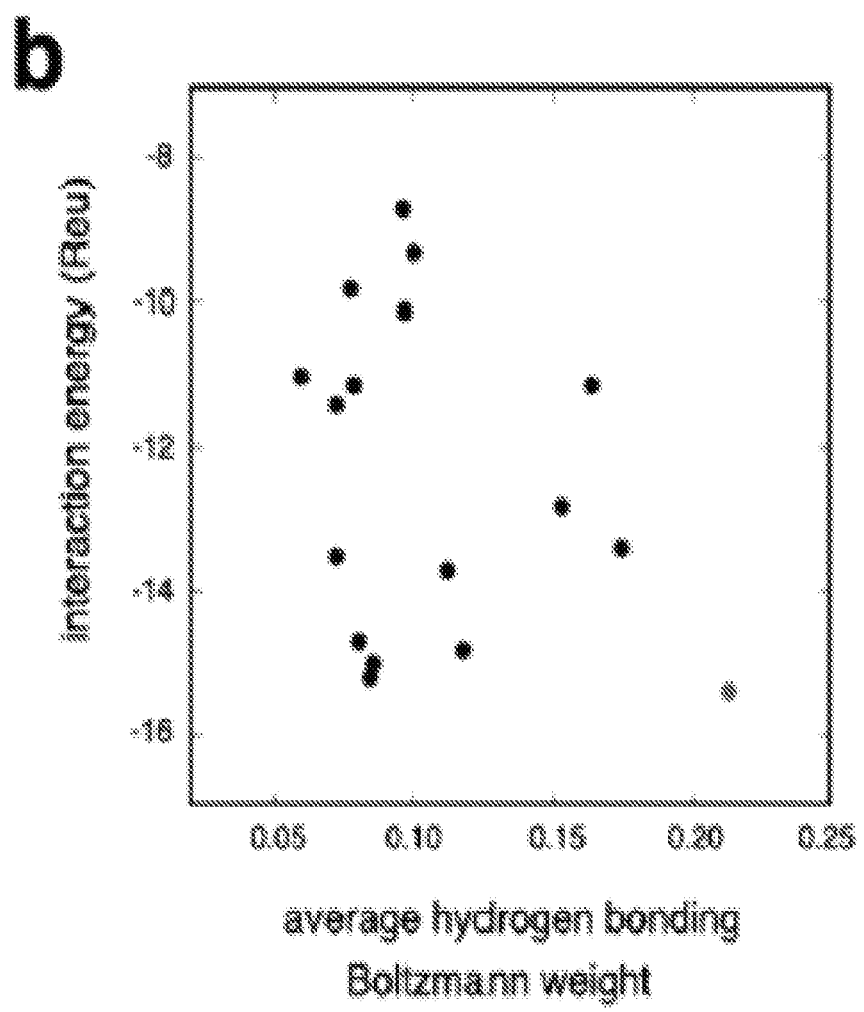

We used the method to design proteins that bind the steroid digoxigenin (DIG), the aglycone of digoxin, a cardiac glycoside used to treat heart disease[18], and a commonly used non-radioactive biomolecular labeling reagent[19]. Anti-DIG antibodies are routinely administered to treat overdoses of digoxin, which has a narrow therapeutic window[20], and are used widely to detect biomolecules in applications such as fluorescence in situ hybridization[19]. We created idealized DIG binding sites with hydrogen bonds from Tyr or His to the lactone carbonyl oxygen and both hydroxyl groups of DIG and hydrophobic packing interactions between Tyr, Phe, or Trp and the steroid ring system (FIG. 1a). These interactions were embedded in designed binding sites with high shape complementarity to DIG as outlined above, and 17 designs were selected for experimental characterization based on computed binding affinity, shape complementarity, and the extent of binding site pre-organization in the unbound state (FIG. 1b).

Figure 1C:
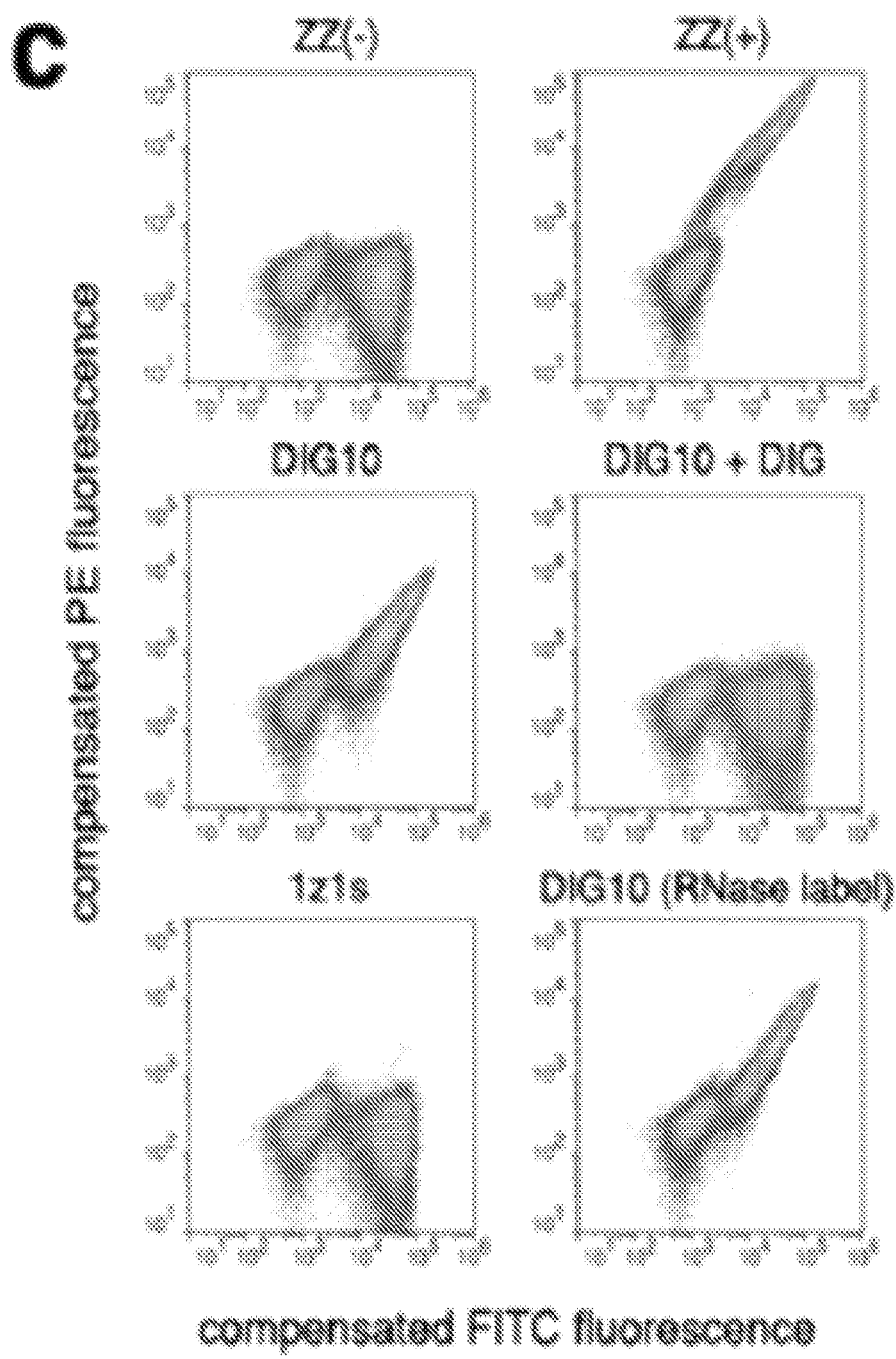
Figure 1D:
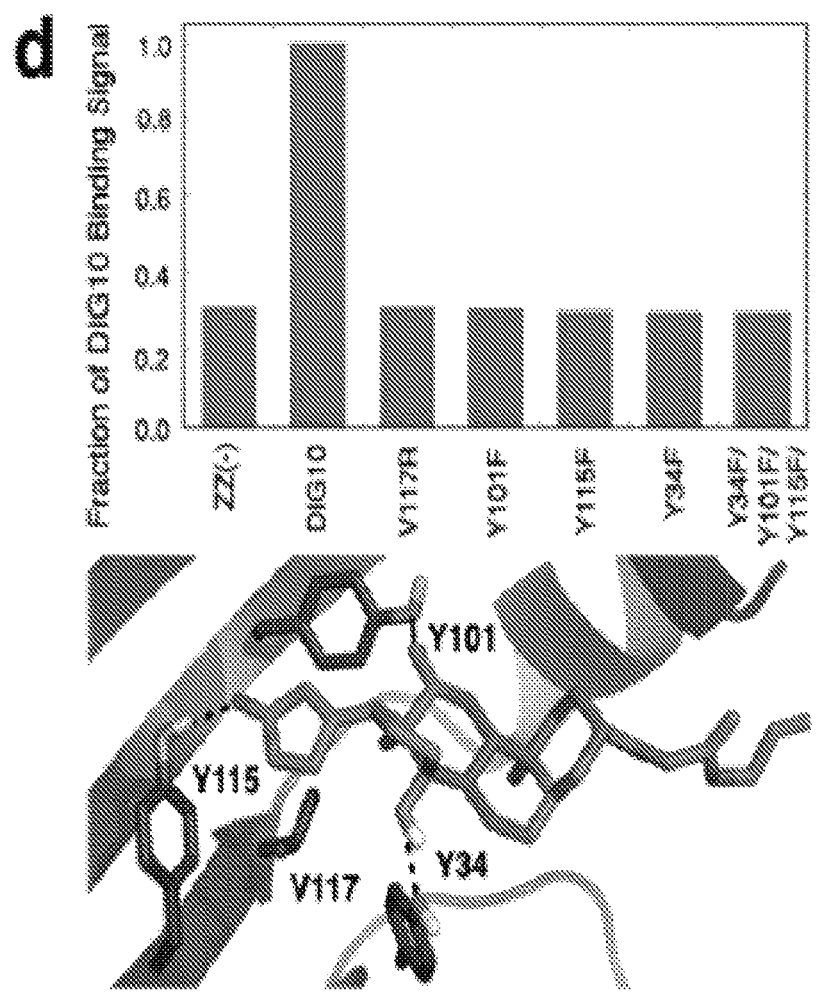
Figures 2A, 2B:
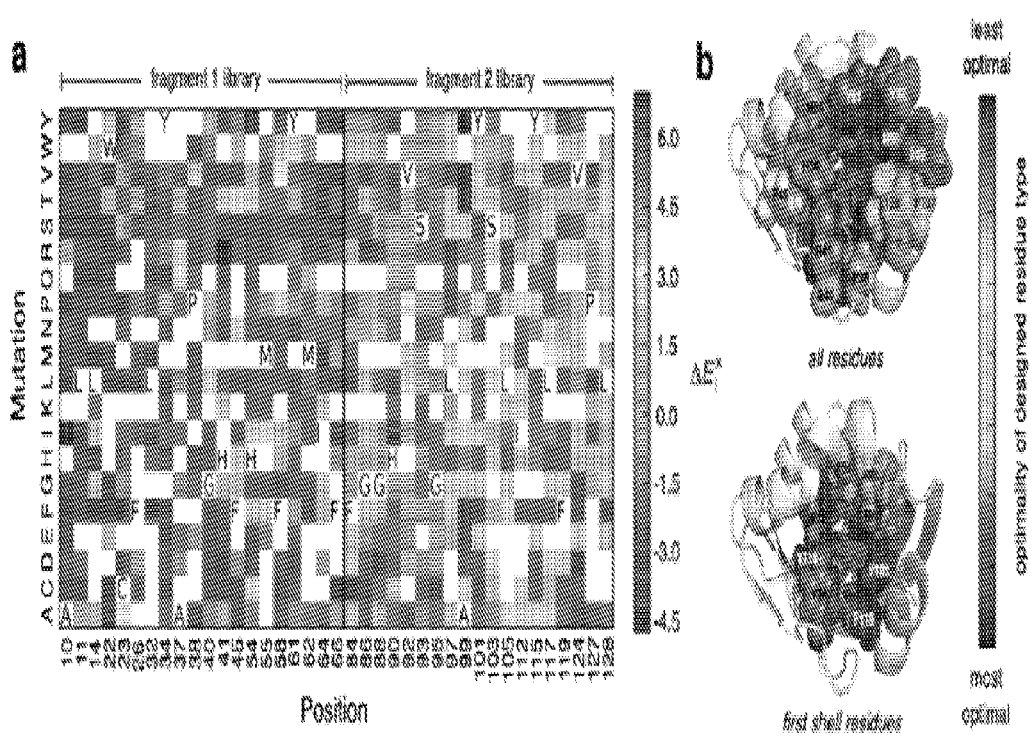
FIG. 2. Affinity Maturation. a, Binding fitness landscape of DIG10.1a probed by deep sequencing. The effect of each amino acid substitution at 39 binding site residues on binding ($\Delta E_i^x$) was assessed by determining the log$_2$ ratios of the frequencies of substitutions to each amino acid at each position after selection for DIG binding to the frequencies of the substitutions in the unselected population. Colored grids represent single point mutations having ≥20 counts in the unselected N-terminal (fragment 1) and C-terminal (fragment 2) libraries. White grids show mutations for which there were not enough sequences in the unselected library to make a definitive conclusion about function. The initial DIG10.1a amino acid at each position is indicated in bold using its one-letter amino acid code. b, The optimality of each DIG10.1a input residue type mapped onto the computational model of DIG10.1a. Optimality is defined as the positional Z-score.
Figure 2C:
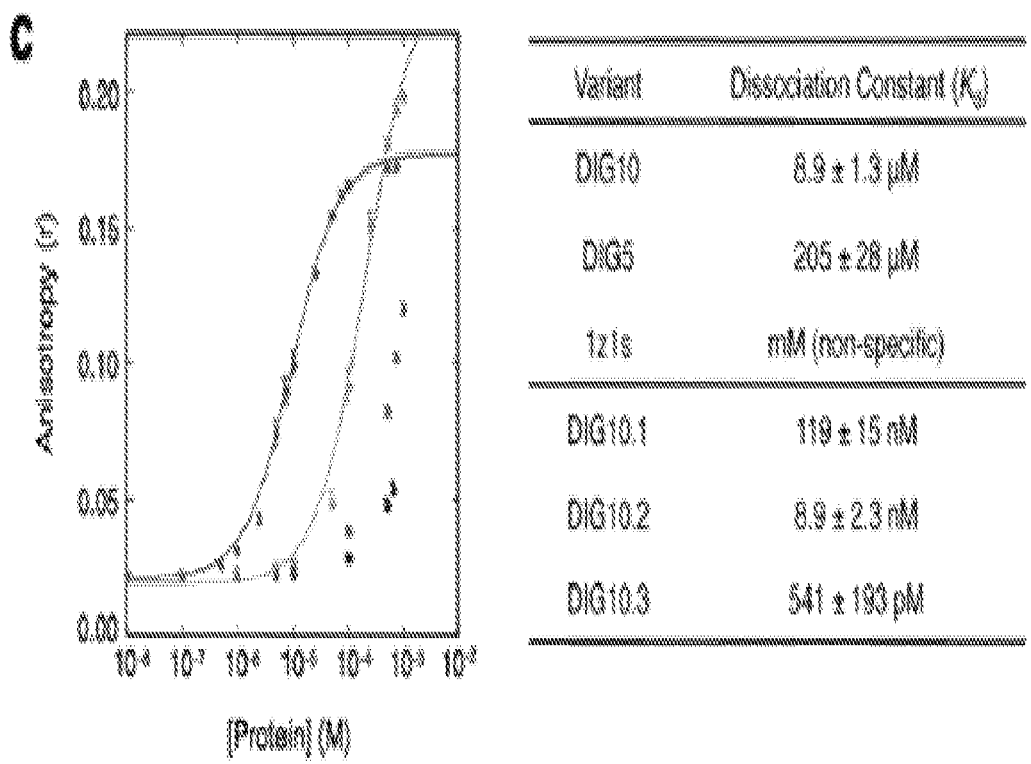
Figure 2D:
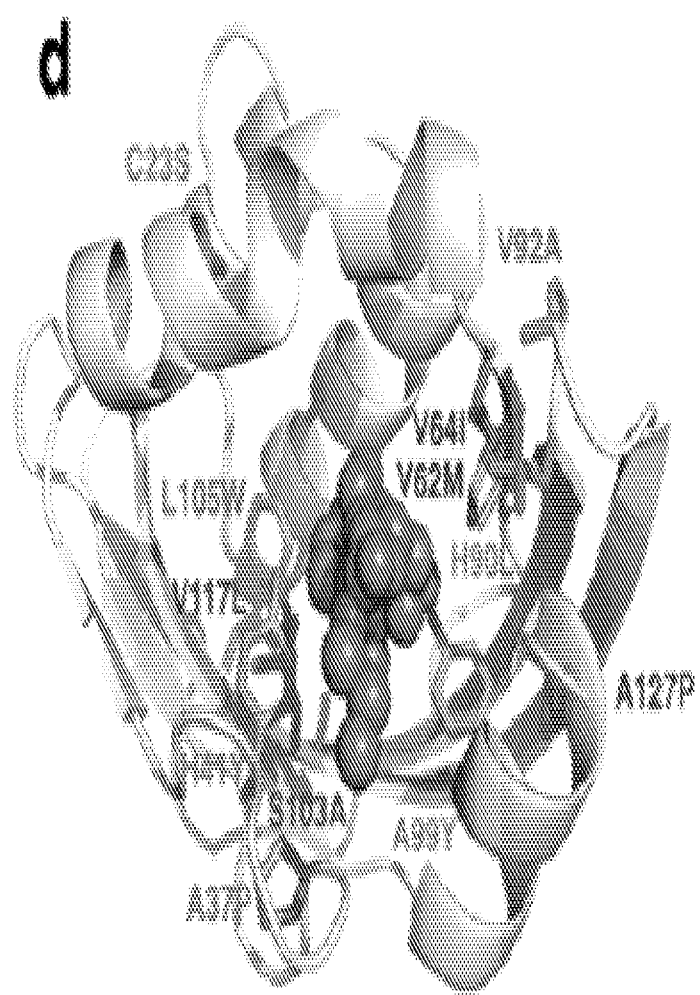

Binding of the designed proteins to DIG was probed by yeast surface display[21] and flow cytometry using biotinylated DIG-functionalized bovine serum albumin (DIG-BSA) or ribonuclease (DIG-RNase). DIG5 and DIG10 bound to both labels (FIGS. 1c and 5), and binding was reduced to background levels when ~1 mM of unlabeled DIG was added as a competitor (FIGS. 1c and 6). Fluorescence polarization (FP) measurements with purified proteins and Alexa488 fluorophore-conjugated DIG (DIG-PEG$_3$-Alexa488) indicated affinities in the low to mid micromolar range, with DIG10 binding more tightly (FIG. 2c). The scaffold from which both DIG5 and DIG10 derive. PDB ID 1zls, a protein of unknown function from *Pseudomonas aeruginosa*, does not bind to either label (FIG. 1c and FIG. 6a) when expressed on the yeast surface or to DIG-PEG$_3$-Alexa488 in solution (FIG. 2c), suggesting that the binding activities of both proteins are mediated by the computationally designed interfaces. Indeed, substitution of small non-polar residues in the central binding pockets of DIG5 and DIG10 with arginines resulted in complete loss of binding, and mutation of the designed hydrogen-bonding tyrosine and histidine residues to the nearly isosteric phenylalanine reduced binding; for DIG10, substitution of any of the three interacting tyrosines abolished binding completely (FIG. 1d and FIG. 7). Optimization of DIG10 by a single round of mutagenesis and selections using yeast surface display and fluorescence-activated cell sorting (FACS) identified small-to-large hydrophobic amino acid changes that increase binding affinity 75-fold to yield DIG10.1a, likely by optimizing steric packing against the ligand (FIG. 2c,d and FIGS. 8-9).

To provide feedback for improving the overall design methodology and to evaluate the contribution of each residue in the DIG10.1a binding site, we used next generation sequencing to generate a comprehensive binding fitness map[22-24]. A library of variants with ~1-3 substitutions at 39 designed interface positions in Dig10.1a was generated using doped oligonucleotide mutagenesis, displayed on yeast, and subjected to selections using a monovalent DIG-PEG$_3$-biotin conjugate (FIG. 10). Variants with increased affinity for DIG were isolated by FACS, and next generation sequencing was used to quantify the frequency of each single point mutation in the unselected and selected populations. A large majority of the interrogated variants were depleted in the selected population relative to the unselected input library, suggesting that most of the designed residues are close to optimal for binding (FIG. 2a and FIG. 11). In particular, mutation of the three designed hydrogen bonding residues, Tyr34, Tyr01, and Tyr115, to any other amino acid was disfavored. Several large hydrophobic residues that pack against the ligand in the computational model are also optimal for binding (e.g. Phe66 and Phe119). Besides A99, which directly contacts DIG, most of the observed mutations that improve binding are located in the second coordination shell of the ligand and fall into two functional categories: (1) core substitutions tolerating mutation to chemically-similar amino acids (e.g. Leu105 and Cys23), and (2) solvent-exposed loop amino acids having high sequence entropy (e.g. His90, Val92). The single best clone in the libraries, DIG10.2, features two of the most highly enriched mutations, Ala37Pro and His41Tyr (FIG. 2c,d and FIGS. 9 and 12).

Combination of the most highly enriched substitutions in a library followed by selections led to DIG10.3 (FIG. 13), which binds both DIG and its cardiac glycoside derivative digoxin with picomolar affinity (FIG. 2c,d, FIG. 14), rivaling the affinities of anti-digoxin antibody therapeutics[20] and an evolved single-chain variable anti-DIG antibody fragment[7]. FP-based affinity measurements of DIG10.3 and its Tyr knockouts suggest that the designed hydrogen bonds each contribute ~2 kcal/mol to binding energy (FIG. 9). Although many residues in DIG10.3 and its less-evolved variants contribute to binding, Y34, Y101, and Y115 make direct and important interactions.

The crystal structures of DIG10.2 and DIG10.3 in complex with DIG were solved to 2.05 Å and 3.2 Å resolution, respectively (FIG. 3a,b and FIGS. 15-17). The structure of DIG10.2 bound to DIG shows atomic-level agreement (average all atom root mean squared deviation (RMSD) of 0.54 Å) with the design model (FIG. 3c). The ligand-protein interface has high shape complementarity ($S_c$=0.66) and there are no observable water molecules within the binding pocket. The DIG binding mode is nearly identical in the structure and the model, with an average RMSD of 0.99 Å for all 28 ligand heavy atoms (FIG. 3d). As anticipated, Tyr34, Tyr101, and Tyr115 make the designed hydrogen bonds with O3, O2, and O1 of DIG, respectively. Tyr41, a residue identified during affinity maturation, engages in an additional long hydrogen bond with the terminal hydroxyl group of DIG (O5) (FIG. 17). Of 27 non-glycine and non-alanine non-surface protein residues within ~10 Å of the ligand, 21 adopt rotamer conformations in the design model (FIG. 18), including Tyr101 and Tyr115 (in chain B) as well as the first-shell packing residues Trp22, Phe58, and Phe119. The structure of DIG10.3 bound to DIG also agrees with the design model (average all-atom RMSD of 0.68 Å) (FIG. 19).

Figure 4A:
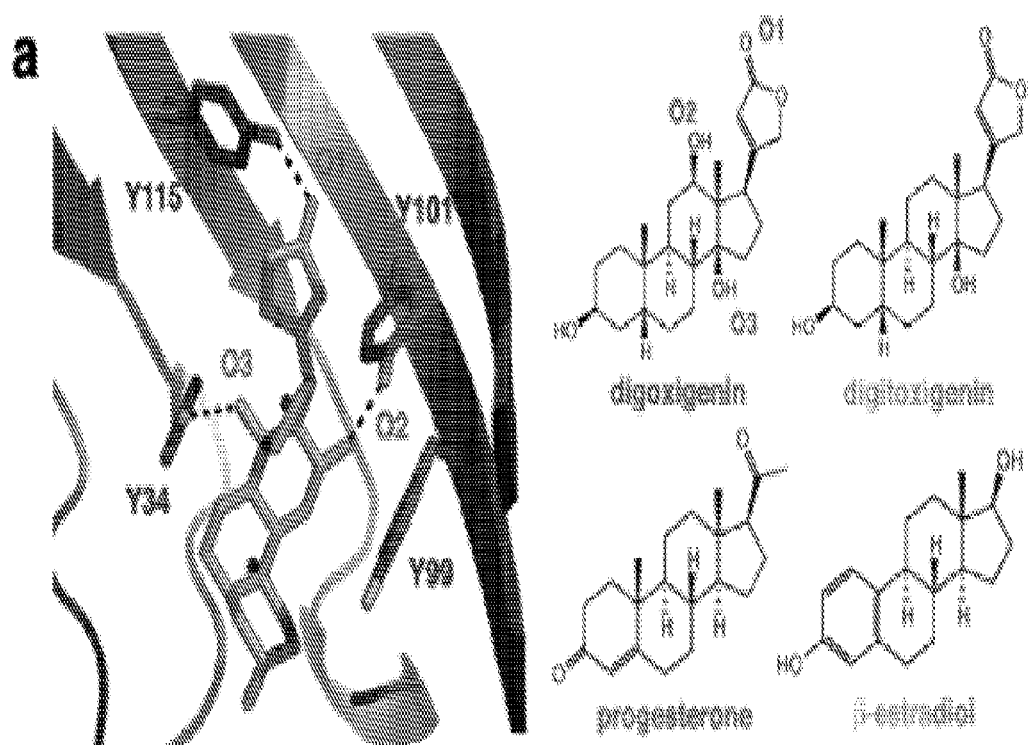
Figures 4B, 4C:
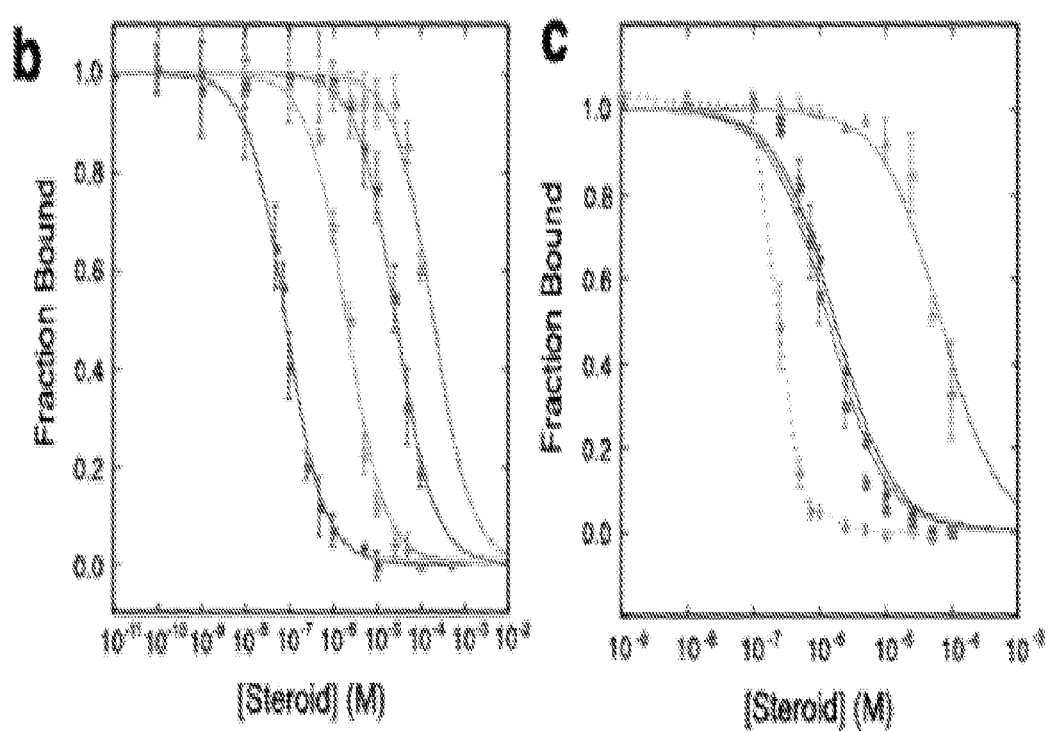
Figures 4D, 4E:
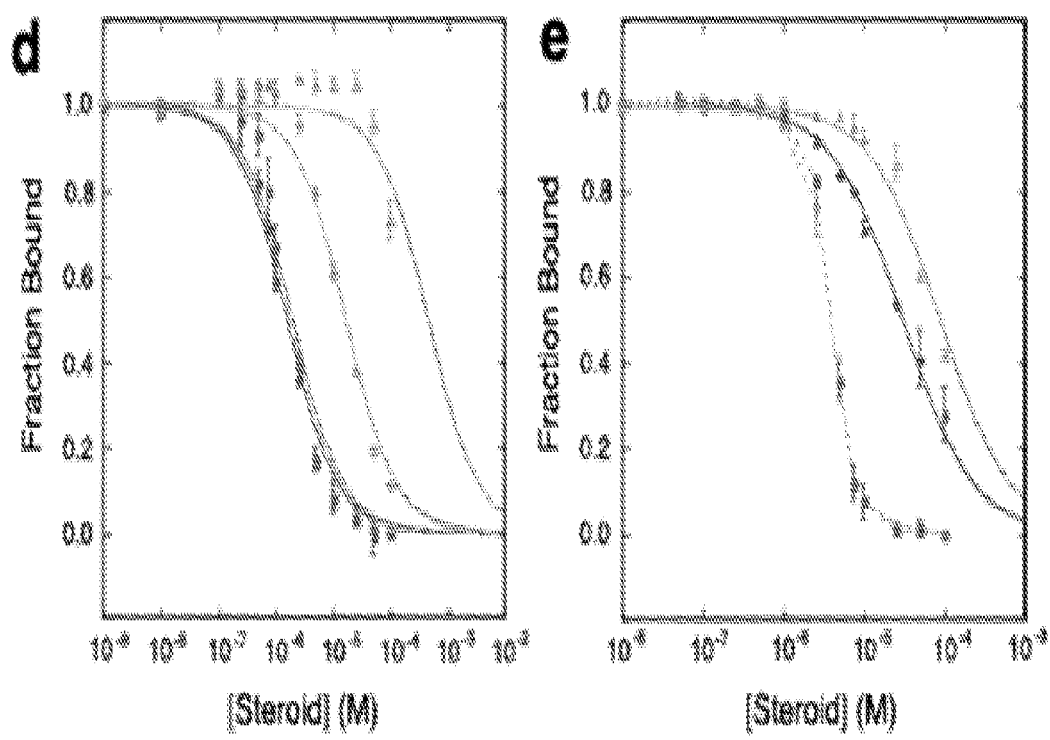

We assessed the binding specificity of DIG10.3 by determining binding affinities for a series of related steroids by equilibrium competition fluorescence polarization assays. Experiments with DIG, digitoxigenin, progesterone, and β-estradiol showed a decrease in affinity corresponding to the loss of one, two, and three hydrogen bonds respectively (assuming ~1.8 kcal/mol per hydrogen bond[25]), as expected from the structure if these compounds bind in the same orientation as DIG (FIG. 4a,b and Table 10). We next investigated whether the observed steroid selectivity could be reprogrammed by mutagenesis of the key hydrogen-bonding tyrosine residues. The variants Tyr101Phe, Tyr34Phe, and Tyr34Phe/Tyr99Phe/Tyr11Phe show clear preferences for more hydrophobic steroids in a predictable manner that depends on the hydrogen bonding capabilities of both the protein and the steroid. Mutation of Tyr101 to Phe eliminates the DIG-specific hydrogen bond with O2 of DIG and provides better hydrophobic packing for the other three steroids lacking a hydroxyl group at that position (FIG. 4c). Substitution of Tyr34 with Phe removes a hydrogen bond to the C14 hydroxyl groups of both DIG (O3) and digitoxigenin, enhancing the preference for progesterone and maintaining the relative binding order of DIG and digitoxigenin due to the intact DIG-specific Tyr101-DIG02 bond (FIG. 4d). Mutation of Tyr101, Tyr34, and binding site residue Tyr99 to Phe results in decreased binding affinity for DIG and increased affinity for the more hydrophobic steroids (FIG. 4e). These results confirm that the selectivity of DIG10.3 for DIG is conferred largely through the designed hydrogen-bonding interactions and demonstrate how selectivity can be programmed through positive design alone by control of designed protein-ligand hydrogen bonding and non-polar interactions.

TABLE 10

Specificity-swapped DIG10.3 Variants:

| Variant | Steroid | Inhibition Constant ($K_i$) |
| --- | --- | --- |
| DIG10.3 | Digoxigenin (DIG) | 653 ± 262 pM |
|  | digitoxigenin | 19 ± 7 nM |
|  | progesterone | 243 ± 91 nM |
|  | β-estradiol | 2.1 ± 0.8 μM |
|  | digoxin | 223 ± 105 pM |
| DIG10.3 Y101F | Digoxigenin (DIG) | 39 ± 8 nM |
|  | digitoxigenin | <3.8 nM |
|  | progesterone | 30 ± 9 nM |
|  | β-estradiol | 1.7 ± 0.4 μM |
| DIG10.3 Y34F | Digoxigenin (DIG) | 59 ± 6 nM |
|  | digitoxigenin | 714 ± 79 nM |
|  | progesterone | 76 ± 14 nM |
|  | β-estradiol | 15 ± 2 μM |
| DIG10.3 Y34F/Y99F/Y101F | Digoxigenin (DIG) | 580 ± 229 nM |
|  | digitoxigenin | <16 nM |
|  | progesterone | <17 nM |
|  | β-estradiol | 1.6 ± 0.6 μM |

Comparison of the properties of successful and unsuccessful designs provides a test of the hypotheses underlying the design methodology. While all 17 designed proteins by construction had high computed shape complementarity to DIG, the DIG10 design, which had the highest affinity for DIG, had the most favorable computed ligand interaction energy and was predicted to have the most pre-organized binding site (FIG. 1b), suggesting that these attributes should continue to be the focus of future design methodology development. One potential avenue for obtaining more favorable interaction energy would be the incorporation of additional binding site backbone flexibility to achieve more tightly packed binding sites: the observation that substitution of small hydrophobic interface residues to larger residues increased binding affinity indicates that the original DIG10 design was under-packed.

The binding fitness landscape in combination with the x-ray co-crystal structures highlight the importance of second shell interactions in stabilizing binding competent conformations. The fitness landscape favors substitution of Leu105, adjacent to the key hydrogen-bonding residue Tyr115, to Trp or other large hydrophobic residues (FIG. 2a). Both Tyr115 and Leu105 exhibit obvious conformational side chain heterogeneity in the four independent protein subunits of the 2.0 Å resolution DIG10.2 crystal structure. Mutation of Leu to Trp results in a more uniform set of side chain conformations at both amino acid positions in the lower resolution DIG10.3 design (which contains nine independently visualized subunits), as well as a more canonical hydrogen bond geometry between Tyr115 and DIG (FIG. 3e and FIG. 20). The higher affinity of DIG10.3 might result from a higher population of the pre-organized, higher affinity conformation of the protein[15,26]. Indeed, all key hydrogen-bonding tyrosines, particularly Tyr115, have higher computed Boltzmann weighted side chain probabilities in apo-DIG10.3 than in apo-DIG10.2 and apo-DIG10. Similarly, reduced backbone conformational entropy is likely responsible for the increased fitness of substitutions increasing β-sheet propensity at positions 90 and 92 which likely stabilize a more ordered extended strand backbone conformation (FIG. 2a). That conformational flexibility is selected against during affinity maturation suggests that accounting for free energy gaps between binding-competent and alternative states of the binding site[27], possibly by better assessing side chain entropy or explicitly designing second shell buttressing interactions for key contacts, should aid in achieving high affinity in the next generation of computationally designed ligand binding proteins.

The DIG binding affinity of DIG0.3 is within a factor of two of that of the widely used anti-DIG antibodies[20], and as it is very stable and can be expressed at high levels in bacteria it could provide more cost-effective alternative. With continued improvement in the methodology from feedback from experimental results, computational protein design should provide an increasingly powerful approach to creating a new generation of small molecule receptors for synthetic biology, therapeutic scavengers for toxic compounds, and robust binding domains for diagnostic devices.

Methods Summary

Design calculations were performed using Rosetta-Match[28] to incorporate five pre-selected interactions to DIG into a set of 401 scaffolds. RosettaDesign[29] was then used to optimize each binding site sequence for maximal ligand binding affinity. Designs having high interface energy, shape complementarity, and binding site pre-organization were selected for experimental characterization.

Designs were displayed on the surface of yeast strain EBY100 and examined for binding to a mixture of 2.7 μM biotinylated DIG-conjugated BSA or DIG-conjugated RNase and streptavidin-phycoerythrin on an Accuri C6 flow cytometer. Binding clones from yeast-surface displayed libraries based on DIG10 were selected using highly avid DIG-BSA or DIG-RNase or monovalent DIG-conjugated biotin on a Cytopeia inFlux cell sorter. DIG10.1a-derived library DNA was sequenced in paired-end mode on an Illumina MiSeq.

Proteins were expressed in *E. coli* Rosetta 2 (DE3) cells with a C-terminal TEV protease cleavable $His_6$ tag for biochemical assays. For crystallographic analysis of DIG10 variants, a 12-amino acid structurally disordered C-terminus deriving from the scaffold protein 1z1s was replaced directly with a $His_6$ tag. Binding affinities were determined by equilibrium fluorescence polarization[30] on a SpectraMax M5e microplate reader by monitoring the anisotropy of DIG-conjugated Alexa488 as a function of protein concentration. Equilibrium fluorescence polarization competition assays were performed by examining the effect of increasing concentrations of unlabeled DIG, digitoxigenin, progesterone, and β-estradiol on the anisotropy of designed protein-DIG-conjugated Alexa488 complex.

Methods

Computational methods. Full details for all computational methods are given in Supplementary Methods. Example command lines and RosettaScripts[31] design protocols are provided in Supplementary Data. Source code is freely available to academic users through the Rosetta Commons agreement. Design models, the scaffold library, and scripts for running design calculation are provided on the Baker lab website.

Matching. A set of 401 scaffolds was searched for backbones that can accommodate five pre-defined side chain interactions with DIG using RosettaMatch[2]. This set contained scaffolds previously used for design projects within our lab[33-35] as well as structural homologs of a subset of these scaffolds that are known to tolerate mutations. Rosetta sequence design. Two successive rounds of sequence design were employed. The purpose of the first was to maximize binding affinity for the ligand[36]. The goal of the second was to minimize protein destabilization due to aggressive scaffold mutagenesis while maintaining the binding interface designed during the first round. During the latter round, ligand-protein interactions were up-weighted by a factor of 1.5 relative to intra-protein interactions to ensure that binding energy was preserved. Two different criteria were used to minimize protein destabilization: (1) native scaffold residues identities were favored by 1.5 Rosetta energy units (Reu), and (2) no more than five residues were allowed to change from residue types observed in a multiple sequence alignment (MSA) of the scaffold if (a) these residues were present in the MSA with a frequency greater than 0.6 and, (b) if the calculated $\Delta\Delta G$ for mutation of the scaffold residue to alanine[37] was greater than 1.5 Reu in the context of the scaffold sequence. In some design calculations, identities of the matched hydrogen bonding residues were allowed to vary subject to the MSA and $\Delta\Delta G$ criteria described above. Designs having fewer than three hydrogen bonds between the protein and the ligand were rejected.

Design evaluation. Designs were evaluated on interface energy, shape complementarity, and apo-protein binding site pre-organization. The latter was enforced by two metrics: (1) explicitly introducing second-shell amino acids that hold the pre-selected residues in place using Foldit[38], and (2) eliminating designs having rotamer Boltzmann probabilities[39] <0.1 for more than one of the hydrogen bonding residues (Supplementary Table 5). All designs were evaluated for local sequence secondary structure compatibility, and those predicted to have backbone conformations that varied by >0.8 Å from their native scaffold were rejected (see Supplementary Methods).

General experimental methods. Detailed procedures for the syntheses of DIG-BSA-biotin, DIG-RNase-biotin, DIG-$PEG_3$-biotin, and DIG-$PEG_3$-Alexa488, as well as protein expression, purification, and crystallization, cloning, and mutagenesis methods are given in Supplementary Methods. Details about fluorescence polarization binding assays, gel filtration analysis, and protein stability measurements are also provided in Supplementary Methods. Yeast surface display. Designed proteins were tested for binding using yeast-surface display[40]. Yeast surface protein expression was monitored by binding of anti-cmyc FITC to the C-terminal myc epitope tag of the displayed protein. DIG binding was assessed by quantifying the phycoerythrin (PE) fluorescence of the displaying yeast population following incubation with DIG-BSA-biotin, DIG-RNase-biotin, or DIG-$PEG_3$-biotin, and streptavidin-phycoerythrin (SAPE). In a typical experiment using DIG-BSA-biotin or DIG-RNase-biotin, cells were resuspended in a premixed solution of PBSF (PBS+1 g/L of BSA) containing a 1:100 dilution of anti-cmyc FITC, 2.66 M DIG-BSA-biotin or DIG-RNase biotin, and 664 nM SAPE for 2-4 hr incubation at 4° C. Cellular fluorescence was monitored on an Accuri C6 flow cytometer using a 488 nm laser for excitation and a 575 nm band pass filter for emission. Phycoerythrin fluorescence was compensated to minimize bleed-over contributions from the FITC channel. Competition assays with free digoxigenin were performed as above except that between 750 μM and 1.5 mM of digoxigenin was added to each labeling reaction mixture. Full details are given in Supplementary Methods.

Affinity maturation. Detailed procedures for constructing and selecting all libraries, including those for deep sequencing, are provided in Supplementary Methods. Yeast surface display library selections were conducted on a Cytopeia inFlux cell sorter using increasingly stringent fluorescence gates. In all labeling reactions for selections, care was taken to maintain at least a 10-fold molar excess of label to cell surface protein. Cell surface protein molarity was estimated by assuming that an $O.D._{600}$ of 1.0=1e7 cells/mL and each cell displays 50,000 copies of protein[40]. For each round of sorting, we sorted at least 10 times the theoretical library size. FlowJo software v. 7.6 was used to analyze all data.

Next-generation sequencing. Two sequencing libraries based on DIG10.1a were assembled by recursive PCR: an N-terminal library (fragment 1 library) and a C-terminal library (fragment 2 library). To introduce mutations, we used degenerate PAGE-purified oligos in which 39 selected positions within the binding site were doped with a small amount of each non-native base at a level expected to yield 1-2 mutations per gene (TriLink BioTechnologies). Yeast cells were transformed with DNA insert and restriction-digested pETCON[41]. Surface protein expression was induced[40] and cells were labeled with anti-cymc-FITC and sorted for protein expression. Expressing cells were recovered, induced, labeled with 100 nM of DIG-$PEG_3$-biotin for >3 hrs at 4° C. and then SAPE and anti-cymc-FITC for 8 min at 4° C., and then sorted. For each library, clones having binding signals higher than that of DIG10.1a were collected (FIG. 10). To reduce noise from the first round of cell sorting, the sorted libraries were recovered, induced, and subjected to a second round of sorting using the same conditions (Supplementary Methods).

Library DNA was prepared as described[42]. Illumina adapter sequences and unique library barcodes were appended to each library pool by PCR amplification using population-specific primers. DNA was sequenced in paired-end mode on an Illumina MiSeq using a 300-cycle reagent kit and custom primers (see Supplementary Methods). Of a total 5,630,105 paired-end reads, 2,531,653 reads were mapped to library barcodes. For each library, paired end reads were fused and filtered for quality (Phred≥30). The resulting full-length reads were aligned against DIG10.1a using Enrich[43]. For single mutations having ≥7 counts in the original input library, a relative enrichment ratio between the input library and each selected library was calculated[42,44,45]. The effect of each amino acid substitution at 39 binding site residues on binding ($\Delta E_i^x$) is given as the log base 2 frequency of observing mutation x at position i in the selected versus the unselected population, relative to that of the DIG10.1a residue (orig) at position i:

$$\Delta E_i^x = \log_2\left(\frac{f_i^{x,sel}}{f_i^{x,unsel}}\right) - \log_2\left(\frac{f_i^{orig,sel}}{f_i^{orig,unsel}}\right).$$

Fluorescence polarization binding assays. Fluorescence polarization-based affinity measurements of designs and their evolved variants were performed as described[46] using Alexa488-conjugated DIG (DIG-PEG$_3$-Alexa488). Fluorescence anisotropy (r) was measured in 96-well plate format on a SpectraMax M5e microplate reader (Molecular Devices) with $\lambda_{ex}$=485 nM and $\lambda_{em}$=538 nM using a 515 nm emission cutoff filter. Fluorescence polarization equilibrium competition binding assays were used to determine the binding affinities of DIG10.3 and its variants for unlabeled digoxigenin, digitoxigenin, progesterone, β-estradiol, and digoxin. The inhibition constant for each protein-ligand interaction, $K_i$, was calculated from the measured total unlabeled ligand producing 50% binding signal inhibition ($I_{50}$) and the $K_d$ of the protein-label interaction according to a model accounting for receptor-depletion conditions[46].

Supplementary Methods

Computational Methods. Digoxigenin binders were designed using an updated version[1] of RosettaMatch[2] to search for PDB scaffold backbones that can accommodate pre-defined interactions to the ligand followed by RosettaDesign[3] to optimize the binding site amino acid sequences of the matches for ligand binding affinity.

Generation of ligand and ligand conformer library. The 3-dimensional structure of digoxigenin (DIG) was obtained from PDB ID 1LKE[4]. Because our experimental validation and selection methods rely on the presence of a linker that connects the O5 hydroxyl of the DIG molecule to either biotin or carrier protein, we included this linker in our ligand model. Linker atoms were added to DIG using the Build functionality of MacPyMOL (Schrödinger, LLC).

A ligand conformer library was generated by sampling conformations around the C3-O5 and N1-C26 bonds at −60°±30°, 60°±30°, and 180°±30°. Conformers were rejected if there were significant clashes within the molecule by using an intra_fa_rep cutoff value of 0.25 Rosetta energy units (Reu). Although the lactone-cardenoline bond (C17-C20) of the steroid is freely rotatable in solution, we restricted this torsion angle to that found in PDB ID 1LKE and PDB ID 1IGJ for simplicity.

Scaffold selection. A set of 401 scaffolds was generated for use as input structures for matching. This set contained scaffold proteins previously used for enzyme design projects within our lab[5-7] as well as structural homologs[8] of a subset of these scaffolds (PDB codes 1m4w, 1oho, 1a53, 1dl3, 1e1a and 1thf) having a DALI Z-score cutoff value of 8 from the input search model. These five scaffolds were chosen because of previous enzyme-design successes in these fold classes[5-7] and/or because of their thermostability. Directed evolution experiments have shown that more stable scaffolds can acquire new functions more easily than their less stable counterparts[9,10]. All scaffolds are <350 amino acids, have been expressed previously in E. coli, and were stripped of their cognate bound small molecules and water molecules before use. To identify residue positions to be used for matching in the homolog scaffolds, each homolog crystal structure was superimposed on that of its parent scaffold using the CEAlign plug-in of the PyMOL molecular visualization program, and then homolog residue positions within 5.0 Å of any ligand heavy atom present in the parent scaffold were identified. For PDBs 1a53, 1d13 and 1oho, ligands present in the crystal structures were used in this search. For 1m4w, 1e1a and 1thf, ligand positions from the computational design models of a retroaldolase (RA60)[5], a Diels-Alderase (DA_20)[7], and a Kemp Eliminase (KE_007)[6] were used, respectively.

Geometric placement of ligand using a set of pre-selected interactions (matching). Geometric criteria for enforcing binding site interactions were determined by inspecting structures of digoxin bound to the anti-digoxigenin antibody 26-10, PDB ID 1IGJ[11], and of digoxigenin bound to the engineered lipocalin DigA16, PDB ID 1LKE[4]. From these structures we defined five interface criteria: (1) hydrogen bond between the lactone carbonyl oxygen O1 and a Tyr side chain, (2) hydrogen bond between the O2 hydroxyl and a histidine or Tyr side chain, (3) hydrogen bond between the O3 hydroxyl and a His or Tyr side chain, (4) hydrophobic packing interaction on the top face of the ligand, and (5) hydrophobic packing interaction on the bottom face of the ligand. Two active site configurations were specified: one having Tyr, Tyr, His, Phe/Tyr, and Phe/Tyr/Trp satisfying design criteria 1-5 (DIG_yyhff), and one having Tyr, His, His, Phe/Tyr/Trp, and Tyr/Trp satisfying design criteria 1-5 (DIG_yhhff).

Geometric criteria were defined using six degrees of freedom between the ligand and the desired interacting side chain using a matching constraints file[1]. Extra rotamer sampling (two half step standard deviations) was performed around all side chain torsion angles. To enforce burial of the lactone head group within a binding pocket, we considered only those residue positions in the binding site that had a minimum of 14 neighboring residues during matching for constraint 1 (hydrogen bond to the lactone carbonyl oxygen). A neighbor was defined as a residue having Cα within 10 Å of the Cα of the binding site position under consideration. Secondary matching[1] was used for constraints 3, 4, and 5. To eliminate high-energy rotamer conformations, a maximum Dunbrack energy (fa_dun) cutoff of 4.5 Reu (unweighted) was used while building rotamers for all constraints. Using these matching criteria, 29,274 and 30,861 matches were found for DIG_yyhff and DIG_yhhff, respectively.

Rosetta sequence design. Active site amino acid sequences of each match were designed to maximize binding affinity to the ligand according to the Rosetta energy function using the enzdes weights set for the energy terms[1,12]. Explicit electrostatics were not used. Design moves were followed by steepest descent gradient minimization in which side chain degrees of freedom and the relative orientation of the ligand with respect to the protein were allowed to minimize freely[13] but backbone minimization was restricted such that Cα atoms were only allowed to move ≤0.05 Å from their pre-minimization positions. Internal torsions of the ligand were allowed to minimize but were constrained to be within 5 degrees of their initial values Two successive rounds of sequence design were used to generate designs. The purpose of the first round was to maximize binding affinity for the ligand[1]. To prevent destabilization of the apo-protein that can result from mutating potentially stabilizing residues having side chains important for core packing, aromatic residues in the scaffold were only allowed to mutate to other aromatics during this round of design.

After the first round, a second round of binding site sequence design was performed on the output files of the first round. The goal of this round was to optimize protein stability while maintaining the binding interface designed during the first round as much as possible. Ligand-protein interactions were up-weighted by a factor of 1.5 relative to intra-protein interactions during sequence optimization in attempt to ensure that the interface binding affinity was maintained, and two different criteria were used to optimize protein stability: (1) native scaffold residues identities were favored by 1.5 Rosetta energy units (Reu), and (2) no more than five residues were allowed to change from identities observed in a multiple sequence alignment (MSA) if (a) these residues were present in the MSA with a frequency greater than 0.6 as specified by a position-specific sequence matrix (PSSM) and, (b) if the calculated $\Delta\Delta G$ for mutation of the scaffold residue to alanine was greater than 1.5 Reu in the context of the scaffold sequence. The $\Delta\Delta G$ for mutation to alanine was estimated as described[14] and PSSM files were generated using NCBI PSI-BLAST. For both the DIG_yhhff and the DIG_yyhff designs, a first method restricted the amino acid identities of the hydrogen bonding (Tyr/His) residues to their pre-selected (matched) identities during the design. For the DIG_yhhff designs, we used an alternative second method in which the matched residues were allowed to mutate to any amino acid subject to the MSA and $\Delta\Delta G$ criteria described above. Designs generated using this latter protocol were filtered to ensure the presence of at least three hydrogen bonds between the protein and the ligand.

Evaluation of designs. Designs passing the filters encoded in the XML files were subjected to several additional filtering criteria. High shape complementary was enforced using by rejecting designs having $S_c$<0.6. Shape complimentary was computed using the CCP4 package v.6.0.2[15] using the $S_c$ program[16] and the Rosetta radii library. A common feature of the engineered DIG-binding lipocalin DigA16 (PDB IDs 1LKE and 1KXO)[4] and the anti-DIG26-10 antibody (PDB IDs 1IGJ and 1IGI)[11] is that the binding site is largely pre-organized; there are very few structural changes between the bound and unbound forms of the proteins. We therefore attempted to enforce pre-organization of the binding-competent conformation of the apo-protein by two metrics: (1) introducing second-shell amino acids that hold the pre-selected residues in place via hydrogen bonding or sterics using Foldit[7], and (2) eliminating designs having Boltzmann-weighted side chain probabilities[18]<0.1 for more than one of the hydrogen bonding residues.

Compatibility of designed sequence with local backbone structure. We reasoned that binding site pre-organization would be compromised if substitution of amino acid side chains during (fixed backbone) design leads to a change in the backbone conformational preference in regions sequence-local to the sites of substitution. Therefore, we developed a metric to estimate the impact of design on local backbone structure and used this metric to discard designs that were predicted to lead to backbone structure changes. Using the structure prediction modules of Rosetta[19], we generated a set of 9-mer fragment structures for each designed and wild type scaffold sequence and compared the average RMSD of these fragments to those of the scaffold backbone structures. If the average RMSD of conformations predicted in these fragments (200 9-mers) near any designed position was greater (>0.8 Å) for the designed sequence than the wild type scaffold sequence, we flagged that region of the designed protein as unlikely to adopt the local backbone conformation of the scaffold protein and rejected that designed protein.

Design Scoring. Following automated filtering, all designs were inspected manually using Foldit[17] and some ligand-proximal residues were manually reverted back to their native scaffold identity to increase the likelihood of design stability. Finally, 17 designs in 14 unique scaffolds were chosen for experimental testing (Supplementary Table 2). For scoring, all design models were relaxed with backbone and side chain heavy atom constraints[20] using Rosetta relax[21].

Modeling directed evolution mutations. Mutations arising from directed evolution studies were modeled using RosettaScripts[12]. Mutations were introduced in the parent model, then residues having Cα within 10 Å of any ligand heavy atom and having Cα within 12 Å of any ligand heavy atom and Cβ closer to any heavy atom in the ligand than Cα were repacked using the soft_rep score function[22]. All side chains, the rigid body orientation of the ligand with respect to the protein, and internal ligand torsions were minimized using the Rosetta energy function with the enzdes weights set. Backbone minimization was restricted such that Cα atoms were only allowed to move ≤0.05 Å from their pre-minimization positions. Ten trajectories were run and the one having the lowest interface energy was selected.

Materials. Digoxigenin, digoxin, digitoxigenin, progesterone, and β-estradiol were purchased from Sigma Aldrich (St. Louis, Mo.) and were used as received. DIG-BSA was purchased from CalBioreagents (San Mateo, Calif., ~10 DIG molecules per BSA). EZ-link-sulfo-NHS-biotin was purchased from Thermo Fisher Scientific (Waltham, Mass.). Ribonuclease A (RNase A) and DIG-NHS were from Sigma Aldrich (St. Louis, Mo.). Reagents and solvents used for the synthesis of the digoxigenin derivatives were purchased from Sigma Aldrich and used without any further purification. Dimethylsulfoxide was stored over activated molecular sieves (Sigma-Aldrich, 4A, beads 8-12 mesh) for at least 24 hours before use. High-resolution mass spectra (HRMS) were collected with a LCQ Fleet Ion Trap Mass Spectrometer (Thermo Scientific). Reverse-phase analytical high-pressure liquid chromatography (RP-HPLC) was run on a Dionex system equipped with a P680 pump, an ASI 100 automatic sample injector and an UltiMate 3000 diode array detector for product visualization using a Waters symmetry C18 column (5 μm, 3.9×150 mm). Reverse-phase preparative high-pressure liquid chromatography was performed on a Dionex system equipped with an UltiMate 3000 pump and an UVD 170U UV-Vis detector for product visualization on a Waters SunFire™ Prep C18 OBD™ 5 μm 19×150 mm Column. Proton and carbon nuclear magnetic resonance (NMR) spectra were recorded at room temperature on a Bruker Avance-III 400 or on a Bruker DRX-600 equipped with a cryoprobe. Chemical shifts (δ) are reported in ppm relative to the solvent residual signals. Synthetic schemes are given in FIG. 21.

Biotinylation of DIG-BSA. DIG-BSA was prepared by reacting 50 µL of a 58 µM solution of DIG-BSA (2.9 nmol) with 8 µL of a 1.8125 mM solution of EZ-link-sulfo-NHS-biotin (14.5 nmol, 5 eq) in PBS for 1 hr at RT. A 10 µL portion of 14.5 mM glycine was added to quench the reaction. After 30 min, the reaction mixture was centrifuged and soluble protein was purified from excess small molecules by repeated rounds of centrifugal concentration and dilution into PBS until the absorbance of the flow-through remained constant.

Synthesis of DIG-RNase-biotin. A 460 µL portion of a 365 µM solution of Ribonuclease A (168 nmol; RNase A) prepared in PBS was reacted with 30 µL of a 9.73 mM solution of EZ-link-sulfo-NHS-biotin (292 nmol, 1.7 eq) prepared in PBS and 10 µL of a 106.3 mM solution of DIG-NHS (1 µmol, 6 eq) prepared in DMSO for 1 hour at RT. A 20 µL portion of 385 mM glycine was added to quench the reaction. After 20 min, the reaction mixture was centrifuged and soluble protein was purified from excess small molecules by repeated rounds of centrifugal concentration and dilution into PBS until the absorbance of the flow-through remained constant.

Synthesis of Biotin-PEG$_3$-NH$_2$ (2) Biotin (1, 13.5 mg, 55.3 µmol, 1 eq) was dissolved in 100 µL of dimethylsulfoxide (DMSO) and diisopropylethylamine (DIEA) was added (19.3 µL, 2 eq). O-(N-succinimidyl)-N,N,N',N'-tetramethyl-uronium (TSTU, 15.0 mg, 0.9 eq) was added and the clear solution was stirred for 10 minutes at room temperature to form the biotin-NHS ester. 4,7,10-Trioxa-1, 13-tridecanediamine (18 mg, 1.5 eq) was dissolved in 200 µL of dry DMSO and the biotin-NHS was added drop wise under vigorous stirring over 5 minutes. The mixture was stirred for a further 10 minutes at room temperature. 1.5 mL of diethyl ether was added to the clear solution and the resulting suspension was centrifuged. The supernatant ether phase was discarded and the remaining oil was purified by preparative RP-HPLC (5 mL/min, 10-100% acetonitrile in 0.1% TFA in H$_2$O). The fractions containing the product were lyophilized to afford 2 as a yellowish liquid (15 mg, 67%). [HRMS (ESI): 447.42 m/z (447.7 m/z expected). $^1$H NMR (400 MHz, DMSO) δ 7.78 (t, 1 H, J=5.6 Hz), 7.70 (m, 2 H), 6.42 (d, 1 H, J=0.2 Hz), 6.37 (m, 1 H), 4.31 (m, 1 H), 4.13 (dd, 1 H, J=7.6, 4.5 Hz), 3.50 (m, 11 H), 3.39 (t, 2 H, J=6.3 Hz), 3.08 (m, 3 H), 2.85 (m, 3 H), 2.05 (t, 2 H, J =7.4 Hz), 1.78 (m, 2 H), 1.61 (m, 4 H), 1.49 (m, 3 H), 1.30 (m, 2 H). $^{13}$C NMR (101 MHz, DMSO) δ 172.4, 163.2, 70.2, 70.1, 70.0, 70.0, 68.6, 67.8, 61.5, 59.7, 55.9, 40.3, 37.3, 36.2, 35.7, 29.9, 28.7, 28.5, 27.7, 25.8.]

Synthesis of Digoxigenin-PEG$_3$-biotin (3) Digoxigenin-NHS ester (1 mg, 1.5 µmol) was dissolved in 100 µL of DMSO and DIEA (0.4 mg, 3.0 µmol) was added, followed by 2 (1.3 mg, 3.0 µmol). The reaction was stirred for 10 minutes at room temperature and then purified by preparative HPLC (5 mL/min, 10-100% acetonitrile in 0.1% TFA in H$_2$O). The fractions containing the product were lyophilized to afford 3 as a yellowish liquid (0.4 mg, 27%). [HRMS (ESI): 990.4 m/z (990.6 m/z expected) $^1$H NMR (400 MHz, DMSO) δ 7.74 (m, 2 H), 7.52 (m, 1 H), 6.44 (s, 1 H), 6.34 (s, 1 H), 5.83 (s, 1 H), 4.88 (m, 3 H), 4.32 (m, 2 H), 4.15 (m, 2 H), 3.77 (m, 1 H), 3.60 (m, 1 H), 3.52 (m, 2 H), 3.47 (m, 2 H), 3.44-3.2 (30 H), 3.08 (m, 2 H), 2.84 (m, 1 H), 2.81 (m, 1 H), 2.60 (m, 1 H), 2.57 (m, 2 H), 2.45 (m, 1 H), 2.05 (m, 2H), 1.74 (m, 2 H), 1.61 (m, 4 H), 1.44 (m, 3 H), 1.25 (m, 2 H), 0.87 (s, 2 H), 0.66 (s, 2 H)]

Synthesis of Alexa488-PEG$_3$-NH$_2$ (5) Alexa Fluor 488 (4, 4.74 mg, 8.9 µmol) was dissolved in 100 µL of DMSO and treated with DIEA (3.1 µL, 17.8 µmol), followed by TSTU (3.22 mg, 10.7 µmol). The reaction was stirred at room temperature for 10 minutes. 4,7,10-Trioxa-1,13-tridecanediamine (3.92 mg, 17.8 µmol) was dissolved in 100 µL of dry DMSO and the Alexa 488 reaction mixture was added drop wise under vigorous stirring over 5 minutes. The clear orange solution was stirred for 10 minutes at room temperature and then purified by preparative HPLC (5 mL/min, 10-100% acetonitrile in 0.1% TFA in H$_2$O). The fractions containing the product were lyophilized to afford 5 as a deep red liquid (2.8 mg, 43%). [HRMS (ESI): 738.3 m/z (738.7 m/z expected). 1H NMR (400 MHz, DMSO) δ 8.74 (m, 1 H), 8.62 (m, 1 H), 8.26 (m, 1 H), 7.62 (m, 2 H), 7.26 (m, 1 H), 6.86 (m, 3 H), 3.54 (m, 4 H), 3.48 (m, 2 H), 3.3-3.4 (6H), 2.83 (m, 2 H), 2.08 (d, 1 H, J=0.7 Hz), 1.84 (m, 2 H), 1.73 (m, 2 H), 1.25 (m, 1 H), 1.10 (t, 4 H, J=7.0 Hz)]

Synthesis of Digoxigenin-PEG$_3$-Alexa488 (6) 5 (0.56 mg, 0.76 µmol) was dissolved in 200 µL of DMSO and treated with DIEA (0.20 mg, 1.52 µmol). Digoxigenin-NHS ester (0.5 mg, 0.8 µmol) was added at once and the reaction stirred for 10 minutes at room temperature and then purified by preparative HPLC (5 mL/min, 10-100% acetonitrile in 0.1% TFA in H$_2$O). The fractions containing the product were lyophilized to afford 6 as a deep red liquid (0.59 µmol, 78%). [$^1$H NMR (400 MHz, DMSO) δ 8.87 (s, 1 H), 8.69 (s, 3 H), 8.27 (dd, 1 H, J=7.9, 1.3 Hz), 7.74 (m, 1 H), 7.54 (m, 2 H), 7.00 (dd, 4 H, J=3.2, 1.6 Hz), 5.81 (s, 1 H), 4.86 (m, 3 H), 3.8-3.5 (31 H), 3.37 (m, 3 H), 3.22 (m, 2 H), 3.16 (s, 2 H), 3.06 (m, 2 H), 2.08 (s, 4 H), 2.02 (t, 2 H, J=7.3 Hz), 1.81 (d, 2 H, J=6.5 Hz), 1.73 (m, 2 H), 1.59 (m, 4 H), 1.43 (m, 7 H), 1.19 (d, 3 H, J=6.2 Hz), 1.07 (m, 2 H), 0.86 (s, 2 H), 0.64 (s, 2 H).]

Gene synthesis. Designs DIG1-17. DigA16, and 3hk4 were ordered from Genscript (Piscataway, N.J.) between the NdeI and XhoI restriction sites of a custom pET29-based vector having an N-terminal FLAG tag and a C-terminal His$_6$ tag (pET29FLAG). Codon usage was optimized for both E. coli and yeast with preference given to E. coli. DNA sequences are given in Supplementary Table 1.

Yeast surface display assays. Designed proteins were tested for binding using yeast-surface display[23]. Designs DIG1-17/pET29FLAG, DigA16/pET29FLAG, and 3hk4/pET29FLAG were subcloned into the NdeI/XhoI cloning sites of pETCON[24]. Designs and control proteins in pET-CON were transformed into EBY100 cells using lithium acetate and polyethylene glycol[25] with dH$_2$O instead of single stranded carrier DNA and were plated on selective media (C -ura -trp). Freshly transformed cells were inoculated into 1 mL of SDCAA media[23] and grown at 30° C., 200 rpm. After ~12 hrs, 1e7 cells were collected by centrifugation at 1,700×g for 3 min and resuspended in 1 mL of SGCAA media to induce protein expression. Following induction for 24-48 hrs at 18° C., 4e6 cells were collected by centrifugation, and washed twice by incubation with PBSF (PBS supplemented with 1 µL of BSA) for 10 min at room temperature Yeast surface protein expression was monitored by binding of anti-cmyc FITC (Miltenyi Biotec GmbH, Germany) to the C-terminal myc epitope tag of the displayed protein. DIG binding was assessed by quantifying the phycoerythrin (PE) fluorescence of the displaying yeast population following incubation with DIG-BSA-biotin, DIG-RNase-biotin, or DIG-PEG$_3$-biotin, and streptavidin-phycoerythrin (SAPE; Invitrogen, Carlsbad, Calif.). In a typical experiment using DIG-BSA-biotin or DIG-RNase-biotin. 4e6 cells were resuspended in 50 µL of a premixed solution of PBSF containing a 1:100 dilution of anti-cmyc FITC, 2.66 µM DIG-BSA-biotin or DIG-RNase biotin, and 664 nM SAPE.

Following a 2-4 hr incubation at 4° C. in the dark on a rotator, cells were collected by centrifugation at 1,700×g for 3 min and washed with 200 μL of PBSF at 4° C. Cell pellets were resuspended in 200 μL of ice-cold PBSF immediately before use. Cellular fluorescence was monitored on an Accuri C6 flow cytometer using a 488 nm laser for excitation and a 575 nm band pass filter for emission. Phycoerythrin fluorescence was compensated to minimize bleed-over contributions from the FITC fluorescence channel.

Two positive controls having different affinities for digoxigenin were used to assess the binding assay: DigA16[26], and a commercially available anti-DIG monoclonal antibody 9H27L19 (Life Technologies). Experiments using DigA16 were conducted in an identical fashion to designs DIG1-17. For those employing the DIG antibody, two tandem Z domains of protein A (ZZ domain)[27,28], were displayed on the yeast cell surface. Washed cells were resuspended in 20 μL of PBSF with 2 μL of rabbit anti-DIG mAB 9H27L19 (Invitrogen, Carlsbad, Calif.). Following a 30-min incubation at 4° C. on a rotator, excess antibody was removed by washing the cells with 200 μL of PBSF. Labeling reactions were then performed as above. Negative controls for binding were the ZZ domain without mAB and an orthogonal gp120-based library available in the Baker lab (S2). FlowJo software version 7.6 was used to analyze all flow cytometry data presented here.

Competition assays with free digoxigenin were performed as above except that between 750 μM and 1.5 mM of digoxigenin (Sigma Aldrich, St. Louis, Mo.) prepared as a stock solution in MeOH was added to each labeling reaction mixture. Control experiments performed in a similar manner showed that the small amount of MeOH added does not affect the fluorescence or binding properties of SAPE (data not shown).

Knockout mutations. Knockout mutations were introduced into the appropriate DIG design in pETCON or pET29b(+) by the method of Kunkel[29]. These variants included the single point mutants VI 17R, Y101F, Y115F, and Y34F and the triple mutant Y101F/Y115F/Y34F for DIG10, the single point mutants W119R, H58A, Y84F, and Y97F and the double mutant Y115F/Y84F for DIG5, the single point mutants V86R, H011A and the triple mutant Y10F/H101A/Y103F for DIG8, and single point mutants Y34F, Y101F, Y115F, the double mutant Y99F/Y101F, the triple mutant Y34F/Y99F/Y101F, and the quadruple mutant Y34F/Y99F/Y101FYI 15F for DIG10.3. Oligos were ordered from Integrated DNA Technologies, Inc. (Coralville, Iowa) and are listed in Supplementary Table 12 with the mutagenized region(s) highlighted in red.

Recursive PCR assembly of 1z1s. The gene for 1z1s having additional pETCON overlap fragments at either end for yeast homologous recombination was assembled via recursive PCR. Oligo sequences were designed using DNA-Works[30] and are given in Supplementary Table 13. Oligos were ordered from Integrated DNA Technologies, Inc. (Coralville, Iowa). A 2 μL portion of a 2.5 μM stock solution of each oligo was combined and the mixture was added to 8 μL of 1.25 mM dNTPs, 20 μL of 5× Phusion buffer HF, 3 μL of DMSO, and 1 μL of Phusion high-fidelity polymerase (NEB, Waltham, Mass.) in 100 μL. Full-length gene product was assembled by 30 cycles of PCR (98° C. 10 s, 61° C. 30 s. 72° C. 15 s)

Correctly assembled PCR product was amplified by a second round of PCR. Reaction product (5 μL) was combined with 2 μL of 10 μM pCTCON2f (Supplementary Table 14), 2 μL of 10 μM pCTCON2r (Supplementary Table 14), 8 μL of 1.25 mM dNTPs, 20 μL of 5× Phusion buffer HF, 3 μL of DMSO, and 1 μL of Phusion high-fidelity polymerase (NEB, Waltham, Mass.) in 100 μL. Product was obtained by 30 cycles of PCR (98° C. 10 s, 60° C. 30 s, 72° C. 15 s). Following confirmation that a single band at the correct molecular weight by 1% agarose gel electrophoresis, the PCR product was purified using a Qiagen PCR cleanup kit (Qiagen) and eluted in dH$_2$O Yeast EBY100 cells were transformed with 240 ng of 1z1s gene DNA and 400 ng of gel-purified pETCON digested with NdeI and XhoI using lithium acetate and polyethylene glycol[25] with dH$_2$O instead of single-stranded carrier DNA. The correct sequence was confirmed by colony PCR and gene sequencing, and plasmids from these colonies were harvested using a Zymoprep Yeast Miniprep II kit (Zymo Research Corporation, Irvine, Calif.).

DIG10 site-saturation mutagenesis library (directed evolution round 1a). A DIG10 single site-saturation mutagenesis (SSM) library was constructed by Kunkel mutagenesis[29] using degenerate NNK primers targeting the following 34 amino acids positions: S10, L11, L14, W22, L32, Y34, A37, P38, G40, H41, H54, M55, L57, F58, Y61, V62, V64, F66, F84, G86, G88, H90, V92, S93, L97, A99, Y101, S103, Y115, V117, F119, V124, A127, and L128. These positions were chosen from the model based on the following requirements: (1) they have Cα within 7 Å of any ligand heavy atom, and/or (2) they have Cα within 9 Å of any ligand heavy atom and Cβ closer to any heavy atom in the ligand than Cα. The theoretical library size was 1088 clones. Primers were ordered from Integrated DNA Technologies (Coralville, Iowa).

Kunkel mutagenesis of each position was carried out independently. DNA from each reaction was dialyzed into dH$_2$O using a 0.025 μm membrane filter (Millipore, Billerica, Mass.), and then the dialyzed reaction mixtures were pooled, concentrated to a volume of <10 μL using a Savant SpeedVac centrifugal vacuum concentrator, and transformed into yeast strain EBY100 using the method of Benatuil[31], yielding 2.5e5 transformants. After transformation, cells were grown in 250 mL of SDCAA media for 36 hrs at 30° C. Cells (5e8) were collected by centrifugation at 1,700×g for 4 min, resuspended in 50 mL of SGCAA media, and induced at 18° C. for 24 hrs Cells were subjected to three rounds of permissive cell sorting (Supplementary Table 8). For each round of sorting, cells were washed and then labeled with a pre-incubated mixture of 2.66 μM DIG-BSA-biotin, 644 nM SAPE, and anti-cmyc-FITC as noted above for single clones. After each sort, cells were grown in SDCAA for 24 hrs and then induced in SGCAA for 24 hrs before the next sort. After the final sort, the mean compensated PE fluorescence of the expressing population of the sorted cells was considerably higher than that of DIG10, indicating the presence of a point mutant(s) with increased binding affinity After each sort, a portion of cells were plated and grown at 30° C. Plasmids from individual colonies were harvested using a Zymoprep Yeast Miniprep II kit (Zymo Research Corporation, Irvine, Calif.) and the gene was amplified by 30 cycles of PCR (98° C. 10 s, 61° C. 30 s, 72° C. 15 s) using Phusion high-fidelity polymerase (NEB, Waltham, Mass.) with the pCTCON2r and pCTCON2f primers. Sanger sequencing (Genewiz, Inc., South Plainfield, N.J.) was used to sequence at least 10 colonies from each population.

DIG10 combinatorial mutagenesis library (directed evolution round 1b). Beneficial mutations identified in the DIG10 SSM library were combined by Kunkel mutagenesis[29] using degenerate primers. At each mutagenized position, the original DIG10 amino acid and chemically similar amino acids to those identified were also allowed, resulting in a combinatorial library. Amino acid substitutions included S, A, or M at position S10, L, H, or Q at position L11, A or P at position A37, I, L, V, F, or M at position V62, I, L, V, F, or M at position V64, H, T, or N at position H90, I, L, V, F, or M at position V17, and A or P at position A127. The theoretical library size was 1.35e4 clones. Primers were ordered from Integrated DNA Technologies, Inc. (Coralville, Iowa).

Four independent Kunkel reactions using different oligo concentrations ranging from 36 nM to 291 nM during polymerization were performed to minimize sequence-dependent priming bias. For the same reason, oligos encoding native substitutions contained at least one codon base change. Library DNA was pooled, prepared as above, and transformed into electrocompetent $E.$ $coli$ strain BL2 I(DE3) cells (1800 V, 200 Ω, 25 μF), yielding 8e4 transformants. Library plasmid DNA was isolated from expanded cultures using a Qiagen miniprep kit. Gene insert was amplified from 10 ng of library DNA by 30 cycles of PCR (98° C. 10 s, 61° C. 30 s, 72° C. 15 s) using Phusion high-fidelity polymerase (NEB, Waltham, Mass.) with the pCTCON2r and pCTCON2f primers.

Yeast EBY100 cells were transformed with 4.0 μg of PCR-purified DNA insert and 1.0 μg of gel-purified pET-CON digested with NdeI and XhoI using the method of Benatuil[31], yielding 8e5 transformants. After transformation, cells were grown in 150 mL of low pH SDCAA media supplemented with Pen/Strep for 48 hrs at 30° C. Cells (5e8) were collected by centrifugation at 1,700×g for 4 min, resuspended in 50 mL of SGCAA media, and induced at 18° C. for 24 hrs Cells were subjected to seven rounds of cell sorting. For the first four rounds, cells were washed and then labeled with a pre-incubated mixture of DIG-BSA-biotin, SAPE, and anti-cmyc-FITC as noted above for single clones. Label concentrations for rounds one through four were: (1) 1 μM DIG-BSA-biotin and 250 nM SAPE, (2) 750 nM DIG-BSA-biotin and 187.5 nM SAPE. (3) 50 nM DIG-BSA-biotin and 12.5 nM SAPE, and (4) 5 nM DIG-BSA-biotin and 1.25 nM SAPE. For rounds five through seven, DIG-RNase-biotin was used in a multistep labeling procedure to minimize selection for carrier protein (BSA) binding and because this procedure showed a larger dynamic range in several control experiments. In these experiments, cells were washed as before, labeled with DIG-RNase-biotin for 3-4 hrs at 4° C., and then treated with a solution of PBSF containing a 1:100 dilution of SAPE and a 1:100 dilution of anti-cmyc-FITC (secondary label) for <15 min at 4° C. before washing and sorting. DIG-RNase-biotin label concentrations were 10 pM, 5 pM, and 5 pM for rounds five through seven, respectively.

At least 10 clones from each round were sequenced as noted for the DIG10 SSM library. After seven rounds, the library converged to two sequences differing by a single point substitution: DIG10.1a, harboring the S10A substitution, and DIG10. b, containing S10M (Supplementary FIG. 5). Mutations common to both DIG10.1a and DIG10.1 b were V62M, V64I, V117L, and A127P. Analysis of both clones using the multistep labeling procedure with 5 pM DIG-RNase-biotin showed that DIG10.1a had a slightly higher signal for mean PE fluorescence of the expressing population than did DIG10.1 b.

DIG10.1L library (directed evolution round 2). Library DNA was a mixture of DNA from DIG10.IL_f1, DIG10.IL_f2, and a third library (DIG10.IL_3) combining mutations from the two fragment libraries (see section on Next-Gen Library Construction). For DIG10.1L_3, the library was constructed using the oligos DIG10.1L_hr1, DIG10.1L_f1a_rc_variable, DIG10.1L_f1b_variable, DIG10.1L_f2 rc_variable, and DIG10.1 L_hr2 and the procedures detailed below Yeast EBY100 cells were transformed with a mixture of DNA insert from DIG10.IL_f1 (3.0 μg), DIG10.1L_f2 (3.0 μg), and DIG10.IL_3 (24.0 μg) and 10.0 μg of gel-purified pETCON digested with NdeI and XhoI using the method of Benatuil[31], yielding 1.5e7 transformants. After transformation, cells were grown for 24 hrs in 250 mL of low-pH SDCAA media supplemented with Pen/Strep at 30° C., passaged once, and grown for an additional 24 hrs under the same conditions. Cells (5e8) were collected by centrifugation, resuspended in 50 mL of SGCAA, and induced overnight at 18° C.

Cells were subjected to five rounds of cell sorting using monovalent DIG-PEG$_3$-biotin and the multistep labeling procedure detailed for directed evolution round 1b sorts five through seven to increase stringency by avoiding avidity effects. DIG-PEG$_3$-biotin label concentrations were 80 nM, 80 nM, 50 nM, 1 nM, and 1 nM for the five rounds. After the final sort, the mean compensated PE fluorescence of the expressing population of the sorted cells was considerably higher than that of DIG10.2, indicating the presence of a mutant(s) with increased binding affinity.

At least 10 clones from each round were sequenced as noted for the DIG10 SSM library. After four rounds, the library converged to one sequence (DIG10.2) having the two loop mutations A37P and H41Y, which were two of the most enriched single point mutations identified in the next-generation sequencing experiment.

DIG10.2 combinatorial library based on deep sequencing data (directed evolution round 3). Mutations having normalized next-generation sequencing enrichment values $(\Delta E_i^x) > \sim 3.5$ were combined by Kunkel mutagenesis[29] using degenerate primers. DIG10.2 was used as the library template. At each mutagenized position, the original DIG10.2 amino acid and chemically similar amino acids to those identified were also allowed, resulting in a combinatorial library. Amino acid substitutions included C or S at position C23, F, H, or Y at position F45, M or F at position M62. H, I, L, F, or Y at position H90. V or A at position V92, A, V, I, T, F, or Y at position A99, S, A, or V at position S103, L, V, or W at position L105, I or F at position I112, V or F at position V124, and P, I, L, or V at position P127. The theoretical library size was 1.04e5 clones. Primers were ordered from Integrated DNA Technologies (Coralville, Iowa).

Four Kunkel reactions using different oligo concentrations ranging from 36 nM to 291 nM during polymerization and two Kunkel reactions using reduced oligo concentrations for the M62M substitution relative to the concentrations of the M62F substitution were performed to minimize sequence-dependent priming bias. For the same reason, oligos encoding native substitutions contained at least one codon base change. Library DNA was pooled, prepared as above, and transformed into $E.$ $coli$ strain ElectroMAX DH10B (Invitrogen, Carlsbad, Calif.) cells (2500 V, 200 Ω, 25 μF), yielding 1.6e7 transformants. Library plasmid DNA was isolated from expanded cultures using a Qiagen miniprep kit. Gene insert was amplified from 10 ng of library DNA by 30 cycles of PCR (98° C. 10 s, 61° C. 30 s, 72° C. 15 s) using Phusion high-fidelity polymerase (NEB, Waltham, Mass.) with the pCTCON2r and pCTCON2f primers.

Yeast EBY100 cells were transformed with 6.0 μg of PCR-purified DNA insert and 2.0 μg of gel-purified pET-CON digested with NdeI and XhoI using the method of Benatuil[31], yielding 5e6 transformants. After transformation, cells were grown in 150 mL of low pH SDCAA media supplemented with Pen/Strep for 48 hrs at 30° C. Cells (5e8) were collected by centrifugation at 1.700×g for 4 min and resuspended in 50 mL of SGCAA media. Cells were induced at 18° C. for 24 hrs.

Cells were subjected to four rounds of cell sorting (FIG. 13). The first three sorts utilized monovalent DIG-PEG$_3$-biotin and the multistep labeling procedure detailed for directed evolution round 1b sorts five through seven to increase stringency by avoiding avidity effects. DIG-PEG$_3$-biotin label concentrations were 400 pM, 20 pM, and 20 pM for the first three rounds. For the fourth round, an off-rate selection[24] was used to better discriminate between high affinity binders. Cells (4e6) were washed and labeled with 20 pM DIG-PEG$_3$-biotin, as described above. Labeled cells were collected by centrifugation at 1,700×g for 4 min and resuspended in 100 μL of 100 nM DIG in PBSF. Cells were incubated with free DIG for 20 min at room temperature (20 min was found to be the half-life of the DIG10.2-DIG-PEG$_3$-biotin complex in off-rate experiments) collected by centrifugation, labeled with secondary label as described above, washed, and sorted. After the final sort, the mean compensated PE fluorescence of the expressing population of the sorted cells was considerably higher than that of DIG10.2, indicating the presence of a mutant(s) with increased binding affinity.

At least 10 clones from each round were sequenced as noted for the DIG10 SSM library. After four rounds, the library converged to one sequence (DIG10.3) having the mutations C23S, H90L, V92A, A99Y, S103A, and L105W.

Next-generation DIG10.1 library construction and selections. Paired-end 151 Illumina sequencing was used to simultaneously assess the effects of mutation on binding of DIG10.1 to digoxigenin at 39 amino acid positions within the binding site pocket. Two libraries were constructed: an N-terminal library with mutations between residues S10 and F66 (fragment 1 library—DIG10.IL_f1) and a C-terminal library with mutations between residues F84 and L128 (fragment 2 library—DIG10.IL_f2). For each library, the full-length DIG10.1 gene having additional pETCON overlap fragments at either end for yeast homologous recombination was assembled via recursive PCR. To introduce mutations, we used degenerate PAGE-purified oligos in which selected positions within the binding site were doped with a small amount of each non-native base at a level expected to yield 1-2 mutations per gene (TriLink BioTechnologies, San Diego, Calif.). All other wild-type oligos were also PAGE-purified (Integrated DNA Technologies). For DIG10.IL_f1, bases coding for the following 20 amino acid positions were allowed to vary: A10, L11, L14, W22, C23, F26, L32, Y34, A37, P38, G40, H41, F45, H54, M55, F58, Y61, M62, I164, and F66. For DIG10. L_f2, bases coding for the following 19 amino acid positions were allowed to vary: F84, G86, G88, H90, V92, S93, G95, L97, A99, Y101, S103, L105, 1112, Y115, L117, F119, V124, P127, and L128.

For assembly of DIG10.1L_f1, 2 μL of 2.5 μM DIG10.1L_hr1, 2 μL of 2.5 μM DIG10.1L_f1a_rc_variable, 2 gμL of 2.5 μM DIG10.1L_f1b_variable, 2 μL of 2.5 μM DIG10.IL_f2_rc_WT, and 2 μL of 2.5 μM DIG10.1L_hr2 were combined with 8 μL of 1.25 mM dNTPs, 20 μL of 5× Phusion buffer HF, 3 μL of DMSO, and 1 μL of Phusion high-fidelity polymerase (NEB, Waltham, Mass.) in 100 μL.

Reaction mixtures for assembly of DIG10.1l_f2 were the same, except that DIG10.1L_f1a_rc_variable, DIG10.1L_f1b_variable, and DIG10.1L_f2_rc_WT were substituted with DIG10.1L_f1a_rc_WT, DIG10.1L_f1b_WT, and DIG10. IL_f2_rc_variable, respectively. Full-length products were assembled by 30 cycles of PCR (98° C. 10 s, 61° C. 30 s, 72° C. 15 s).

Correctly assembled PCR products were amplified by a second round of PCR. Reaction products (5 μL) were combined with 2 μL of 10 μM DIG10.IL_assembly_fwd, 2 μL of 10 μM DIG10.IL_assembly_rev, 8 μL of 1.25 mM dNTPs, 20 μL of 5× Phusion buffer HF, 3 μL of DMSO, and I μL of Phusion high-fidelity polymerase (NEB, Waltham, Mass.) in 100 μL. Products were amplified by 30 cycles of PCR (98° C. 10 s, 60° C. 30 s, 72° C. 15 s). Following confirmation of a single band at the correct molecular weight by 1% agarose gel electrophoresis. PCR products were purified using a Qiagen PCR cleanup kit (Qiagen) and eluted in ddH$_2$O.

Yeast EBY100 cells were transformed with 5.4 μg of library DNA insert and 1.8 μg of gel-purified pETCON digested with NdeI and XhoI using the method of Benatuil[31], yielding 4e6 and 3e6 transformants for the DIG10.1 L_f1 and DIG10.1 L_f2 libraries, respectively. After transformation, cells were grown for 24 hrs in 100 mL of low-pH SDCAA media supplemented with Pen/Strep at 30° C., passaged once, and grown for an additional 24 hrs under the same conditions. Cells (5e8) were collected by centrifugation, resuspended in 50 mL of SGCAA, and induced overnight at 18° C.

Induced cells (3e7) were labeled with 4 μL of anti-cymc-FITC (Miltenyi Biotec GmbH, Germany) in 200 μL of PBSF for 20 min (DIG10.1L_f1) or 60 min (DIG10.1L_f2) at 4° C. Then, labeled cells were washed with PBSF and sorted. In this first round of sorting, all cells showing a positive signal for protein expression were collected (FIG. 10). Cells were recovered overnight in ~1 mL of low-pH SDCAA supplemented with Pen/strep at 30° C., pelleted by centrifugation at 1,700×g for 4 min, resuspended in 5 mL of low-pH SDCAA supplemented with Pen/strep, and grown for an additional 24 hrs at 30° C. Cells (2e7) were collected by centrifugation, resuspended in 2 mL of SGCAA, and induced overnight at 18 NC.

Induced cells from expression-sorted DIG10.1L_f1 (2e7 cells), expression-sorted DIG10.1 L_f2 (2e7 cells), and two DIG10.1a reference samples (5e6 cells per sample) were washed with 600 μL of PBSF and then labeled with 100 nM of DIG-PEG$_3$-biotin in 400 μL of PBSF for the libraries or 200 μL of PBSF for the reference samples for >3 hrs at 4° C. Labeled cells were washed with 200 μL of PBSF, then incubated with a secondary label solution of 0.8 μL of SAPE (Invitrogen) and 4 μL of anti-cymc-FITC (Miltenyi Biotec GmbH, Germany) in 400 μL of PBSF for 8 min at 4° C. Cells were washed with 200 μL PBSF, resuspended in either 800 μL μL of PBSF for the libraries or 400 μL of PBSF for the reference samples, and sorted (FIG. 10). Each library was sorted according to two different stringency conditions: (1) clones having binding signals higher than that of DIG10.1a (DIG10.1_f1_better and DIG10.1_f2 better), and (2) clones having binding signals equivalent to or higher than that of DIG10.1a (DIG10.1_f1_neutral and DIG10.1_f2_neutral). Collected cells were recovered overnight in ~1 mL of low-pH SDCAA supplemented with Pen/strep at 30° C., pelleted by centrifugation at 1,700×g for 4 min, resuspended in 2 mL of low-pH SDCAA supplemented with Pen/strep, and grown for an additional 24 hrs at 30° C. Cells (2e7) were resuspended in 2 mL of SGCAA and induced overnight at 18° C.

To reduce noise from the first round of cell sorting, the sorted libraries were labeled and subjected to a second round of cell sorting using the same conditions and gates as in the first round (FIG. 10). Collected cells were recovered overnight in 800 μL of low-pH SDCAA supplemented with Pen/strep at 30° C., pelleted by centrifugation at 1,700×g for 4 min. resupended in 2 mL of low-pH SDCAA supplemented with Pen/strep, and grown for an additional 24 hrs at 30° C.

One hundred million cells from the expression-sorted DIG10.1L_f2 and DIG10.1L_f2 libraries and at least 2e7 cells from doubly-sorted DIG10.1_f1_better and DIG10.1_f2_better were pelleted by centrifugation at 1,700×g for 4 min, resuspended in 1 mL of freezing solution (50% YPD, 2.5% glycerol), transferred to cryogenic vials, slow-frozen in an isopropanol bath, and stored at −80° C. until further use.

Next-generation library sequencing. Library DNA was prepared as detailed previously[32]. Illumina adapter sequences and unique library barcodes were appended to each library pool through PCR amplification using population-specific HPLC-purified primers (Integrated DNA Technologies. Coralville, Iowa). The library amplicons were verified on a 2% agarose gel stained with SYBR Gold (Invitrogen) and then purified using an Agencourt AMPure XP bead-based purification kit. (Beckman Coulter, Inc.) Each library amplicon was denatured using NaOH and then diluted to 6 pM. A sample of PhiX control DNA (Illumina, Inc., San Diego, Calif.) was prepared in the same manner as the library samples and added to the library DNA to create high enough sample diversity for the Illumina base-calling algorithm. The final DNA sample was prepared by pooling 300 μL of 6 pM PhiXcontrol DNA (50%). 102 μL of 6 pM expression-sorted DIG10_1L_f1 (17.0%), 102 μL of 6 pM expression-sorted DIG10_1L_f2 (17.0%), 33 μL of 6 pM DIG10_1L_f1_neutral (5.5%), 33 μL of 6 pM DIG10_L_f2_neutral (5.5%), 15 μL of 6 pM DIG10_1L_f1_better (2.5%), and 15 μL of 6 pM DIG10_L_f2_better (2.5%). DNA was sequenced in paired-end mode on an Illumina MiSeq using a 300-cycle reagent kit and custom HPLC-purified primers (Integrated DNA Technologies, Inc., Coralville, Iowa).

Processing of sequencing results. Data from each next-generation sequencing library was demultiplexed using the unique library barcodes added during the amplification steps. Of a total 5,630,105 paired-end reads, 2,531,653 reads were mapped to library barcodes. For each library, paired end reads were fused and filtered for quality (Phred≥30). The resulting full-length reads were aligned against the relevant segments of the DIG10.1a sequence using scripts from the software package Enrich[33]. For single mutations having 7 counts in the original input library, a relative enrichment ratio between the input library and each selected library was calculated[32,34,35]. A pseudocount value of 0.3 was added to the total reads for each selected library mutation, to allow calculation of enrichment values for mutations that disappeared completely during selection.

Protein expression and purification. Selected DIG designs and variants were expressed in E. coli in pET29FLAG or with a TEV protease-cleavable His$_6$ purification tag (pET29-TEV-His$_6$). For the latter, DIG genes were amplified from the appropriate pETCON-based plasmid using a forward primer and a reverse primer harboring a TEV-protease recognition insertion sequence. The PCR products were digested with NdeI and XhoI and ligated into similarly digested pET29b(+). Ligation products were transformed into Rosetta 2 (DE3) cells for expression. Rosetta 2 (DE3)/pET29b(+) cells were grown in 1L of LB or TB medium at 37° C. to an O.D.$_{600}$ of ~0.7, and then protein expression was induced by the addition of 0.5 mM IPTG (isopropyl-f3-D-thiogalactopyransoide). Cultures were incubated at 37° C. for 3-4 hrs or at 18° C. for 18 hrs and then harvested by centrifugation at 1,912×g for 20 min. Cell pellets were stored at −20° C. until further use.

Proteins were purified by gravity flow chromatography over Ni-NTA resin (Qiagen, Hilden, Germany) columns. Frozen cell pellets were resuspended in 15 mL of wash buffer (PBS pH 7.4, 30 mM imidazole) supplemented with 300 μL of 100 mM phenylmethanesulfonyl fluoride (PBSF; Sigma Aldrich, St. Louis, Mo.) prepared in neat ethanol, 2 mg/mL of lysozyme, and 0.2 mg/mL of DNAse I. Cells were lysed by sonication for a total of 4 min (30 s on, 20 s off) using a Branson sonifier at 75% power. Insoluble material was removed by centrifugation at 38,724×g for 30 min, and particulate matter was further removed from the supernatant by filtration through a 0.45 μm syringe filter. Supernatant was then passed through gravity columns containing 3 mL of Ni-NTA resin (Qiagen, Hilden, Germany) equilibrated in wash buffer. Bound proteins were washed with 45 mL of wash buffer and then eluted in 20 mL of elution buffer (PBS pH 7.4, 200 mM imidazole). Proteins were concentrated to ~5-40 mg/mL using Vivaspin 5 kD MWCO centrifugal concentration devices (Sartorium Stedim Biotech GmbH, Goettingen. Germany) and imidazole was removed by dialysis (3×2 L) into PBS pH 7.4 at 4° C.

Yields for the DIG designs expressed in pET29FLAG are given in Supplementary Table 2. Typical yields for DIG10-TEV-his$_6$, DIG10.1a-TEV-his$_6$, DIG10.2-TEV-hiss, DIG10.3-TEV-his$_6$, DIG10.3-TEV-his$_6$ variants, and 1z1s-TEV-his range from 10 to 60 mg/L. For all solution experiments, protein concentrations were determined from absorbance at 280 nm measured on a NanoDrop spectrophotometer (Thermo Scientific) using extinction coefficients calculated from primary amino acid sequences.

Size-exclusion chromatography. Protein oligomerization states were assessed by size exclusion chromatography on an ÄKTA FPLC (GE Healthcare) using a Superdex 75 10/300 GL column equilibrated in running buffer (25 mM Tris-HCl pH 7.4, 250 mM NaCl). Proteins were run over the column at a flow rate of 0.5 mL/min. Horse heart cytochrome c (29 kDa), bovine erythrocytes carbonic anhydrase (12.4 kDa), and bovine aprotinin (6.5 kDa) molecular weight standards (Sigma Aldrich, St. Louis, Mo.) were analyzed in the same manner as the protein samples. Under these conditions, cytochrome c, carbonic anhydrase, DIG10-TEV-his$_6$ (expected MW of monomer: 17.9 kDa). DIG10.1b-TEV-his$_6$ (expected MW of monomer: 17.9 kDa), DIG10.2$_t$-his$_6$ (see below; expected MW of monomer: 15.9 kDa), DIG10.3-TEV (the his$_6$ tag was cleaved with TEV protease; expected MW of monomer: 16.9 kDa), and DIG5-TEV-his$_6$ (expected MW of monomer: 17.8 kDa) eluted at 12.05 mL, 13.65 mL, 11.88 mL, 11.81 mL, 11.40 mL, 11.35 mL, and 11.78 mL, respectively (Supplementary FIG. 13). For preparative runs, pure protein-containing fractions were identified by absorbance at 280 nm and by SDS gel electrophoresis. Analytical superdex 75 gel filtration analyses of 100 μM DIG10.3-TEV-his and 100 μM DIG10.3-TEV-his$_6$ pre-incubated with 500 μM DIG for ~60 min at room temperature were also conducted using the above procedure.

Under the conditions, DIG10.3 and the DIG10.3-DIG complex eluted at 11.29 mL and 10.71 mL, respectively (Supplementary FIG. 13).

Preparation of samples for crystallography. Crystallographic trials with the DIG10-based C-terminal TEV-his$_6$ constructs (cleaved with TEV protease or un-cleaved) failed to yield diffraction-quality crystals. All 1z1s-based designs contained a 12 residue C-terminal tail that was disordered in the structure of 1z1s but was maintained when we ordered the designs in case it was necessary for protein stability or folding. To reduce entropic effects from this disordered tail that might prevent crystal formation, we cloned the DIG10 designs into new pET29b(+)-based constructs in which all 12 residues of this tail were eliminated and a non-cleavable his$_6$ tag was placed immediately after the last ordered residue (DIG10$_t$-his$_6$, DIG10.1a$_t$-his$_6$, DIG10.2$_t$-his$_6$, and DIG10.3$_t$-his$_6$).

Truncated samples were expressed and purified by gravity flow over Ni-NTA resin using the above procedure. Typical expression yields were comparable to their un-truncated, TEV-cleavable His$_6$-tagged counterparts (see above). Preparative size exclusion chromatography was used to further purify all proteins for crystallization attempts using the above procedure.

Crystallization. Purified DIG10 and its evolved variants were incubated at 4° C. with 1 mM digoxigenin for 16-20 hours. The protein-ligand complex was then screened using several commercially available sparse matrix crystallization screens using a nanoliter drop volume crystallization robot (TTP LabTech 'Mosquito'). Potential hits were scaled up into vapor diffusion plates with reservoir solution to protein-ligand complex at a ratio of 1:1. Several diffraction quality crystals were obtained for DIG10.2$_t$-his$_6$ and DIG10.3$_t$-his$_6$. Crystals of DIG10.2$_t$-his$_6$ were grown at a concentration of 15 mg mL$^{-1}$ in 0.1 M Acetate pH 5.5, 1.5% MPD, 2.5 M Sodium chloride and 12% PEG1500. Crystals of DIG10.3$_t$-his$_6$ were grown at a concentration of 13.5 mg ml$^{-1}$ in 0.2 M Ammonium acetate, 0.1 M Bis-Tris pH 5.5 and 20% PEG3350. DIG10.2$_t$-his$_6$ and DIG10.3$_t$-his$_6$ crystals were transferred to artificial mother liquor containing 20% Sucrose or Glycerol, respectively, then individually removed in fiber loops and flash frozen in liquid nitrogen.

Crystallographic data collection and processing. Datasets from crystals of DIG10.2$_t$-his$_6$ and DIG10.3$_t$-his$_6$ were collected at the Advanced Light Source (ALS) synchrotron facility (Berkeley, Calif.) on beamline 5.0.2 using a CCD area detector. Data for DIG10.2$_t$-his$_6$ corresponded to 360° of 1° diffraction exposures collected at a distance of 180 mm and exposure times of 1 second per 1° oscillation. Data for DIG10.3$_t$-his$_6$ corresponded to full 360° of 1° diffraction exposures collected at a distance of 230 mm and exposure times of 1 second per 1° oscillation.

Data was processed using the HKL2000 software package[36]. Molecular replacement was performed using program PHASER[37] in the CCP4 software suite[38,39] using *Pseudomonas aeruginosa* hypothetical protein PA3332 (PDB 1Z1 S) as the model[40]. Refinement and model building were carried out using Refmac5[41] and COOT (Crystallography Object-Oriented Toolkit)[42], respectively. The geometric quality of the final model was validated using ProCheck[43], SFCheck[44] and MolProbity[45], as well as the validation tools provided by the RCSB Protein Data Base[46].

The diffraction dataset collected from the DIG10.3$_t$-his$_6$, crystal collected could only be processed to 3.2 Å resolution in space group C2. Significant disorder was displayed in several of the independent copies of protein-ligand complex in the asymmetric unit, which resulted in very high average B-factors.

Fluorescence polarization equilibrium binding assays. Fluorescence polarization-based affinity measurements of designs and their evolved variants were performed as noted previously[47] using Alexa488-conjugated DIG (DIG-PEG$_3$-Alexa488). In a typical experiment, the concentration of DIG-PEG$_3$-Alexa488 was fixed below the K$_d$ of the interaction being monitored and the effect of increasing concentrations of protein on the fluorescence anisotropy of Alexa488 was determined. Fluorescence anisotropy (r) was measured in 96-well plate format on a SpectraMax M5e microplate reader (Molecular Devices) with $\lambda_{ex}$=485 nM and $\lambda_{em}$=538 nM using a 515 nm emission cutoff filter. In all experiments, PBS (pH 7.4) was used as the buffer system and the temperature was 25° C. DIG-PEG$_3$-Alexa488 solutions were prepared from a 1 mM stock in DMSO. Equilibrium dissociation constants (K$_d$) were determined by fitting plots of the anisotropy averaged over a period of 20 to 40 min after reaction initiation versus protein concentration as described previously[47]. Reported K$_d$ values represent the average of at least three independent measurements with at least two separate batches of purified protein Design-TEV-his$_6$ constructs were used for all measurements. The [DIG-PEG3-Alexa488] used for sets of experiments on each protein are as follows: DIG5: 2 pM, DIG10: 2 pM, 1z1s: 2 μM, BSA: 2 pM, DIG10.1a: 10 nM, DIG10.2: 1 nM, DIG10.3: 0.5 nM, DIG10.3 Y34F: 2 nM, DIG10.3 Y99F: 2 nM, DIG10.3 Y101F: 2 nM, DIG10.3 Y115: 2 nM, DIG10.3 Y99F/Y01F: 2 nM, DIG10.3 Y34F/Y99F/Y101F: 10 nM, and DIG10.3 Y34F/Y99F/Y101F/Y11S5F: 10 nM.

Fluorescence polarization equilibrium competition binding assays. Fluorescence polarization equilibrium competition binding assays were used to determine the binding affinities of DIG10.3 and its variants for unlabeled digoxigenin, digitoxigenin, progesterone, β-estradiol, and digoxin. In a typical experiment, the concentration of DIG-PEG$_3$-Alexa488 was kept near or below the K$_d$ of the interaction being monitored, the concentration of protein was fixed at a saturating value such that >95% the DIG-PEG$_3$-Alexa488 in the system was bound to protein, and the effects of increasing concentrations of unlabeled ligand on the fluorescence anisotropy of Alexa488 were determined as noted above. Unlabeled stock solutions of digoxigenin, digitoxigenin, progesterone, and β-estradiol were prepared in methanol. Unlabeled stock solutions of digoxin were prepared in DMSO. Ligand stock solutions were 10 mM for DIG, digitoxigenin, and digoxin, and 1 mM for progesterone and β-estradiol. For each ligand concentration, a negative control sample containing only DIG-PEG$_3$-Alexa488 and the appropriate dilution of a corresponding methanol-only control solution in PBS was measured. At all concentrations employed, methanol did not affect fluorescence anisotropy (data not shown). Similarly, the highest concentration of DMSO employed also did not affect fluorescence anisotropy (data not shown).

Fluorescence anisotropy (r) was measured as noted above. In all experiments, PBS (pH 7.4) was used as the buffer system and the temperature was 25° C. The concentration of total unlabeled ligand producing 50% binding signal inhibition (I$_{50}$) was determined by fitting a plot of the anisotropy averaged over a period of 30 min to 3 hr after reaction initiation versus unlabeled ligand concentration as described previously[47]. For some experiments, limiting steroid concentrations made it impossible to collect data in the regime of complete inhibition. In these cases, data were fit by fixing the anisotropy at infinite steroid concentration to a value measured for other steroids for which this value could be determined experimentally. For cases in which $K_d$ for steroid $\ll K_d$ for DIG-PEG$_3$-Alexa488, the data could not be fit to the model and only qualitative conclusions could be reached (FIG. 4, dashed lines).

The inhibition constant for each protein-ligand interaction, $K_i$, was calculated from the measured IC$_{50}$ and the $K_d$ of the protein-label interaction according to a model accounting for receptor-depletion conditions[47]. IC$_{50}$ values, the concentrations of free unlabeled ligand producing 50% binding signal inhibition, were calculated from the measured I$_{50}$ values[47]. Reported I$_{50}$ and subsequent K$_i$ values represent the average of at least three independent measurements from at least two batches of purified protein and a fresh unlabeled inhibitor stock prepared for each. For DIG10.3, [DIG-PEG$_3$-Alexa488]=1 nM and [DIG0.3-TEV-his$_6$]=20 nM. For DIG0.3 Y34F, [DIG-PEG$_3$-Alexa488]=10 nM and [DIG10.3 Y34F-TEV-his$_6$]=200 nM. For DIG10.3 Y101F, [DIG-PEG$_3$-Alexa488]=10 nM and [DIG10.3 Y101F-TEV-his$_6$]=200 nM. For DIG10.3 Y34F/Y99F/Y101F, [DIG-PEG$_3$-Alexa488]=500 nM and [DIG10.3 Y34F/Y99F/Y101F-TEV-his$_6$]=5 µM.

Circular dichroism spectroscopy. Circular dichroism spectra were collected on an Aviv 62A DS spectrometer. Samples were prepared in PBS. Fixed-temperature scans were conducted at 25° C. All proteins were stable <°60 C.

REFERENCES

1. Schreier, B., Stumpp, C., Wiesner, S., & Höcker, B. Computational design of ligand binding is not a solved problem. *Proc. Natl. Acad. Sci. USA* 106, 18491-18496 (2009).
2. de Wolf, F. A. & Brett, G. M. Ligand-binding proteins: their potential for application in systems for controlled delivery and uptake of ligands. *Pharmacol. Rev.* 52, 207-236 (2000).
3. Hunter, M. M., Margolies, M. N., Ju, A., & Haber, E. High-affinity monoclonal antibodies to the cardiac glycoside, digoxin. *J. Immunol.* 129, 1165-1172 (1982).
4. Shen. X. Y. Orson, F. M., & Kosten, T. R. Vaccines against drug abuse. *Clin. Pharmacol. Ther.* 91, 60-70 (2012).
5. Bradbury, A. R. M., Sidhu, S., Dübel, S., & McCafferty, J. Beyond natural antibodies: the power of in vitro display technologies. *Nat. Biotechnol.* 29, 245-254 (2011).
6. Brustad, E. M. & Arnold, F. H. Optimizing non-natural protein function with directed evolution. *Curr. Opin. Chem. Biol.* 15, 201-210 (2011).
7. Chen, G. et al. Isolation of high-affinity ligand-binding proteins by periplasmic expression with cytometric screening (PECS). *Nat. Biotechnol.* 19, 537-542 (2001).
8. Telmer, P. G. & Shilton, B. H. Structural studies of an engineered zinc biosensor reveal an unanticipated mode of zinc binding. *J. Mol. Biol.* 354, 829-840 (2005).
9. Baker, D. An exciting but challenging road ahead for computational enzyme design. *Protein Sci.* 19, 1817-1819 (2010).
10. Jiang, L. et al. De novo computational design of retro-Aldol enzymes. *Science* 319, 1387-1391 (2008).
11. Khare, S. D. & Fleishman, S. J. Emerging themes in the computational design of novel enzymes and protein-protein interfaces. *FEBS Lett.* In Press. (2013).
12. Khersonsky, O. et al. Bridging the gaps in design methodologies by evolutionary optimization of the stability and proficiency of designed Kemp eliminase KE59. *Proc. Natl. Acad. Sci. USA* 109, 10358-10363 (2012).
13. Röthlisberger, D. et al. Kemp elimination catalysts by computational enzyme design. *Nature* 453, 190-195 (2008).
14. Wang, L. et al. Structural analyses of covalent enzyme-substrate analog complexes reveal strengths and limitations of de novo enzyme design. *J. Mol. Biol.* 415, 615-625 (2012).
15. Boehr, D. D., Nussinov, R., & Wright, P. E. The role of dynamic conformational ensembles in biomolecular recognition. *Nat. Chem. Biol.* 5, 789-796 (2009).
16. Fleishman, S. J. Khare, S. D., Koga, N., & Baker. D. Restricted sidechain plasticity in the structures of native proteins and complexes. *Protein Sci.* 20, 753-757 (2011).
17. Lawrence, M. C. & Colman, P. M. Shape complementarity at protein/protein interfaces. *J. Mol. Biol.* 234, 946-950 (1993).
18. The Digitalis Investigation Group. The effect of digoxin on mortality and morbidity in patients with heart failure. *N. Engl. J. Med.* 336, 525-533 (1997).
19. Eisel, D., Seth, O., Grünewald-Janho, & Kruchen, B. *DIG application manual for nonradioactive in situ hybridization.* 4th ed. (Roche Diagnostics, Penzberg. 2008).
20. Flanagan, R. J. & Jones, A. L. Fab antibody fragments: some applications in clinical toxicology. *Drug Safety* 27, 1115-1133 (2004).
21. Chao, G. et al. Isolating and engineering human antibodies using yeast surface display. *Nat. Protoc.* 1, 755-768 (2006).
22. Fowler, D. M. et al. High-resolution mapping of protein sequence-function relationships. *Nat. Methods* 7, 741-746 (2010).
23. McLaughlin Jr. R. N., Poelwijk, F. J., Raman, A., Gosal, W. S., & Ranganathan, R. The spatial architecture of protein function and adaptation. *Nature* 491, 138-142 (2012).
24. Whitehead, T. A. et al. Optimization of affinity, specificity and function of designed influenza inhibitors using deep sequencing. *Nat. Biotechnol.* 30, 543-548 (2012).
25. Fersht, A. R. et al. Hydrogen bonding and biological specificity analysed by protein engineering. *Nature* 314, 235-238 (1985).
26. Frederick, K. K., Marlow, M. S., Valentine, K. G., & Wand, A. J. Conformational entropy in molecular recognition by proteins. *Nature* 448, 325-329 (2007).
27. Fleishman, S. J. & Baker, D. Role of the biomolecular energy gap in protein design, structure, and evolution. *Cell* 149, 262-273 (2012).
28. Zanghellini, A. et al. New algorithms and an in silico benchmark for computational enzyme design. *Protein Sci.* 15, 2785-2794 (2006).
29. Kuhlman, B. & Baker, D. Native protein sequences are close to optimal for their structures. *Proc. Natl. Acad. Sci. USA* 97, 10383-10388 (2000).
30. Rossi, A. M. & Taylor, C. W. Analysis of protein-ligand interactions by fluorescence polarization. *Nat. Protoc.* 6, 365-387 (2011).
31. Fleishman, S. J. et al. RosettaScripts: a scripting language interface to the Rosetta macromolecular modeling suite. *PLOS ONE* 6, e20161 (2011).
32. Zanghellini, A. et al. New algorithms and an in silico benchmark for computational enzyme design. *Protein Sci.* 15, 2785-2794 (2006).
33. Jiang. L. et al. De novo computational design of retro-aldol enzymes. *Science* 319, 1387-1391 (2008).

34. Röthlisberger, D. et al. Kemp elimination catalysts by computational enzyme design. *Nature* 453, 190-195 (2008).
35. Siegel, J. B. et al. Computational design of an enzyme catalyst for a stereoselective bimolecular Diels-Alder reaction. *Science* 329, 309-313 (2010).
36. Richter, F., Leaver-Fay, A., Khare, S. D., Bjelic, S., & Baker, D. De novo enzyme design using Rosetta3. *PLOS ONE* 6, e19230 (2011).
37. Kellogg, E. H., Leaver-Fay, A., & Baker, D. Role of conformational sampling in computing mutation-induced changes in protein structure and stability. *Proteins* 79, 830-838 (2010).
38. Cooper, S. et al. Predicting protein structures with a multiplayer online game. *Nature* 466, 756-760 (2010).
39. Fleishman, S. J., Khare, S. D., Koga, N., & Baker, D. Restricted sidechain plasticity in the structures of native proteins and complexes. *Protein Sci.* 20, 753-757 (2011).
40. Chao, G. et al. Isolating and engineering human antibodies using yeast surface display. *Nat. Protoc.* 1, 755-768 (2006).
41. Benatuil, L., Perez, J. M., Belk. J., & Hsieh, C.-M. An improved yeast transformation method for the generation of very large human antibody libraries. *Protein Eng. Des. Sel.* 23, 155-159 (2010).
42. Whitehead, T. A. et al. Optimization of affinity, specificity and function of designed influenza inhibitors using deep sequencing. *Nat. Biotechnol.* 30, 543-548 (2012).
43. Fowler, D. M., Araya, C. L., Gerard, W., & Fields, S. Enrich: software for analysis of protein function by enrichment and depletion of variants. *Bioinformatics* 27, 3430-3431 (2011).
44. Fowler, D. M. et al. High-resolution mapping of protein sequence-function relationships. *Nat. Methods* 7, 741-746 (2010).
45. McLaughlin Jr, R. N., Poelwijk, F. J., Raman, A., Gosal, W. S., & Ranganathan, R. The spatial architecture of protein function and adaptation. *Nature* 491, 138-142 (2012).
46. Rossi, A. M. & Taylor, C. W. Analysis of protein-ligand interactions by fluorescence polarization. *Nat. Protoc.* 6, 365-387 (2011).

We claim:

1. An isolated polypeptide comprising a polypeptide at least 95% identical along its entire length to the amino acid sequence selected from the group consisting of SEQ ID NOS:10-23 wherein the amino acid sequence is not the amino acid sequence of SEQ ID NO: 24, wherein the isolated polypeptide binds to one or more of digoxigenin, digitoxigenin, progesterone, and β-estradiol, and digoxin.

2. The isolated polypeptide of claim 1, comprising a polypeptide at least 98% identical along its entire length to the amino acid sequence selected from the group consisting of SEQ ID NOS:10-23, wherein the amino acid sequence is not the amino acid sequence of SEQ ID NO: 24.

3. The isolated polypeptide of claim 1, comprising a polypeptide at least 99% identical along its entire length to the amino acid sequence selected from the group consisting of SEQ ID NOS:10-23, wherein the amino acid sequence is not the amino acid sequence of SEQ ID NO: 24.

4. The isolated polypeptide of claim 1, comprising the amino acid sequence selected from the group consisting of SEQ ID NOS:10-23.

5. The isolated polypeptide of claim 1, further comprising a detectable tag.

6. A pharmaceutical composition, comprising one or more polypeptides of claim 1 and a pharmaceutically acceptable carrier.

7. A method for treating digoxin overdose and/or toxicity, comprising administering to a subject in need thereof an amount effective of the polypeptide of claim 4 to treat the digoxin toxicity.

8. A method for detecting digoxin, comprising contacting a sample of interest with the polypeptide of claim 1 under suitable conditions for binding the detectable polypeptide to digoxin present in the sample to form a polypeptide-digoxin binding complex, and detecting the polypeptide-digoxin binding complex.

9. A pharmaceutical composition, comprising one or more polypeptides of claim 2 and a pharmaceutically acceptable carrier.

10. A pharmaceutical composition, comprising one or more polypeptides of claim 3 and a pharmaceutically acceptable carrier.

11. A pharmaceutical composition, comprising one or more polypeptides of claim 4 and a pharmaceutically acceptable carrier.

* * * * *